United States Patent
Argento et al.

(10) Patent No.: US 10,912,644 B2
(45) Date of Patent: Feb. 9, 2021

(54) PROSTHETIC CARDIAC VALVE DEVICES, SYSTEMS, AND METHODS

(71) Applicant: Shifamed Holdings, LLC, Campbell, CA (US)

(72) Inventors: Claudio Argento, Felton, CA (US); Andrew Backus, Santa Cruz, CA (US); Alice Yang, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/594,946

(22) Filed: Oct. 7, 2019

(65) Prior Publication Data
US 2020/0107930 A1 Apr. 9, 2020

Related U.S. Application Data

(60) Provisional application No. 62/742,043, filed on Oct. 5, 2018, provisional application No. 62/755,996, filed on Nov. 5, 2018.

(51) Int. Cl.
*A61F 2/24* (2006.01)

(52) U.S. Cl.
CPC .......... *A61F 2/2433* (2013.01); *A61F 2/2418* (2013.01); *A61F 2/2427* (2013.01); *A61F 2/2457* (2013.01); *A61F 2/2466* (2013.01); *A61F 2210/0014* (2013.01); *A61F 2220/0008* (2013.01)

(58) Field of Classification Search
CPC .... A61F 2/2418; A61F 2/2427; A61F 2/2433; A61F 2/2457; A61F 2/2466; A61F 2210/0014; A61F 2220/0008
See application file for complete search history.

(56) References Cited

U.S. PATENT DOCUMENTS

| | | |
|---|---|---|
| 5,327,905 A | 7/1994 | Avitall |
| 5,370,685 A | 12/1994 | Stevens |
| 5,755,601 A | 5/1998 | Jones |
| 5,873,835 A | 2/1999 | Hastings et al. |
| 5,944,690 A | 8/1999 | Falwell et al. |
| 6,048,339 A | 4/2000 | Zirps et al. |

(Continued)

FOREIGN PATENT DOCUMENTS

| | | |
|---|---|---|
| AU | 2012261727 B2 | 10/2015 |
| CA | 2979817 A1 | 9/2016 |

(Continued)

OTHER PUBLICATIONS

Co-pending U.S. Appl. No. 16/546,901, filed on Aug. 21, 2019.

(Continued)

*Primary Examiner* — Kathleen S Holwerda
*Assistant Examiner* — Kankindi Rwego
(74) *Attorney, Agent, or Firm* — Shay Glenn LLP

(57) ABSTRACT

Systems, devices, and methods for treating a diseased native valve in a patient, the system comprising a compressible and expandable frame structure and an anchor. The anchor comprises a wire having a free end and is configured to be fully advanced from an atrial side of a native valve in a patient into a ventricle of the heart and anchor the frame structure to the native valve when the frame structure is in the expanded configuration adjacent the native valve.

30 Claims, 43 Drawing Sheets

(56) References Cited

U.S. PATENT DOCUMENTS

| | | | |
|---|---|---|---|
| 6,053,873 | A | 4/2000 | Govari et al. |
| 6,419,695 | B1 | 7/2002 | Gabbay |
| 6,419,696 | B1 | 7/2002 | Ortiz et al. |
| 6,530,952 | B2 | 3/2003 | Vesely |
| 6,533,783 | B1 | 3/2003 | Töllner |
| 6,641,553 | B1 | 11/2003 | Chee et al. |
| 6,752,813 | B2 | 6/2004 | Goldfarb et al. |
| 6,869,444 | B2 | 3/2005 | Gabbay |
| 6,964,684 | B2 | 11/2005 | Ortiz et al. |
| 6,974,476 | B2 | 12/2005 | McGuckin, Jr. et al. |
| 7,077,861 | B2 | 7/2006 | Spence |
| 7,101,395 | B2 | 9/2006 | Tremulis et al. |
| 7,125,421 | B2 | 10/2006 | Tremulis et al. |
| 7,160,322 | B2 | 1/2007 | Gabbay |
| 7,175,656 | B2 | 2/2007 | Khairkhahan |
| 7,226,467 | B2 | 6/2007 | Lucatero et al. |
| 7,329,279 | B2 | 2/2008 | Haug et al. |
| 7,381,219 | B2 | 6/2008 | Salahieh et al. |
| 7,445,631 | B2 | 11/2008 | Salahieh et al. |
| 7,527,647 | B2 | 5/2009 | Spence |
| 7,563,267 | B2 | 7/2009 | Goldfarb et al. |
| 7,594,903 | B2 | 9/2009 | Webler et al. |
| 7,604,646 | B2 | 10/2009 | Goldfarb et al. |
| 7,608,091 | B2 | 10/2009 | Goldfarb et al. |
| 7,618,449 | B2 | 11/2009 | Tremulis et al. |
| 7,621,948 | B2 | 11/2009 | Herrmann et al. |
| 7,666,204 | B2 | 2/2010 | Thornton et al. |
| 7,704,269 | B2 | 4/2010 | St. Goar et al. |
| 7,731,705 | B2 | 6/2010 | Wardle |
| 7,748,389 | B2 | 7/2010 | Salahieh et al. |
| 7,749,266 | B2 | 7/2010 | Forster et al. |
| 7,780,725 | B2 | 8/2010 | Haug et al. |
| 7,811,296 | B2 | 10/2010 | Goldfarb et al. |
| 7,824,442 | B2 | 11/2010 | Salahieh et al. |
| 7,824,443 | B2 | 11/2010 | Salahieh et al. |
| 7,846,203 | B2 | 12/2010 | Cribier |
| 7,947,075 | B2 | 5/2011 | Goetz et al. |
| 7,951,195 | B2 | 5/2011 | Antonsson et al. |
| 7,959,666 | B2 | 6/2011 | Salahieh et al. |
| 7,988,724 | B2 | 8/2011 | Salahieh et al. |
| 8,052,749 | B2 | 11/2011 | Salahieh et al. |
| 8,052,750 | B2 | 11/2011 | Tuval et al. |
| 8,075,615 | B2 | 12/2011 | Eberhardt et al. |
| 8,096,985 | B2 | 1/2012 | Legaspi et al. |
| 8,147,541 | B2 | 4/2012 | Forster et al. |
| 8,147,542 | B2 | 4/2012 | Maisano et al. |
| 8,182,528 | B2 | 5/2012 | Salahieh et al. |
| 8,216,256 | B2 | 7/2012 | Raschdorf et al. |
| 8,236,049 | B2 | 8/2012 | Rowe et al. |
| 8,241,351 | B2 | 8/2012 | Cabiri |
| 8,251,977 | B2 | 8/2012 | Partlett |
| 8,252,050 | B2 | 8/2012 | Maisano et al. |
| 8,287,584 | B2 | 10/2012 | Salahieh et al. |
| 8,313,526 | B2 | 11/2012 | Hoffman et al. |
| 8,323,241 | B2 | 12/2012 | Salahieh et al. |
| 8,323,336 | B2 | 12/2012 | Hill et al. |
| 8,328,868 | B2 | 12/2012 | Paul et al. |
| 8,343,213 | B2 | 1/2013 | Salahieh et al. |
| 8,348,995 | B2 | 1/2013 | Tuval et al. |
| 8,348,996 | B2 | 1/2013 | Tuval et al. |
| 8,403,981 | B2 | 3/2013 | Forster et al. |
| 8,403,983 | B2 | 3/2013 | Quadri et al. |
| 8,414,643 | B2 | 4/2013 | Tuval et al. |
| 8,414,644 | B2 | 4/2013 | Quadri et al. |
| 8,414,645 | B2 | 4/2013 | Dwork et al. |
| 8,449,599 | B2 | 5/2013 | Chau et al. |
| 8,465,541 | B2 | 6/2013 | Dwork |
| 8,500,800 | B2 | 8/2013 | Maisano et al. |
| 8,512,401 | B2 | 8/2013 | Murray et al. |
| 8,523,881 | B2 | 9/2013 | Cabiri et al. |
| 8,545,553 | B2 | 10/2013 | Zipory et al. |
| 8,556,963 | B2 | 10/2013 | Tremulis et al. |
| 8,562,645 | B2 | 10/2013 | Stone et al. |
| 8,562,673 | B2 | 10/2013 | Yeung et al. |
| 8,579,962 | B2 | 11/2013 | Salahieh et al. |
| 8,603,157 | B2 | 12/2013 | Seguin et al. |
| 8,603,160 | B2 | 12/2013 | Salahieh et al. |
| 8,623,075 | B2 | 1/2014 | Murray et al. |
| 8,628,570 | B2 | 1/2014 | Seguin |
| 8,641,727 | B2 | 2/2014 | Starksen et al. |
| 8,652,202 | B2 | 2/2014 | Alon et al. |
| 8,652,203 | B2 | 2/2014 | Quadri |
| 8,657,872 | B2 | 2/2014 | Seguin |
| 8,696,693 | B2 | 4/2014 | Najafi et al. |
| 8,715,300 | B2 | 5/2014 | Najafi et al. |
| 8,715,342 | B2 | 5/2014 | Zipory et al. |
| 8,740,976 | B2 | 6/2014 | Tran et al. |
| 8,784,479 | B2 | 7/2014 | Antonsson et al. |
| 8,790,367 | B2 | 7/2014 | Nguyen et al. |
| 8,808,368 | B2 | 8/2014 | Maisano et al. |
| 8,828,078 | B2 | 9/2014 | Salahieh et al. |
| 8,834,564 | B2 | 9/2014 | Tuval et al. |
| 8,840,663 | B2 | 9/2014 | Salahieh et al. |
| 8,852,271 | B2 | 10/2014 | Murray et al. |
| 8,876,893 | B2 | 11/2014 | Dwork et al. |
| 8,876,894 | B2 | 11/2014 | Tuval et al. |
| 8,876,895 | B2 | 11/2014 | Tuval et al. |
| 8,900,294 | B2 | 12/2014 | Paniagua et al. |
| 8,911,494 | B2 | 12/2014 | Hammer et al. |
| 8,920,369 | B2 | 12/2014 | Salahieh et al. |
| 8,926,696 | B2 | 1/2015 | Cabiri et al. |
| 8,926,697 | B2 | 1/2015 | Gross et al. |
| 8,940,002 | B2 | 1/2015 | Goertzen |
| 8,940,044 | B2 | 1/2015 | Hammer et al. |
| 8,951,299 | B2 | 2/2015 | Paul et al. |
| 8,998,980 | B2 | 4/2015 | Shipley et al. |
| 9,005,273 | B2 | 4/2015 | Salahieh et al. |
| 9,011,515 | B2 | 4/2015 | Schweich et al. |
| 9,011,523 | B2 | 4/2015 | Seguin |
| 9,011,530 | B2 | 4/2015 | Reich et al. |
| 9,017,408 | B2 | 4/2015 | Siegal et al. |
| 9,023,100 | B2 | 5/2015 | Quadri et al. |
| 9,034,032 | B2 | 5/2015 | McLean et al. |
| 9,039,757 | B2 | 5/2015 | McLean et al. |
| 9,056,009 | B2 | 6/2015 | Keränen |
| 9,061,120 | B2 | 6/2015 | Osypka et al. |
| 9,119,719 | B2 | 9/2015 | Zipory et al. |
| 9,125,739 | B2 | 9/2015 | Paniagua et al. |
| 9,125,740 | B2 | 9/2015 | Morriss et al. |
| 9,155,619 | B2 | 10/2015 | Liu et al. |
| 9,168,129 | B2 | 10/2015 | Valdez et al. |
| 9,173,713 | B2 | 11/2015 | Hart et al. |
| 9,173,737 | B2 | 11/2015 | Hill et al. |
| 9,180,006 | B2 | 11/2015 | Keränen |
| 9,277,994 | B2 | 3/2016 | Miller et al. |
| 9,289,297 | B2 | 3/2016 | Wilson et al. |
| 9,301,756 | B2 | 4/2016 | Wardle |
| 9,320,597 | B2 | 4/2016 | Savage et al. |
| 9,343,224 | B2 | 5/2016 | Zilbershlag |
| 9,358,110 | B2 | 6/2016 | Paul et al. |
| 9,427,315 | B2 | 8/2016 | Schweich et al. |
| 9,474,606 | B2 | 10/2016 | Zipory et al. |
| 9,474,840 | B2 | 10/2016 | Siess |
| 9,480,559 | B2 | 11/2016 | Vidlund et al. |
| 9,526,487 | B2 | 12/2016 | Rahmani |
| 9,526,609 | B2 | 12/2016 | Salahieh et al. |
| 9,532,870 | B2 | 1/2017 | Cooper et al. |
| 9,561,102 | B2 | 2/2017 | Rust et al. |
| 9,572,662 | B2 | 2/2017 | Morriss et al. |
| 9,579,196 | B2 | 2/2017 | Morriss et al. |
| 9,579,198 | B2 | 2/2017 | Deem et al. |
| 9,585,751 | B2 | 3/2017 | Morriss et al. |
| 9,636,224 | B2 | 5/2017 | Zipory et al. |
| 9,636,481 | B2 | 5/2017 | Campbell et al. |
| 9,662,209 | B2 | 5/2017 | Gross et al. |
| 9,675,454 | B2 | 6/2017 | Vidlund et al. |
| 9,724,192 | B2 | 8/2017 | Sheps et al. |
| 9,730,790 | B2 | 8/2017 | Quadri et al. |
| 9,730,793 | B2 | 8/2017 | Reich et al. |
| 9,744,038 | B2 | 8/2017 | Dahlgren et al. |
| 9,750,605 | B2 | 9/2017 | Ganesan et al. |
| 9,763,780 | B2 | 9/2017 | Morriss et al. |
| 9,814,611 | B2 | 11/2017 | Cartledge et al. |
| 9,827,090 | B2 | 11/2017 | Hill et al. |

(56) References Cited

U.S. PATENT DOCUMENTS

| | | |
|---|---|---|
| 9,861,480 B2 | 1/2018 | Zakai et al. |
| 9,867,700 B2 | 1/2018 | Bakis et al. |
| 9,867,702 B2 | 1/2018 | Keränen et al. |
| 9,895,221 B2 | 2/2018 | Vidlund |
| 9,901,444 B2 | 2/2018 | Valdez et al. |
| 9,918,840 B2 | 3/2018 | Reich et al. |
| D815,744 S | 4/2018 | Ratz et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,650 B2 | 5/2018 | Nguyen-Thien-Nhon et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,827 B2 | 7/2018 | Morriss et al. |
| 10,028,832 B2 | 7/2018 | Quill et al. |
| 10,029,037 B2 | 7/2018 | Muller et al. |
| 10,034,749 B2 | 7/2018 | Spence et al. |
| 10,034,750 B2 | 7/2018 | Morriss et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,070,954 B2 | 9/2018 | Braido et al. |
| 10,092,400 B2 | 10/2018 | Jimenez et al. |
| 10,105,217 B2 | 10/2018 | Keränen et al. |
| 10,130,464 B2 | 11/2018 | Meiri et al. |
| 10,130,471 B2 | 11/2018 | Keränen |
| 10,149,759 B2 | 12/2018 | Naor |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi et al. |
| 10,195,028 B2 | 2/2019 | Hosmer et al. |
| 10,195,029 B2 | 2/2019 | Keränen |
| 10,201,418 B2 | 2/2019 | Biadillah et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 | 3/2019 | Spence et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,131 B2 | 7/2019 | Eidenschink et al. |
| 10,368,986 B2 | 8/2019 | Gosal et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,433,961 B2 | 10/2019 | McLean |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |
| 10,524,901 B2 | 1/2020 | Quadri et al. |
| 10,548,729 B2 | 2/2020 | Zipory et al. |
| 10,575,951 B2 | 3/2020 | Johnson et al. |
| 10,603,165 B2 | 3/2020 | Maimon et al. |
| 10,639,154 B2 | 5/2020 | Seguin |
| 2002/0173841 A1 | 11/2002 | Ortiz et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahieh et al. |
| 2005/0165344 A1 | 7/2005 | Dobak, III |
| 2006/0009841 A1* | 1/2006 | McGuckin, Jr. ...... A61F 2/2412 623/2.38 |
| 2006/0178700 A1 | 8/2006 | Quinn |
| 2006/0293698 A1 | 12/2006 | Douk |
| 2007/0055206 A1 | 3/2007 | To et al. |
| 2007/0118151 A1 | 5/2007 | Davidson |
| 2007/0185572 A1 | 8/2007 | Solem et al. |
| 2007/0255396 A1 | 11/2007 | Douk et al. |
| 2007/0293943 A1 | 12/2007 | Quinn |
| 2008/0208327 A1 | 8/2008 | Rowe |
| 2008/0275503 A1 | 11/2008 | Spence et al. |
| 2009/0093826 A1 | 4/2009 | Warder-Gabaldon |
| 2009/0209950 A1 | 8/2009 | Starksen |
| 2009/0276040 A1 | 11/2009 | Rowe et al. |
| 2010/0049239 A1 | 2/2010 | McGuckin, Jr. et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2011/0022164 A1 | 1/2011 | Quinn et al. |
| 2011/0046600 A1 | 2/2011 | Crank |
| 2011/0224785 A1 | 9/2011 | Hacohen |
| 2011/0288637 A1 | 11/2011 | De Marchena |
| 2011/0313515 A1 | 12/2011 | Quadri et al. |
| 2012/0016464 A1 | 1/2012 | Seguin |
| 2012/0022633 A1 | 1/2012 | Olson et al. |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0123912 A1 | 5/2013 | Tung et al. |
| 2013/0274873 A1 | 10/2013 | Delaloye et al. |
| 2014/0249621 A1 | 9/2014 | Eidenschink |
| 2014/0257467 A1 | 9/2014 | Lane et al. |
| 2014/0324163 A1 | 10/2014 | Keränen et al. |
| 2015/0173897 A1 | 6/2015 | Raanani et al. |
| 2015/0250480 A1 | 9/2015 | Featherstone |
| 2015/0265403 A1 | 9/2015 | Keränen |
| 2015/0272737 A1 | 10/2015 | Dale et al. |
| 2015/0327994 A1 | 11/2015 | Morriss et al. |
| 2015/0328000 A1 | 11/2015 | Rat et al. |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0095705 A1 | 4/2016 | Keränen et al. |
| 2016/0166380 A1 | 6/2016 | Seguin et al. |
| 2016/0235526 A1 | 8/2016 | Lashinski et al. |
| 2016/0242902 A1 | 8/2016 | Morriss et al. |
| 2016/0242906 A1 | 8/2016 | Morriss et al. |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2017/0056163 A1 | 3/2017 | Tayeb et al. |
| 2017/0119524 A1 | 5/2017 | Salahieh et al. |
| 2017/0128203 A1 | 5/2017 | Zhang et al. |
| 2017/0128204 A1 | 5/2017 | Morriss et al. |
| 2017/0143481 A1 | 5/2017 | Morriss et al. |
| 2017/0156723 A1 | 6/2017 | Keating et al. |
| 2017/0165057 A9 | 6/2017 | Morriss et al. |
| 2017/0216025 A1 | 8/2017 | Nitzan et al. |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0348099 A1 | 12/2017 | Mendelson et al. |

(56) References Cited

U.S. PATENT DOCUMENTS

| | | |
|---|---|---|
| 2018/0049873 A1 | 2/2018 | Manash et al. |
| 2018/0055628 A1 | 3/2018 | Patel et al. |
| 2018/0110622 A1 | 4/2018 | Gregg et al. |
| 2018/0116790 A1 | 5/2018 | Ratz et al. |
| 2018/0133003 A1 | 5/2018 | Levi |
| 2018/0177594 A1 | 6/2018 | Patel et al. |
| 2018/0206982 A1 | 7/2018 | Halvatov et al. |
| 2018/0206992 A1 | 7/2018 | Brown |
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Shops et al. |
| 2018/0228610 A1 | 8/2018 | Lashinski et al. |
| 2018/0235443 A1 | 8/2018 | Smith et al. |
| 2018/0263764 A1 | 9/2018 | Manash et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1 | 11/2018 | Patel et al. |
| 2018/0344303 A1 | 12/2018 | Bambury et al. |
| 2018/0344454 A1 | 12/2018 | Mauch et al. |
| 2018/0344459 A1 | 12/2018 | Spence et al. |
| 2018/0368830 A1 | 12/2018 | O'Carroll et al. |
| 2019/0000614 A1 | 1/2019 | Morriss et al. |
| 2019/0000625 A1 | 1/2019 | O'Carroll et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0159770 A1 | 5/2019 | Rohl et al. |
| 2019/0167425 A1 | 6/2019 | Reich et al. |
| 2019/0183649 A1 | 6/2019 | Allen et al. |
| 2019/0192294 A1 | 6/2019 | Spence et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0231520 A1 | 8/2019 | Desrosiers et al. |
| 2019/0240023 A1 | 8/2019 | Spence et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328518 A1 | 10/2019 | Neumann |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0022811 A1 | 1/2020 | Griswold et al. |
| 2020/0054453 A1 | 2/2020 | Zerkowski et al. |
| 2020/0060852 A1 | 2/2020 | Argento et al. |
| 2020/0078000 A1 | 3/2020 | Rajagopal et al. |
| 2020/0093601 A1 | 3/2020 | Neustadter |
| 2020/0107933 A1 | 4/2020 | Oba |
| 2020/0113586 A1 | 4/2020 | Karasic et al. |
| 2020/0113685 A1 | 4/2020 | Miller et al. |

FOREIGN PATENT DOCUMENTS

| | | |
|---|---|---|
| CA | 2954826 C | 10/2019 |
| EP | 1432369 B1 | 2/2008 |
| EP | 2907479 A1 | 8/2015 |
| EP | 3037064 A1 | 6/2016 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 3554424 A1 | 10/2019 |
| EP | 3244809 B1 | 2/2020 |
| EP | 3639792 A1 | 4/2020 |
| KR | 2020032237 A | 3/2020 |
| KR | 2020033349 A | 3/2020 |
| KR | 2020033350 A | 3/2020 |
| WO | WO2011/025945 A1 | 3/2011 |
| WO | WO2012/145545 A1 | 10/2012 |
| WO | WO-2013114214 A2 | 8/2013 |
| WO | WO-2015023579 A1 | 2/2015 |
| WO | WO-2015127264 A1 | 8/2015 |
| WO | WO-2017151566 A1 | 9/2017 |
| WO | WO2017/214098 A1 | 12/2017 |
| WO | WO2018/119304 A1 | 6/2018 |
| WO | WO2018/178967 A1 | 10/2018 |
| WO | WO2018/187390 A1 | 10/2018 |
| WO | WO2018/192197 A1 | 10/2018 |
| WO | WO-2019010370 A1 | 1/2019 |
| WO | WO2019/036592 A1 | 2/2019 |
| WO | WO2019/081777 A1 | 5/2019 |
| WO | WO2019/102484 A1 | 5/2019 |
| WO | WO-2019086958 A1 | 5/2019 |
| WO | WO-2019118371 A1 | 6/2019 |
| WO | WO2019/135011 A1 | 7/2019 |
| WO | WO2019/135028 A1 | 7/2019 |
| WO | WO2019/147504 A1 | 8/2019 |
| WO | WO2019/147846 A2 | 8/2019 |
| WO | WO2019/195860 A2 | 10/2019 |
| WO | WO2019/209927 A1 | 10/2019 |
| WO | WO2019/222694 A1 | 11/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |

OTHER PUBLICATIONS

PCT/US2019/055049 International Search Report dated Dec. 2, 2019.

Westaby et al.; Adult human valve dimensions and their surgical significance; The American Journal of Cardiology; 53(4); pp. 552-556; Feb. 1984.

Argento et al.; U.S. Appl. No. 16/723,537 entitled "Prothetic cardiac valve devices, systems, and methods," filed Dec. 20, 2019.

Argento et al.; U.S. Appl. No. 16/824,576 entitled "Prosthetic cardiac valve devices, systems, and methods," filed Mar. 19, 2020.

\* cited by examiner

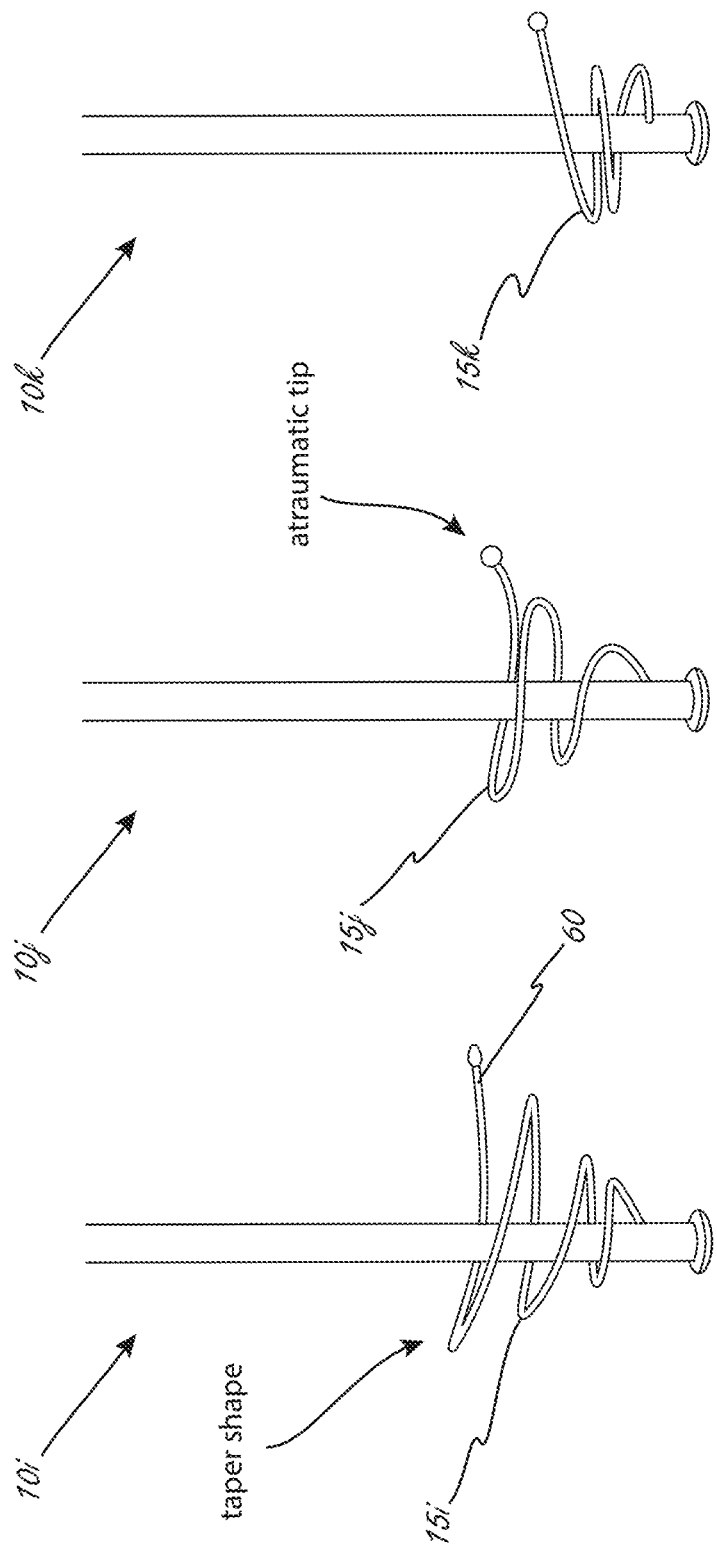

B-B

PROSTHETIC CARDIAC VALVE DEVICES, SYSTEMS, AND METHODS

CROSS-REFERENCE

This application claims the benefit of U.S. Provisional Application No. 62/742,043, filed Oct. 5, 2018, entitled "Prosthetic Cardiac Valve Devices, Systems, and Methods"; and U.S. Provisional Application No. 62/755,996, filed Nov. 5, 2018, entitled "Prosthetic Cardiac Valve Devices, Systems, and Methods"; which are incorporated herein by reference for all purposes in their entireties.

This application is related to U.S. Provisional Application No. 62/720,853, filed Aug. 21, 2018, entitled "Prosthetic Cardiac Valve Devices, Systems, and Methods"; U.S. patent application Ser. No. 16/546,901, filed Aug. 21, 2019, entitled "Prosthetic Cardiac Valve Devices, Systems, and Methods"; U.S. Provisional Application No. 62/748,162, filed Oct. 19, 2019, entitled "Adjustable Medical Device"; U.S. Provisional Application No. 62/784,280, filed Dec. 21, 2018, entitled "Prosthetic Cardiac Valve Devices, Systems, and Methods"; U.S. Provisional Application No. 62/813,963, filed Mar. 5, 2019, entitled "Prosthetic Cardiac Valve Devices, Systems, and Methods"; U.S. Provisional Application No. 62/815,791, filed Mar. 8, 2019, entitled "Prosthetic Cardiac Valve Devices, Systems, and Methods"; U.S. Provisional Application No. 62/820,570, filed Mar. 19, 2019, entitled "Prosthetic Cardiac Valve Delivery Devices, Systems, and Methods"; U.S. Provisional Application No. 62/828,835, filed Apr. 3, 2019, entitled "Prosthetic Cardiac Valve Devices, Systems, and Methods"; U.S. Provisional Application No. 62/833,425, filed Apr. 12, 2019, entitled "Minimal Frame Prosthetic Cardiac Valve Delivery Devices, Systems, and Methods"; U.S. Provisional Application No. 62/833,430 filed Apr. 12, 2019, entitled "Prosthetic Cardiac Valve Delivery Devices, Systems, and Methods"; U.S. Provisional Application No. 62/851,245, filed May 22, 2019, entitled "Prosthetic Cardiac Valve Devices, Systems, and Methods"; U.S. Provisional Application No. 62/872,016, filed Jul. 9, 2019, entitled "Prosthetic Cardiac Valve Delivery Devices, Systems, and Methods"; U.S. Provisional Application No. 62/873,454, filed Jul. 12, 2019, entitled "Systems, Methods, and Devices for Expandable Sensors"; U.S. Provisional Application No. 62/879,979, filed Jul. 29, 2019, entitled "Prosthetic Cardiac Valve Devices, Systems, and Methods"; and U.S. Provisional Application No. 62/894,565, filed Aug. 30, 2019, entitled "Prosthetic Cardiac Valve Devices, Systems, and Methods"; which are incorporated herein by reference for all purposes in their entireties.

BACKGROUND

Blood flow between and out of heart chambers is regulated by native valves—the mitral valve, the aortic valve, the pulmonary valve, and the tricuspid valve. Each of these valves are passive one-way valves which open and close in response to differential pressures. Patients with valvular disease have abnormal anatomy and/or function of at least one valve. For example, a valve may suffer from insufficiency, also referred to as regurgitation, when the valve does not fully close and allows blood to flow retrograde. Valve stenosis can cause a valve to fail to open properly. Other diseases may also lead to dysfunction of the valves. While medications may be used to treat the disease, in many cases the defective valve may need to be repaired or replaced at some point during the patient's lifetime. Existing valves and surgical repair and/or replacement procedures may have increased risks, limited lifespans, and/or are highly invasive. Some less-invasive transcatheter options are available, however these generally are limited to aortic valve procedures, are limited in their patient-to-patient flexibility, and often take longer than desired to implant.

Referring to FIGS. 1 and 2, the heart 2 includes four chambers connected by four valves. The upper part of the heart 2 includes the left atrium 25 and right atrium 5. The lower part includes the left ventricle 26 and right ventricle 6. The heart 2 and cardiovascular system operates like a closed circuit. The right side of the heart 2 receives de-oxygenated blood from the body and delivers the blood through the pulmonary artery 7 to the lungs where it becomes re-oxygenated. The oxygenated blood is returned to the left side of the heart 2, referred to as the systemic side, which delivers the oxygenated blood throughout the body.

Blood flow between the heart chambers is regulated by the valves. On the left side of the heart, the mitral valve 4 is located between the left atrium 25 and the left ventricle 26 and the aortic valve 9 is located between the left ventricle 26 and the aorta 1. On the right side of the heart 2, the pulmonary valve 3 is located between the right ventricle 6 and the pulmonary artery 7 and the tricuspid valve 8 is located between the right ventricle 6 and the right atrium 5.

All four of heart valves are passive one-way valves with "leaflets" which open and close in response to differential pressures. For example, in a healthy heart during systole the left ventricle 26 contracts and pushes blood out the aortic valve 9. In turn, the pressure in the left ventricle 26 causes the mitral valve 4 to close thereby preventing blood from going back into the left atrium 25 during systole.

A significant population will acquire valve disease in their lifetime. Congenital heart disease is also a significant problem. Patients with valvular disease have abnormal anatomy and/or function of at least one valve. Congenital valve abnormalities may be tolerated and/or treated palliatively for some years before developing into a life-threatening problem in later years. However, congenital heart disease may present life-threatening risk without notice. Patients may acquire valvular disease from rheumatic fever, heart failure, degenerative leaflet tissue, bacterial infection, and more.

Valvular disease may be caused by several factors as shown in FIGS. 3 to 5. FIG. 3 shows a healthy mitral valve 4. Referring to FIGS. 4 to 5 show a diseased mitral valve 4. The valve 4 in FIG. 4 suffers from insufficiency, also referred to as regurgitation. Such a valve 4 does not fully close and allows blood to flow retrograde. In this case, blood will flow back into the left atrium 25 during systole. FIG. 5 shows a mitral valve 4 with stenosis. Such a valve 4 does not open properly. Some valves 4 can have concomitant insufficiency and stenosis. Other diseases may also be present, such as Barlow's disease, which prevent the valve 4 from functioning properly. These diseases reduce cardiac output and force the heart 2 to work harder, thus increasing the risk of heart failure and chordae failures.

While medications may be used to treat the disease, in many cases the defective valve may need to be repaired or replaced at some point during the patient's lifetime. The native valve can be replaced with a mechanical valve or tissue valve. Mechanical valves have a disc or other member which opens and closes. Although mechanical valves are formed of biocompatible materials, they carry an increased risk of clotting. Thus, patients usually need to take anticoagulants for the remainder of their lives, which presents additional complications. Tissue valves can be formed of human or animal tissue, as well as polymeric materials. Tissue valves, unlike mechanical valves, do not typically require long-term use of anti-coagulants, but because they are formed of a living tissue they are not as widely available nor do they last as long as mechanical valves. Common tissue valves include porcine aortic valves mounted within a stent-like structure.

More recently there has been increased interest in less invasive procedures for implantation of prosthetic valves. One type of percutaneous procedure involves using a catheter to place a prosthetic valve inside of a diseased or injured heart valve.

Existing percutaneous procedures for valve repair still face many challenges. These challenges have limited the adoption of transcatheter procedures to certain patient populations and anatomies. Thus far, transcatheter devices are largely focused on aortic valve procedures and the sickest patient populations who may not be able to tolerate surgery. There is a continuing need for improved transcatheter devices which meet or exceed the performance and safety of surgical valves. Percutaneous valve replacement has also been limited to aortic valve procedures. While a large segment of the population suffers from tricuspid and mitral valve disease, the anatomy and function of these valves present challenges to transcatheter replacement. The aortic valve can be accessed via the femoral artery whereas the mitral valve, for example, typically requires a transseptal approach. The mitral valve anatomy presents more complexities to transcatheter procedures than the aortic valve. For example, as shown in FIG. 4, the mitral valve 4 includes two asymmetrical leaflets 4a, 4b and an irregularly-shaped annulus 4c. The mitral valve 4 also varies far more considerably patient-to-patient than the aortic valve. For these and other reasons, surgical replacement and percutaneous repair thus far are the only widely-available commercial treatments for mitral valve disease.

SUMMARY OF THE DISCLOSURE

It would therefore be desirable to provide a less invasive procedure for repair and replacement of heart valves, including the mitral valve, quicker surgical methods, a variety of different valve assemblies to accommodate the requirements of different patients, and/or prosthetic valves that can accommodate a variety of individual patients. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure relates generally to treatment of heart disease, and more particularly, implantable valve prostheses and treatments for heart valve diseases.

The present disclosure generally relates to treating a diseased native valve in a patient and more particularly relates to prosthetic heart valves.

The present disclosure relates prosthetic cardiac devices, and in some embodiments, prosthetic heart valves such as catheter-based mitral valves.

An aspect of the present disclosure provides a method for treating a diseased native valve in a patient. The method comprises advancing a distal end of a delivery device to a first side of a native valve, wherein the distal end of the delivery device is detachably coupled to an anchor and a frame structure; deploying the anchor from a delivery configuration to a deployed configuration on the first side of the native valve; advancing the anchor in the deployed configuration from the first side of the native valve to a second side of the native valve; rotating a free end of the anchor in the deployed configuration around one or more structures on the second side of the native valve; releasing the anchor from the distal end of the delivery device; expanding the frame structure within the native valve from a compressed configuration to an expanded configuration; releasing the frame structure from the distal end of the delivery device; and retracting the delivery device from the native valve.

In some embodiments, the method may further comprise positioning the anchor such that it is located only on the second side of the native valve after advancing the distal end of the delivery device from the first side of the native valve to the second side of the native valve.

In some embodiments, the method may further comprise steering the distal end of the delivery device such that the distal end of the delivery device points towards the first side of the native valve.

In some embodiments, advancing the anchor may comprise pushing the anchor through the native valve. Alternatively, or in combination, advancing the anchor may comprise rotating the anchor through the native valve.

In some embodiments, advancing the anchor may comprise positioning the anchor such that it is located only on the second side of the native valve.

In some embodiments, the frame structure may comprise a first and second opposite ends. Expanding the frame structure may comprise expanding the frame structure such that the first end extends above the first side of the native valve and the second end extends below second side of the native valve.

In some embodiments, expanding the frame structure may comprise expanding at least a portion the frame structure within at least a portion of the deployed anchor to anchor the frame structure to the native valve.

In some embodiments, expanding the frame structure and releasing the frame structure may occur simultaneously.

In some embodiments, the frame structure may be balloon-expandable. Expanding the frame structure may comprise inflating a balloon disposed within the frame structure. Inflation of the balloon may cause expansion of the frame structure.

In some embodiments, the frame structure may be self-expanding. Expanding the frame structure may comprise releasing the frame structure from radial constriction by the delivery device.

In some embodiments, the one or more structures may comprise one or more valve leaflets of the native valve. Alternatively, or in combination, the one or more structures may comprise one or more chordae of the left ventricle.

In some embodiments, the free end may be disposed radially outward from a main body of the anchor in the deployed configuration in order to facilitate rotation of the free end around the one or more structures.

In some embodiments, the free end of the wire may comprise an atraumatic tip. For example, the free end may comprise a ball tip.

In some embodiments, the free end of the wire may be configured for piercing tissue.

In some embodiments, the anchor may comprise a curved wire. In some embodiments, the curved wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having the same or different diameters. Alternatively, or in combination, the anchor may comprise at least two helical wires having the same or different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the helical wire may have a generally cylindrical shape. The free end of the helical wire may extend radially outward from the cylindrical shape.

In some embodiments, the frame structure may further comprise a valve segment within the frame structure comprising a biocompatible one-way valve.

In some embodiments, the native valve may be in a heart of a patient. The method may further comprise transseptally inserting the distal end of the delivery device into a left atrium of the heart. Alternatively, or in combination, the native valve may comprise a mitral valve, the first side of the native valve may comprise a left atrium, and the second side of the native valve may comprise a left ventricle.

In some embodiments, the native valve may be in a heart of a patient. The native valve may comprise an aortic valve, the first side of the native valve may comprise a left ventricle, and the second side of the native valve may comprise an aorta.

In some embodiments, the native valve may be in a heart of a patient. The native valve may comprise a tricuspid valve, the first side of the native valve may comprise a right atrium, and the second side of the native valve may comprise a right ventricle.

In another aspect, a system for treating a diseased native valve in a patient is provided. The system comprises a frame structure having a compressed configuration and an expanded configuration and an anchor comprising a main body having a curved shape and a free end disposed radially outward from the curved shape of the main body when the anchor is in a deployed configuration. The anchor is configured to be fully advanced from a first side of a native valve in a patient into a second side of the native valve and anchor the frame structure to the native valve when the frame structure is in the expanded configuration adjacent the native valve.

In some embodiments, the curved shape may be a generally tubular shape.

In some embodiments, the curved shape may be a generally frustoconical shape.

In some embodiments, the curved shape may be a generally cylindrical shape.

In some embodiments, the free end may be configured to be rotated around one or more structures on the second side of the native valve when the anchor in the deployed configuration is rotated.

In some embodiments, the free end may have a larger radius of curvature than a radius of curvature of the main body.

In another aspect, a system for treating a diseased native valve in a patient is provided. The system comprises a frame structure having a compressed configuration and an expanded configuration and an anchor comprising a wire having a free end. The anchor is configured to be fully advanced from a atrial side of a native valve in a patient into a ventricle of the heart and anchor the frame structure to the native valve when the frame structure is in the expanded configuration adjacent the native valve.

In some embodiments, the system further comprises a delivery device. The delivery device may comprise an outer sheath, an inner shaft disposed within a lumen of the outer sheath, and a guidewire disposed within a lumen of the inner shaft. A proximal end of the anchor may be detachably coupled to the inner shaft during delivery to the native valve. The outer sheath may be steerable.

In some embodiments, the anchor may comprise an elongated configuration and a deployed configuration. The anchor may be configured to be actuated from the elongated configuration to the deployed configuration adjacent the native valve. Retraction of the guidewire into the lumen of the inner shaft may actuate the anchor into the deployed configuration. Alternatively, or in combination, the anchor may be maintained in the elongated configuration by radial constriction from the outer sheath and advancement of the inner shaft out of the lumen of the outer sheath may actuate the anchor into the deployed configuration.

In some embodiments, the proximal end of the anchor may be detachably coupled to the inner shaft of the delivery device by radial constriction from the outer sheath. Retraction of the outer sheath away from the proximal end of the anchor may detach the anchor from the delivery device. Alternatively, or in combination, the proximal end of the anchor may be detachably coupled to the inner shaft of the delivery device by an attachment element. Alternatively, or in combination, the proximal end of the anchor may be detachably coupled to the inner shaft of the delivery device by a weak adhesive.

In some embodiments, the frame structure may be detachably coupled to the delivery device in the compressed configuration during delivery to the native valve. Expansion of the frame structure to the expanded configuration may detach the frame structure from the delivery device.

In some embodiments, the free end may comprise an atraumatic tip. For example, the free end may comprise a ball tip.

In some embodiments, the free end may be configured for piercing tissue.

In some embodiments, the wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having the same or different diameters. Alternatively, or in combination, the anchor may comprise at least two helical wires having the same or different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the helical wire may have a generally cylindrical shape. The free end of the helical wire may extend radially outward from the cylindrical shape.

In some embodiments, the frame structure may be configured for expanding within the native valve of the patient.

In some embodiments, the compressed configuration may be sized and dimensioned for percutaneous insertion and the expanded configuration may be sized and dimensioned for implantation in the native valve of the patient.

In some embodiments, the frame structure may comprise a first and second opposite ends, the first end extending above a native valve and the second end extending below the native valve when the frame structure is anchored to the native valve.

In some embodiments, the frame structure may sit below the native valve when the frame structure is anchored to the native valve.

In some embodiments, the frame structure may comprise an expandable stent.

In some embodiments, the expanded configuration may have a generally tubular expanded shape.

In some embodiments, the frame structure may comprise an expanded outer periphery in the expanded configuration and a compressed outer periphery when subject to an external radial force in the compressed configuration. The compressed outer periphery may be smaller in diameter than the expanded outer periphery.

In some embodiments, the frame structure may be balloon-expandable.

In some embodiments, the frame structure may be self-expanding.

In some embodiments, the frame structure may be maintained in the compressed configuration by radial constriction from the outer sheath of the delivery device. Advancement of the inner shaft out of the lumen of the outer sheath may actuate the frame structure into the expanded configuration.

In some embodiments, the system may further comprise a valve segment within the frame structure comprising a biocompatible one-way valve. At least a portion of the valve segment may be positioned within at least a portion of the frame structure. The valve segment may comprise at least one leaflet having an inner layer and an outer layer. The frame structure may be attached to the outer layer at one or more ends of the frame structure. The valve segment may comprise a plurality of leaflets.

In another aspect, a method for treating a diseased native valve in a patient is provided. The method comprises advancing a distal end of a delivery device from a first side of a native valve to a second side of the native valve, wherein the distal end of the delivery device is detachably coupled to an anchor and a frame structure, fully deploying the anchor on the second side of the native valve, releasing the anchor from the distal end of the delivery device, expanding the frame structure within the native valve from a compressed configuration to an expanded configuration, releasing the frame structure from the distal end of the delivery device, and retracting the delivery device from the native valve.

In some embodiments, the method may further comprise steering the distal end of the delivery device such that the distal end of the delivery device points towards the first side of the native valve.

In some embodiments, fully deploying the anchor may comprise actuating the anchor from an elongated configuration to a deployed configuration.

In some embodiments, fully deploying the anchor may comprise actuating the anchor from an elongated configuration to a deployed configuration on the first side of the native valve and advancing the anchor in the deployed configuration through the native valve to the second side of the native valve. Advancing the anchor may comprise pushing the anchor through the native valve. Advancing the anchor may further comprise rotating the anchor through the native valve.

In some embodiments, fully deploying the anchor may comprise positioning the anchor such that it is located only on the second side of the native valve.

In some embodiments, the frame structure may comprise a first and second opposite ends. Expanding the frame structure may comprise expanding the frame structure such that the first end extends above the first side of the native valve and the second end extends below second side of the native valve.

In some embodiments, expanding the frame structure may comprise expanding at least a portion the frame structure within at least a portion of the deployed anchor to anchor the frame structure to the native valve.

In some embodiments, expanding the frame structure and releasing the frame structure may occur simultaneously.

In some embodiments, the frame structure may be balloon-expandable. Expanding the frame structure may comprise inflating a balloon disposed within the frame structure. Inflation of the balloon may cause expansion of the frame structure.

In some embodiments, the frame structure may be self-expanding. Expanding the frame structure may comprise releasing the frame structure from radial constriction by the delivery device.

In some embodiments, the anchor may comprise a wire having a free end. The method may further comprise rotating the free end of the deployed anchor around one or more structures on the second side of the native valve. The one or more structures may comprise one or more valve leaflets of the native valve. Alternatively, or in combination, the one or more structures may comprise one or more chordae of the left ventricle.

In some embodiments, the free end of the wire may comprise an atraumatic tip. For example, the free end may comprise a ball tip.

In some embodiments, the free end of the wire may be configured for piercing tissue.

In some embodiments, the wire may comprise a helical wire. Optionally, the anchor may comprise a first portion comprising the helical wire and another portion. Alternatively, or in combination, the anchor may comprise a plurality of helical wires. For example, the anchor may comprise at least two helical wires having the same or different diameters. Alternatively, or in combination, the anchor may comprise at least two helical wires having the same or different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the helical wire may have a generally cylindrical shape. The free end of the helical wire may extend radially outward from the cylindrical shape.

In some embodiments, the frame structure may further comprise a valve segment within the frame structure comprising a biocompatible one-way valve.

In some embodiments, the native valve may be in a heart of a patient. The method may further comprise transseptally inserting the distal end of the delivery device into a left atrium of the heart. Alternatively, or in combination, the native valve may comprise a mitral valve, the first side of the native valve may comprise a left atrium, and the second side of the native valve may comprise a left ventricle.

In another aspect, a method for treating a diseased native valve in a patient is provided. The method comprises advancing a distal end of a delivery device from a first side of a native valve to a second side of the native valve, wherein the distal end of the delivery device is detachably coupled to an anchor and a frame structure, wherein the anchor comprises the free end adjacent a proximal portion of the frame structure and a second end coupled to a distal portion of the frame structure, and wherein advancing the distal end of the delivery device advances the anchor from the first side of the native valve to the second side of the native valve and positions the free end of the anchor on the second side of the native valve; deploying the anchor from a delivery configuration to a deployed configuration; rotating the free end of the anchor in the deployed configuration around one or more structures on the second side of the native valve; releasing the anchor from the distal end of the delivery device; expanding the frame structure within the native valve from a compressed configuration to an expanded configuration; releasing the frame structure from the distal end of the delivery device; and retracting the delivery device from the native valve.

In some embodiments, the anchor may be deployed from the delivery configuration to the deployed configuration on the first side of the native valve.

In some embodiments, the method may further comprise positioning the anchor such that it is located only on the second side of the native valve after advancing the distal end of the delivery device from the first side of the native valve to the second side of the native valve.

In some embodiments, rotating the free end of the anchor around the one or more structures may comprise rotating the anchor upwards towards the native valve.

In another aspect, a method for treating a diseased native valve in a patient is provided. The method comprises advancing a distal end of a delivery device from a first side of a native valve to a second side of the native valve, wherein the distal end of the delivery device is detachably coupled to an anchor and a frame structure; deploying the anchor from a delivery configuration to a deployed configuration; positioning the anchor such that it is located only on the second side of the native valve after advancing the distal end of the delivery device from the first side of the native valve to the second side of the native valve; releasing the anchor from the distal end of the delivery device; expanding the frame structure within the native valve from a compressed configuration to an expanded configuration; releasing the frame structure from the distal end of the delivery device; and retracting the delivery device from the native valve.

In some embodiments, the anchor may be deployed from the delivery configuration to the deployed configuration on the first side of the native valve.

In some embodiments, the method may further comprise, after the anchor has been deployed into the deployed configuration, rotating a free end of the anchor in the deployed configuration around one or more structures on the second side of the native valve.

In another aspect, a heart valve prosthesis for replacing a diseased native valve in a heart of a patient is provided. The valve prosthesis comprises a compressible and expandable frame structure, a valve segment disposed within the frame structure, the valve segment comprising a biocompatible one-way valve, and an anchor connected to an outer periphery of the frame structure, wherein the anchor comprises a helical wire having a free end.

In some embodiments, the free end of the helical wire may be configured to guide the helical wire through a commissure of a native valve of a patient.

In some embodiments, the free end may comprise an atraumatic tip. For example, the free end may comprise a ball tip.

In some embodiments, the free end may be configured for piercing tissue.

In some embodiments, the anchor may comprise a first portion comprising the helical wire and another portion.

In some embodiments, the anchor may comprise a plurality of anchors. The plurality of anchors may comprise at least two helical wires having different diameters. Alternatively, or in combination, the plurality of anchors may comprise at least two helical wires having different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the frame structure may be configured for expanding within a native valve of a patient.

In some embodiments, the frame structure may have a compressed state sized and dimensioned for percutaneous insertion and an expanded state sized and dimensioned for implantation in a native valve of a patient.

In some embodiments, the frame structure may comprise first and second opposite ends, the first end extending above a native valve and the second end extending below the native valve when the valve prosthesis is positioned across the native valve.

In some embodiments, the frame structure may comprise an expandable stent.

In some embodiments, the frame structure may comprise a generally tubular expanded shape.

In some embodiments, the frame structure may comprise an expanded outer periphery and a compressed outer periphery when subject to an external radial force. The compressed outer periphery may be slightly smaller in diameter than the expanded outer periphery.

In some embodiments, the frame structure may be balloon-expandable.

In some embodiments, the frame structure may be self-expanding.

In some embodiments, at least a portion of the valve segment may be positioned within at least a portion of the frame structure.

In some embodiments, the valve segment may comprise at least one leaflet having an inner layer and an outer layer. The frame structure may be attached to the outer layer at one or more ends of the frame structure.

In some embodiments, the valve segment may comprise a plurality of leaflets. For example, the valve segment may comprise two leaflets.

In another aspect, a method of replacing a diseased native valve of a patient is provided. The method comprises loading a valve prosthesis into a delivery catheter, the valve prosthesis comprising an expandable frame structure carrying a biocompatible valve segment and an anchor attached to an outer periphery of the frame structure, the anchor comprising a wire having a free end; delivering the valve prosthesis to a target location above a native valve; inserting the valve prosthesis through the native valve to a position posterior the native valve; rotating the wire such that the free end wraps around at least a portion of chordae tendineae below the valve; and expanding the frame structure including the valve segment within the native valve.

In some embodiments, the method may further comprise anchoring the valve prosthesis by rotating the wire until the frame structure is positioned within leaflets of the native valve.

In some embodiments, the method may further comprise anchoring the valve prosthesis by rotating the wire until the wire tightens around the chordae tendineae.

In some embodiments, the frame structure may be balloon-expandable. Expanding the frame structure may comprise expanding a balloon within the frame structure.

In some embodiments, the frame structure may be self-expanding. Expanding the frame structure may comprise removing a sheath of the delivery device from the frame structure.

In another aspect, a method of replacing a diseased native valve of a patient is provided. The method comprises loading a valve prosthesis into a delivery catheter, the valve prosthesis comprising an expandable frame structure carrying a biocompatible valve segment and an anchor attached to an outer periphery of the frame structure; delivering the valve prosthesis to a target location above a native valve; inserting the valve prosthesis through the native valve to a position posterior the native valve; anchoring the valve prosthesis to native leaflets and/or chordae; and expanding the frame structure including the valve segment within the native valve.

In some embodiments, anchoring may comprise rotating the anchor to engage the native valve leaflets and/or chordae.

In some embodiments, the anchor may comprise a helical wire and anchoring may comprise rotating helical wire such that the wire wraps around the native valve leaflets and/or chordae tendineae.

In another aspect, a heart valve prosthesis for replacing a diseased native valve in a patient is provided. The valve includes a compressible and expandable frame structure and an anchor connected to an outer periphery of the frame structure. The anchor comprises a helical wire having a free end. The valve may further include a valve segment within the frame structure. The valve segment may include a biocompatible one-way valve.

In another aspect, a method of implanting a prosthetic valve to treat a diseased native valve is provided.

In another aspect, valve comprising any of the features described herein in any combination thereof is provided.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 31 is a perspective view. FIG. 32 is a front view. FIG. 33 is a back view. FIG. 34 is a top view. FIG. 35 is an enlarged view of a bottom portion of the device, showing attachment of the anchor to the frame structure.

FIGS. 36 and 37 are perspective views. FIG. 38 is a front view. FIG. 39 is a top view.

FIGS. 40-42 are front views of valve devices similar to the one of FIG. 6, illustrating different anchors, in accordance with embodiments.

FIG. 44 is a front view of the device. FIG. 45 is a perspective top view. FIG. 46 is a bottom view. FIG. 47 is a perspective view. FIG. 48 is a perspective view of the valve device loaded on a delivery catheter. FIG. 49 is a bottom view of the device loaded on a delivery catheter.

DETAILED DESCRIPTION

Figure 1:
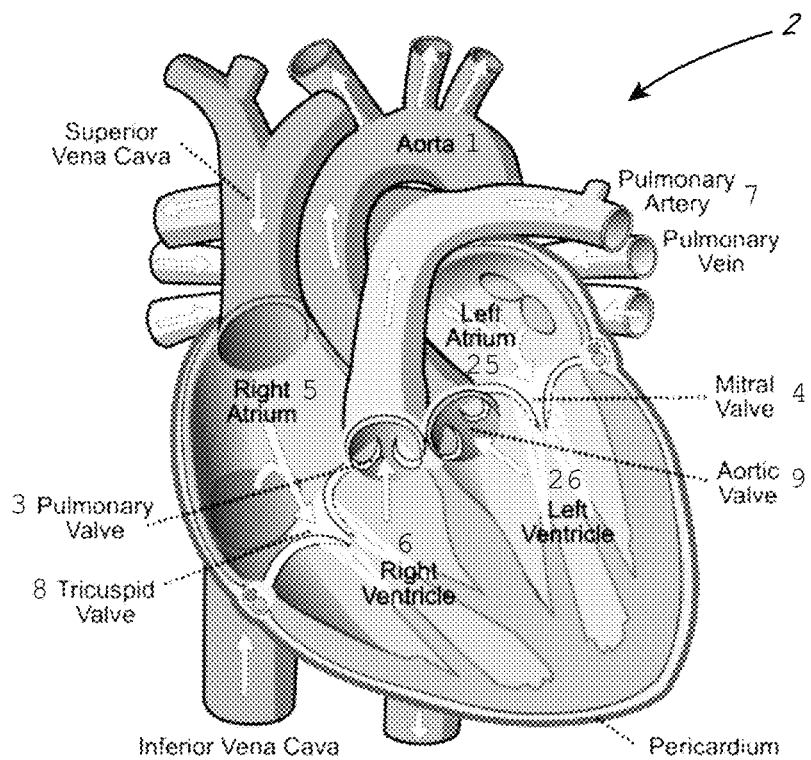
FIG. 1 is a schematic of a human heart illustrating the path of blood flow through the heart.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

For convenience in explanation and accurate definition in the appended claims, the terms "up" or "upper", "down" or "lower", "inside" and "outside" are used to describe features of the present disclosure with reference to the positions of such features as displayed in the figures.

In many respects the modifications of the various figures resemble those of preceding modifications and the same reference numerals followed by subscripts "a", "b", "c", and "d" designate corresponding parts. It will be understood by one of ordinary skill in the art that modifications of corresponding parts of the various figures are interchangeable with one another between embodiments to arrive at multiple combinations with multiple modified parts.

The present disclosure is described in relation to deployment of systems, devices, or methods for treatment of a diseased native valve of the heart, for example a mitral valve, aortic valve, or tricuspid valve. However, one of skill in the art will appreciate that this is not intended to be limiting and the devices and methods disclosed herein may be used in other anatomical areas and in other surgical procedures.

Figure 2:
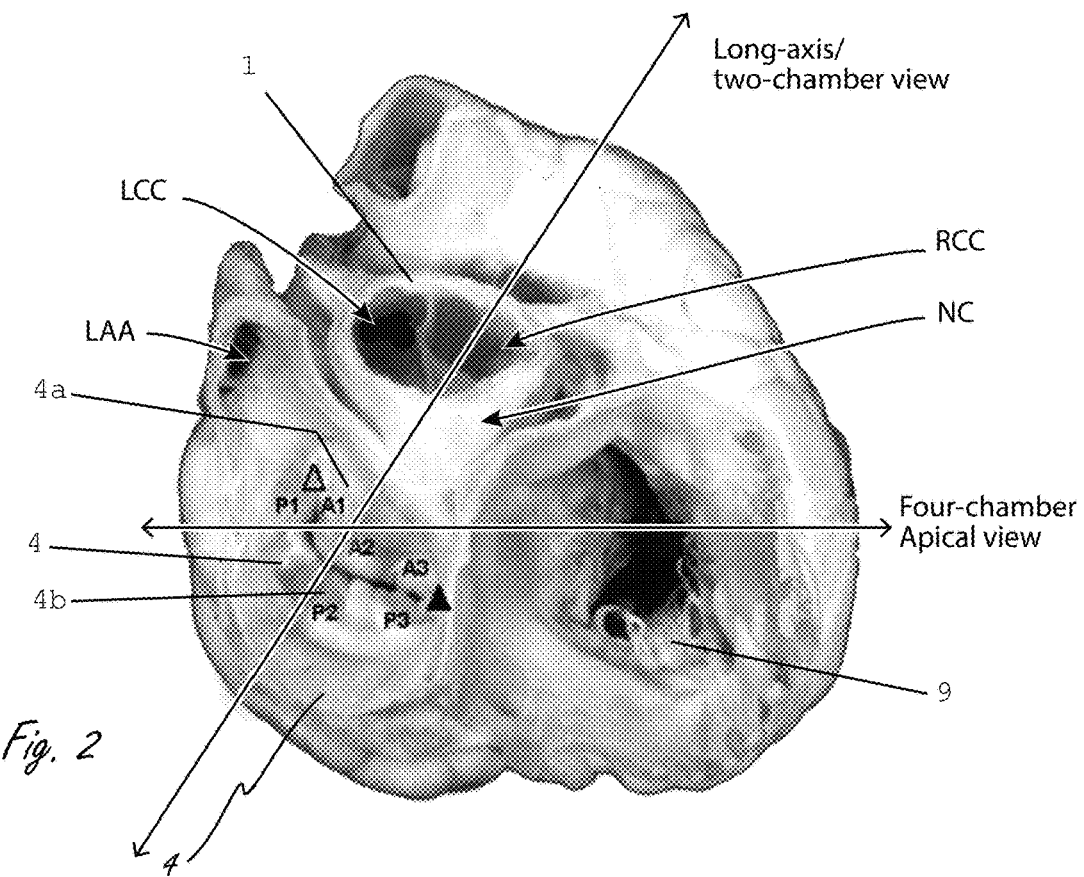
FIG. 2 is a cross-sectional view of a heart looking down through the mitral valve, aortic valve, and aorta.
Figure 3:
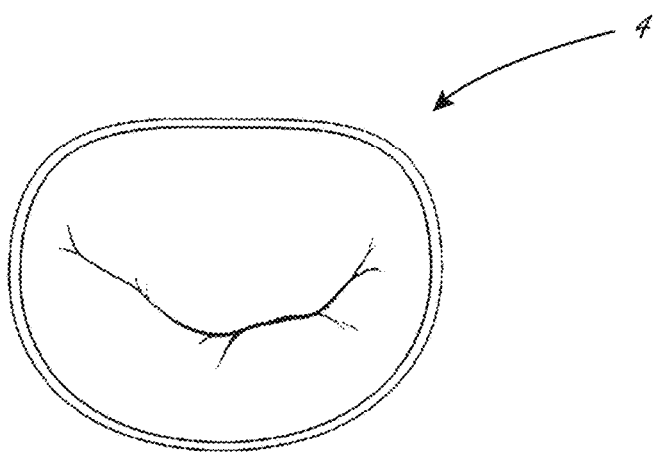
FIG. 3 is a schematic of a healthy mitral valve.

Turning now to the drawings, wherein like components are designated by like reference numerals throughout the various figures, attention is directed to FIGS. 1-5. FIG. 1 shows a human heart 2 and the blood flow pathways through the four chambers of the heart. FIG. 2 is a human heart 2 showing the mitral valve 4, aortic valve 9, and aorta 1. The mitral valve 4 includes two leaflets 4a, 4b. The anterior (aortic) leaflet 4a is adjacent the aorta 1. The posterior (mural) leaflet 4b is remote from the aorta 1. The aortic valve 9 includes three leaflets. In the current view, the heart 2 is in systole with the aortic valve 9 open and the mitral valve 4 closed. Whereas FIG. 1 illustrates a healthy heart 2, FIGS. 2-5 illustrate exemplary mitral valve 4 disease states which may be addressed by the prosthetic valve in accordance with the present disclosure. The prosthetic valve may also be used to treat functional regurgitation such as functional mitral regurgitation (FMR).

FIGS. 6-18 show an exemplary valve prosthesis 10 (also referred to herein as "valve device") for replacement of a diseased mitral valve in accordance with the present disclosure. The illustrated valve prosthesis 10 comprises a frame structure 12, a valve segment 14, and an anchor 15. FIGS. 6-10 show the valve prosthesis 10 in an expanded, deployed state. FIGS. 12-18 show the frame structure 12 without the valve segment 14. The frame structure 12 is in a collapsed state in FIGS. 12-15 and an expanded state in FIGS. 16-18. The anchor 15 is shown in a deployed state.

The exemplary valve prosthesis 10 will now be described with reference to FIGS. 6-11. In the illustrated embodiment, valve prosthesis 10 is configured for replacement of a native mitral valve. Valve 10 includes a frame structure 12, valve segment 14, and anchor 15. In the illustrated embodiment, the anchor 15 includes a wire 20 formed in a helical or spiral shape around the frame structure.

The exemplary frame structure 12 is configured like a stent. The frame structure 12 has an expanded state and an unexpanded (e.g., collapsed or compressed) state. The compressed state is sized and dimensioned for percutaneous insertion and the expanded state sized and dimensioned for implantation in a native valve of a patient. In various embodiments, the frame structure 12 comprises an expanded outer periphery and a compressed outer periphery when subject to an external radial force, the compressed outer periphery being slightly smaller in diameter than the expanded outer periphery. The frame structure 12 is shown in the expanded, deployed state in FIG. 6. The frame structure 12 is shown in the collapsed, delivery state in FIG. 12.

The exemplary frame structure 12 is a scaffold in a diamond pattern formed from a shape memory material (e.g. NiTi). One of ordinary skill in the art will appreciate from the description herein that many other structures, materials, and configurations may be employed for the frame structure 12. For example, the frame structure 12 may be formed of a polymer of sufficient elasticity. The frame structure 12 may be formed of a combination of a metal and polymer, such as a metal (e.g., shape memory material) covered in polymer. The frame structure 12 may include a variety of patterns besides diamond shapes.

Valve prosthesis 10 includes a valve segment 14 within the frame structure 12. The exemplary valve segment 14 is expandable and collapsible. In the illustrated embodiment, the valve segment 14 is affixed within the frame structure 12 and expands and collapses with the frame structure 12. Valve segment is used somewhat interchangeably with prosthetic valve leaflet and generally refers to the prosthetic leaflets and frame. As used herein, "prosthetic valve" may refer to all manner of prosthetic and artificial replacement valves including tissue (biological) valves, tissue-engineered valves, polymer valves (e.g. biodegradable polymer valves), and even certain mechanical valves.

In the illustrated embodiment, frame structure 12 is a closed frame such that blood flow is forced through valve segment 14 therein. One or more skirts and/or seals may help force blood through valve segment 14.

Figure 11:
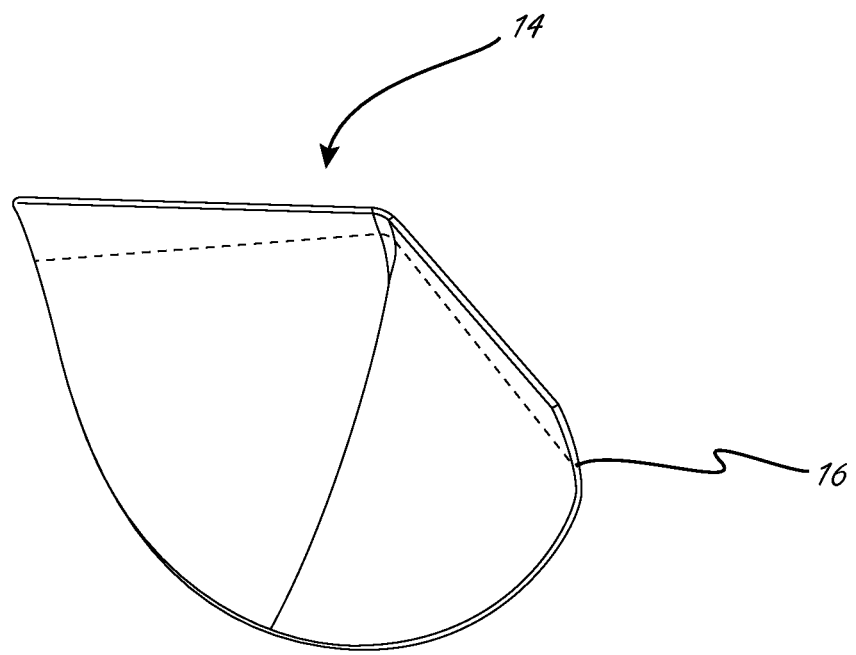
FIG. 11 is a perspective view of the prosthetic valve leaflet of the valve of FIG. 6, in accordance with embodiments.
Figure 12:
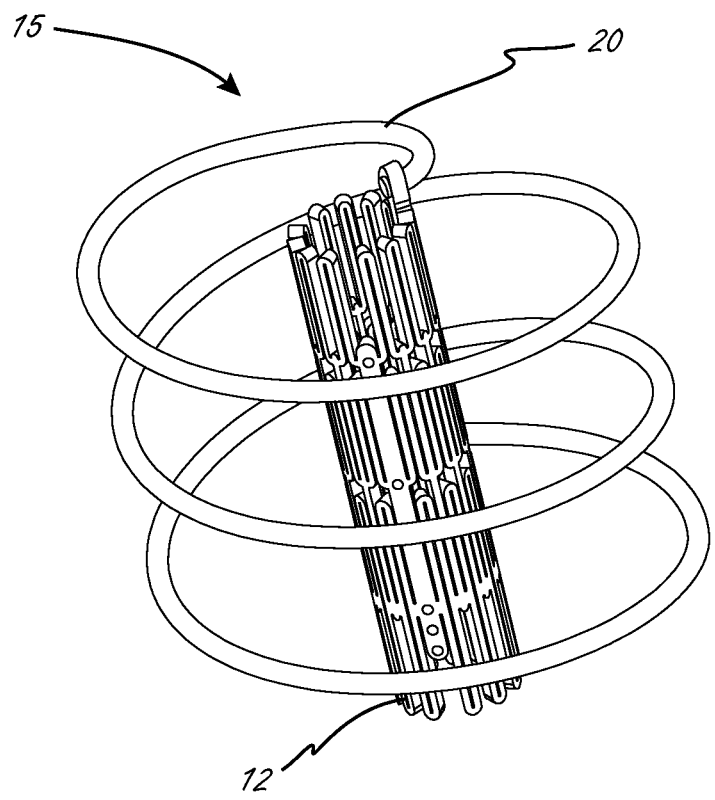
FIGS. 12-18 are several views of the frame structure of the valve of FIG. 6, in accordance with embodiments.
Figure 13:
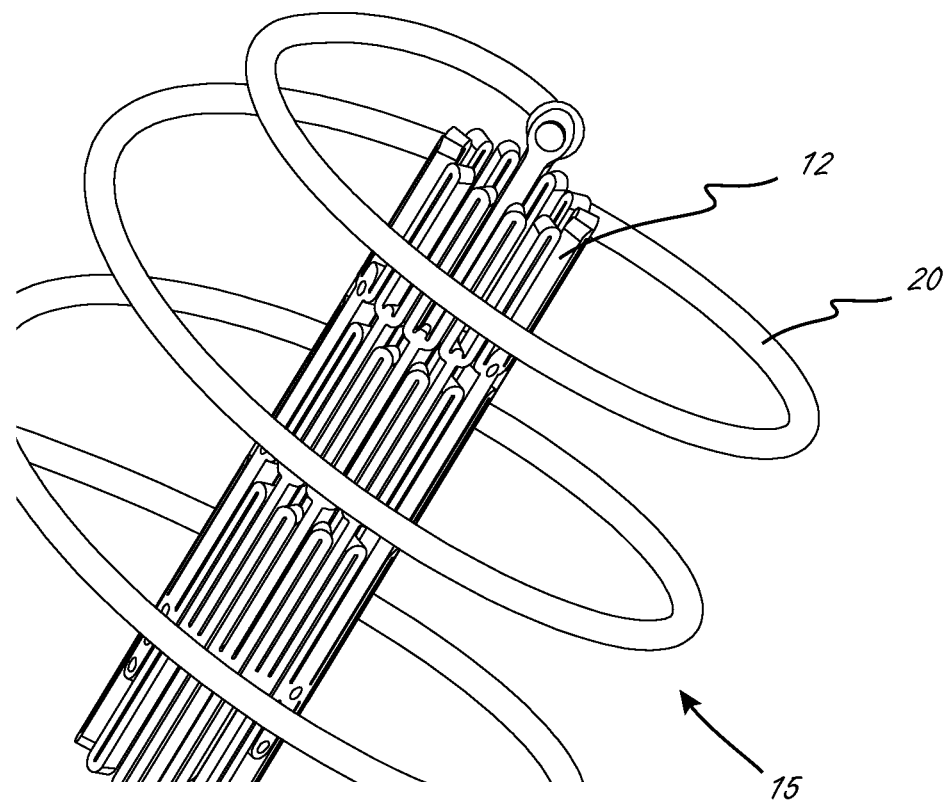
Figure 14:
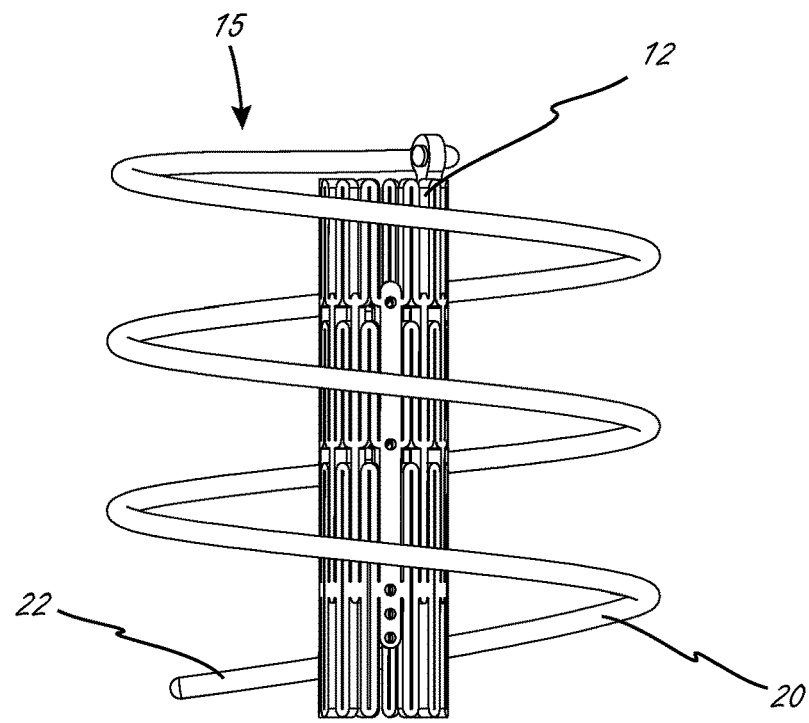
Figure 15:
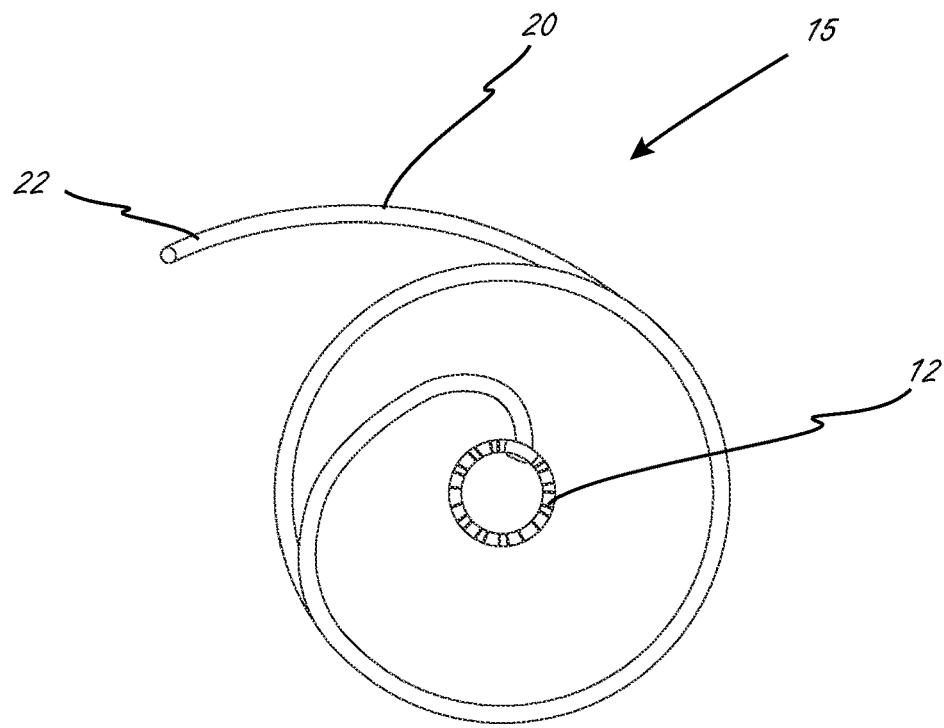
Figure 16:
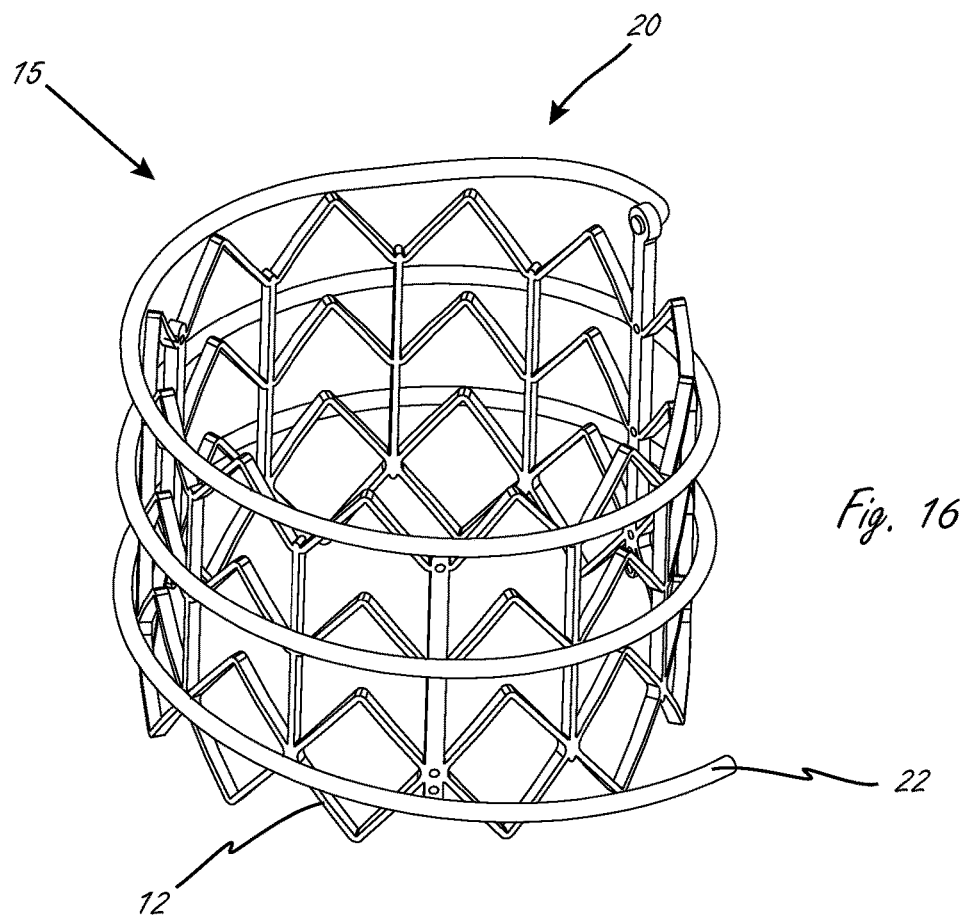
Figure 17:
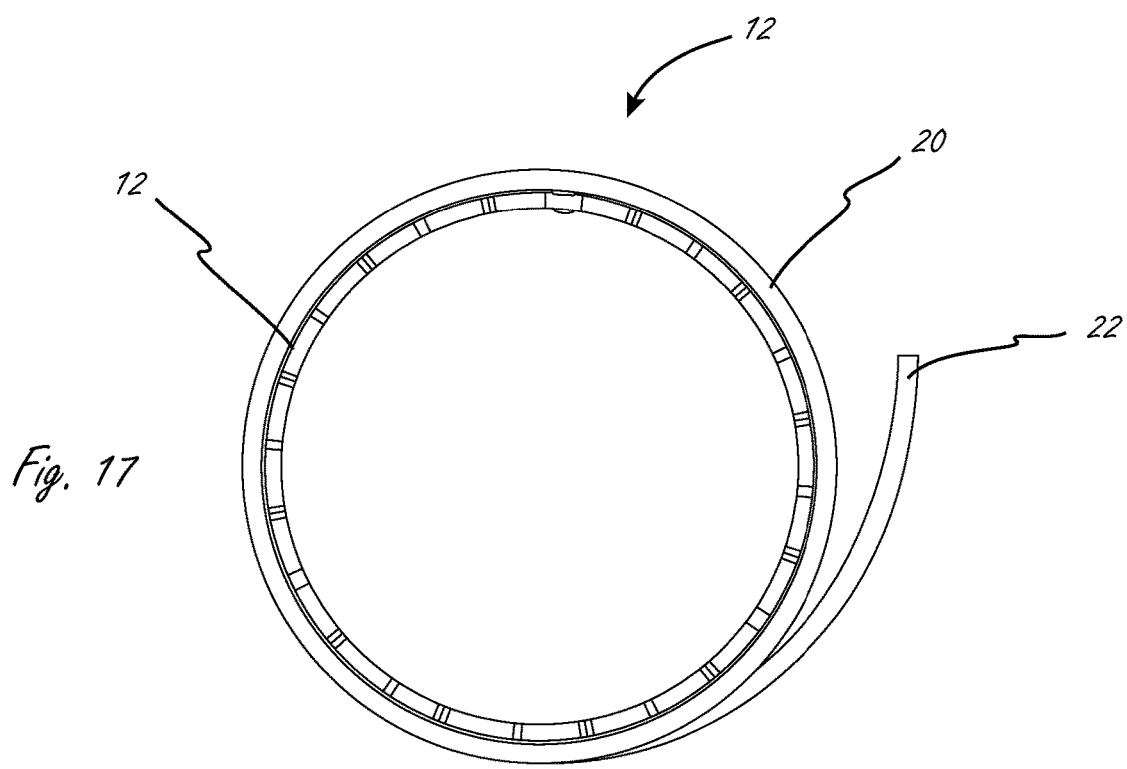
Figure 18:
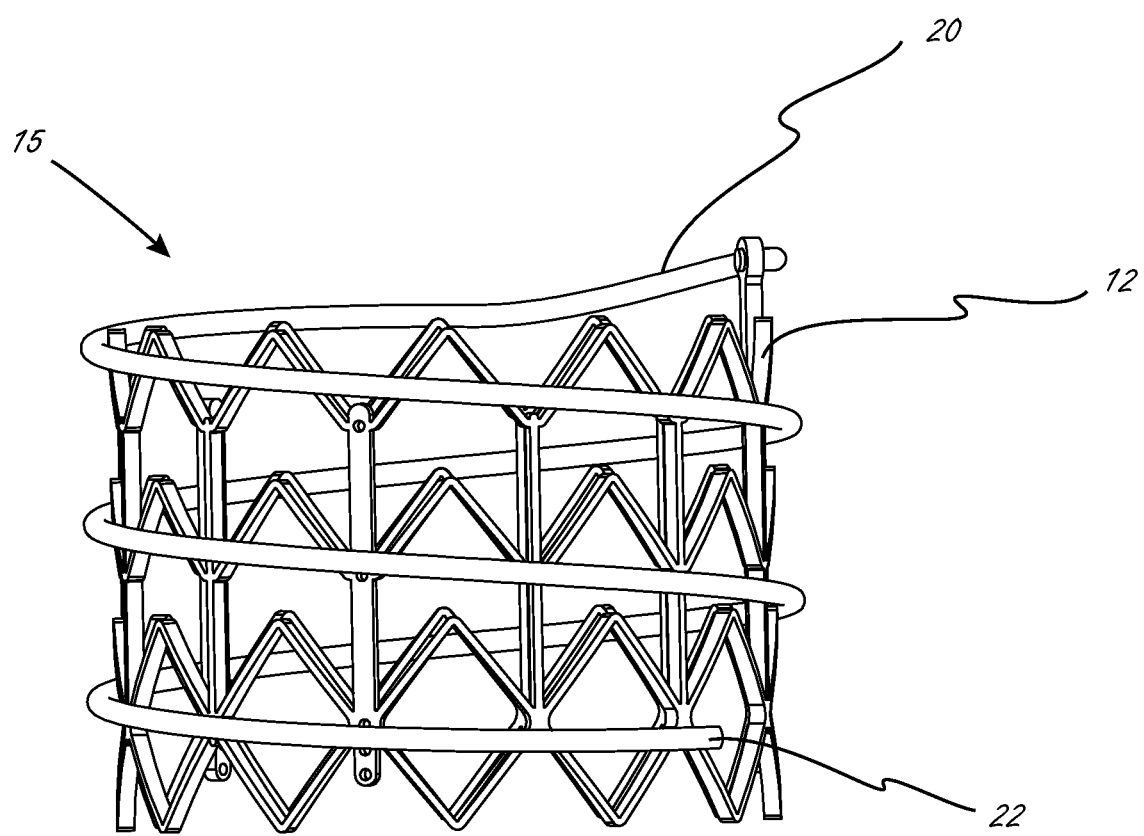

Valve segment 14 can be configured as would be understood by one of skill from the description herein. The valve segment 14 can be similar to existing transcatheter valves. The valve segment 14 can be similar to existing surgical tissue valves, and mechanical valves. In various embodiments, the valve segment 14 includes leaflets 16 formed of multi-layered materials for preferential function. At least one leaflet 16 may have an inner layer and an outer layer. In various embodiments, the leaflet 16 is connected to a valve structure which in turn is connected to the frame structure 12. The valve structure may be connected to the frame structure 12 before or after the frame structure 12 has been deployed adjacent a native valve. In various embodiments, the leaflet 16 is attached to the frame structure 12 directly. The leaflet 16 may have an inner layer and an outer layer, with the outer layer attached to the frame structure 12. The leaflet 16 may be attached to an end of the frame structure 12. Alternatively, or in combination, the leaflet 16 may be attached to an intermediate portion of the frame structure 12. In various embodiments, the valve segment 14 includes a plurality of leaflets 16, such as two, three, or more leaflets. In the illustrated embodiment, the valve segment 14 includes three leaflets 16 which are attached to frame structure 12. An exemplary leaflet 16 is shown in FIG. 11. The leaflet 16 is concave to permit flow in one direction. In particular, flow in one direction causes the leaflet(s) 16 to deflect open and flow in the opposite direction causes the leaflet(s) 16 to close.

Turning back to FIGS. 6-18, and more particularly FIGS. 12-18, an exemplary anchor 15 comprises a helical member, such as wire 20, having a free end 22. The other end of the wire 20 is attached to a top end of frame structure 12. In the illustrated embodiment, one end of the wire 20 is fixed to a strut of the frame structure 12. This end can be attached by suitable means as would be understood by one of skill in the art from the description herein including, but not limited to, a weld, an adhesive, and a mechanical fastener. In various embodiments, the helical wire 20 is attached to the frame structure only at the location of the second end.

Although referred to as an anchor, one will appreciate that anchor 15 does not require performing an anchor function in the traditional sense. As will be described in more detail below, the anchor guides valve prosthesis 10 into a desired position within a native valve. The anchor 15 may also mitigate against undesired entanglement and disturbances to the chordae tendineae and valve leaflets of the mitral valve.

Wire 20 is formed of a material having sufficient rigidity to hold a predetermined shape. In the exemplary embodiment, the wire 20 is formed of a shape memory material (e.g. NiTi). It may be desirable for at least an end portion to be relatively rigid such that it can exert a force to move chordae tendineae, while still retaining flexibility to be collapsed within a catheter. In various embodiments, the end portion (including free end 22) only needs sufficient rigidity to hold its shape and will deform under a load. For example, the end portion may be configured with similar rigidity to a guidewire, or slightly stiffer.

In various embodiments, the anchor 15 comprises a helical member. The helical member may comprise a helical wire or flat ribbon. The helical member may comprise a three-dimensional surface as described herein.

In various embodiments, the anchor 15 may comprise a first portion comprising the helical wire 20 and another portion. Alternatively, or in combination, the anchor 15 may comprise a plurality of helical wires 20. For example, the anchor 15 may comprise at least two helical wires 20 having the same or different diameters. Alternatively, or in combination, the anchor 15 may comprise at least two helical wires 20 having the same or different winding pitches.

In various embodiments, the anchor 15 may comprise a plurality of anchors, for example a plurality of helical wires 20 as described herein.

Figure 4:
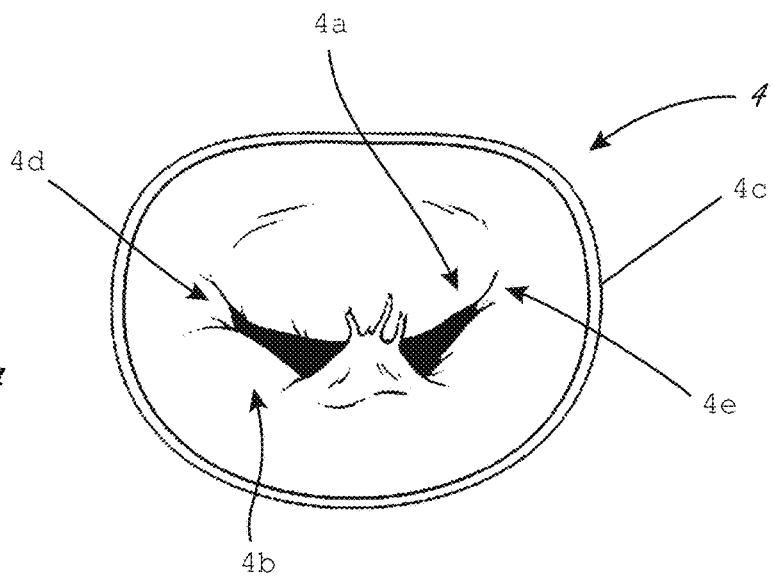
FIGS. 4 and 5 are schematics of diseased mitral valves.
Figure 5:
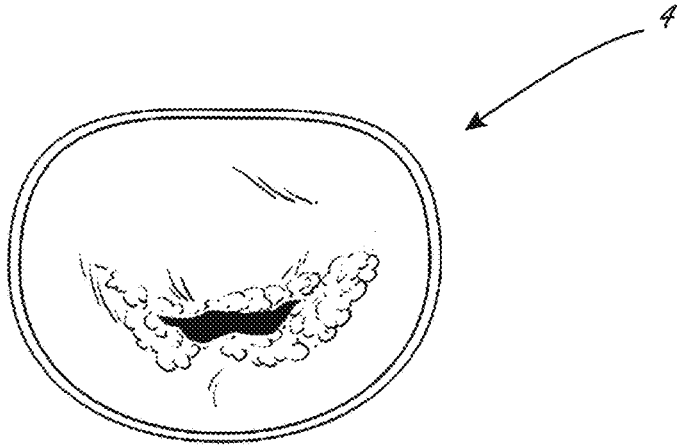

In the illustrated embodiment, valve prosthesis 10 is configured for replacing a mitral valve and free end 22 is configured for insertion through a commissure. FIG. 1 is a schematic of a human heart 2 having a mitral valve 4. FIGS. 2 and 4 show an exemplary mitral valve 4. As can be seen in the figures, several commissure points (anterolateral commissure 4d and posteromedial commissure 4e) are presented at the ends of the valve leaflets 4a, 4b.

With continued reference to FIGS. 6-18, the exemplary free end 22 is sized and dimensioned for insertion through one of the commissures. In the various embodiments, the free end 22 is configured to be atraumatic to avoid risk of injury to the valve tissue and leaflets. The free end 22 may be in the form of a blunt end, a ball tip, a curved tip (e.g., J-tip or pigtail), and other atraumatic shapes. In various embodiments, the free end 22 is configured with a sharp end to pierce tissue.

In various embodiments, wire 20 has varying stiffness along its length. The wire 20 may have two or more segments of differing stiffness and/or the stiffness may transition over its length. In various embodiments, wire 20 is attached to frame 12 at multiple points such that free end 22 is relatively flexible and the wire 20 is more rigid along portions where it is attached to the frame structure 12.

In various embodiments, free end 22 extends radially outward from frame structure 12, and in particular the remainder of wire 20. As will be described below, the free end 22 is configured to encircle a larger radius than the main coils of the wire 20. When the main coils of wire 20 have a generally curved shape (e.g., helical, tubular, frustoconoical, etc.), the free end 22 may extend radially outward from the curved shape. For example, when the main coils of wire 20 have a generally tubular shape, the free end 22 may extend radially outward from the tubular shape. When the main coils of wire 20 have a generally helical shape, the free end 22 may extend radially outward from the helical shape. When the main coils of wire 20 have a generally frustoconical shape, the free end 22 may extend radially outward from the frustoconical shape. The larger diameter facilitates capturing of the valve leaflets and/or chordae tendineae within the sweep of the free end 22 during rotation as will be described in more detail below.

A method of implanting valve prosthesis 10 in accordance with the present disclosure will now be described with reference to FIGS. 19-28. Although shown and described with respect to a mitral valve, one of ordinary skill in the art will understand that the principles described herein may be applied equally to other atrioventricular valves. Aspects of the procedure, delivery tool, and implanted valve prosthesis are similar to those described in U.S. Pat. Nos. 9,034,032; 9,005,273; 8,323,336; 8,075,615; 7,621,948; and 7,175,656 and U.S. Pub. No. 2011/0288637, which are incorporated herein for all purposes in their entirety.

Figure 19:
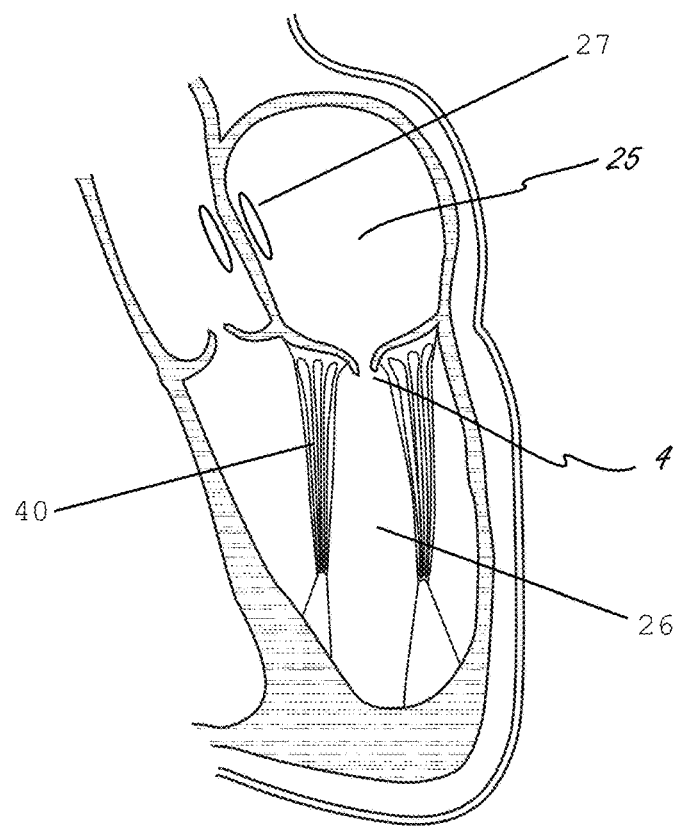
FIGS. 19-26 are several views of the method of implanting the valve of FIG. 6, in accordance with embodiments.

Prior to implantation, valve prosthesis 10 may be collapsed and loaded into a delivery device 30, for example, a delivery catheter. The valve system may optionally be primed before or after loading into the delivery catheter 30. FIG. 19 shows a cross-sectional side view of a heart 2 with a transseptal puncture 27 in the atrial septum thereof. The leaflets 42 of valve 4 do not fully prolapse and the patient is experiencing regurgitation.

Figure 20:
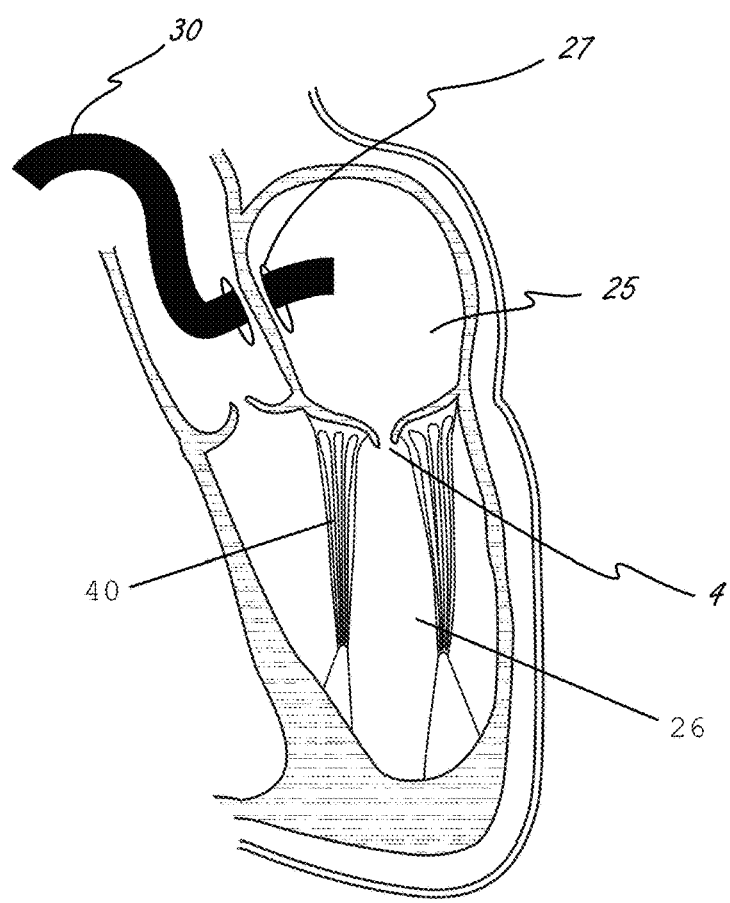

Next, the delivery catheter 30 is inserted through an introducer into a vessel. The delivery catheter 30 can be guided over a guidewire to a target location using the Seldinger technique. In the illustrated embodiment, the delivery catheter 30 is guided to the left atrium 25 through a transseptal puncture 27 in conventional fasion as shown in FIG. 20.

Figure 21:
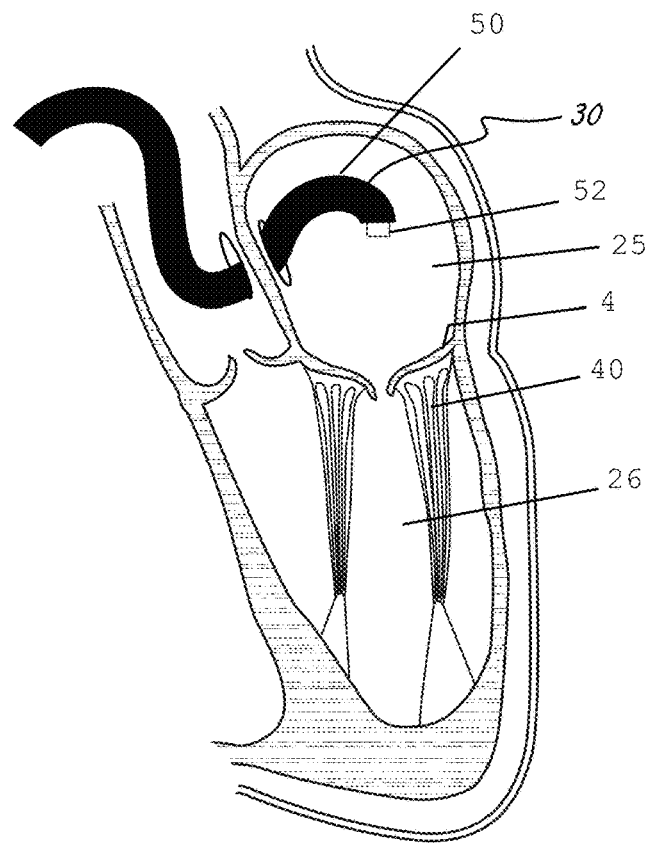
Figure 22:
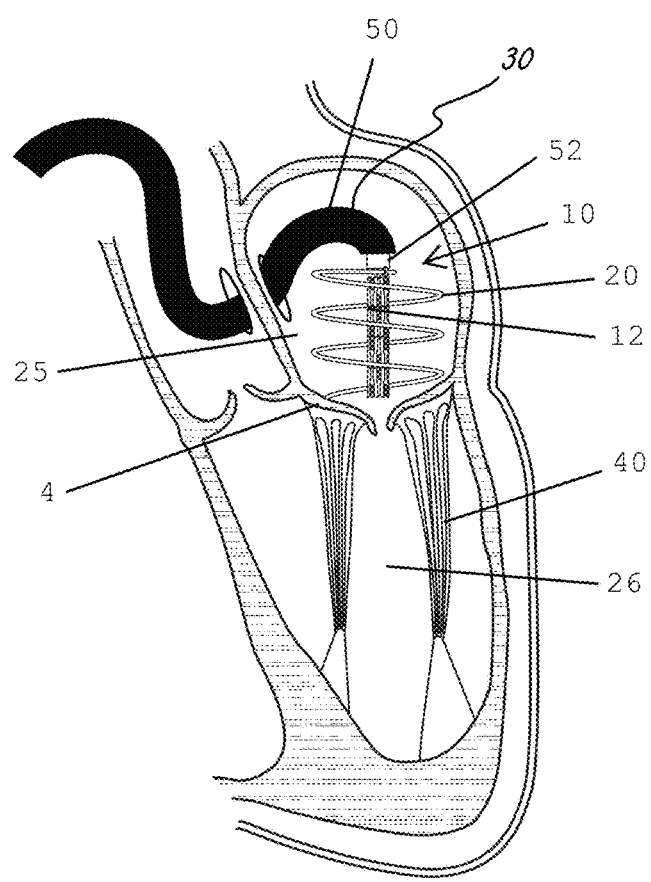

Turning to FIGS. 21-22, at this point, the end of the delivery catheter 30 is pointed towards the mitral valve 4. Valve prosthesis 10 is then pushed out of the distal end of delivery catheter 30. The delivery device 30 may comprise an outer catheter 50 and an inner catheter or shaft 52. In some embodiments, once the delivery device 30 is in position, the delivery tube 52 extends out of the outer catheter 50 to move valve device 10 distally towards the native valve 4. As the valve prosthesis 10 comes out from the delivery catheter 30, an anchor 15, such as wire 20, is deployed (e.g., from a straightened shape within the delivery device 30) to its pre-formed deployed shape and wraps around frame 12, which remains in its collapsed state as shown in FIG. 22. The valve prosthesis 10 is then aligned with the target native valve 4 so the axis of the prosthetic valve 10 is aligned with a central axis of the native valve 4.

Figure 23:
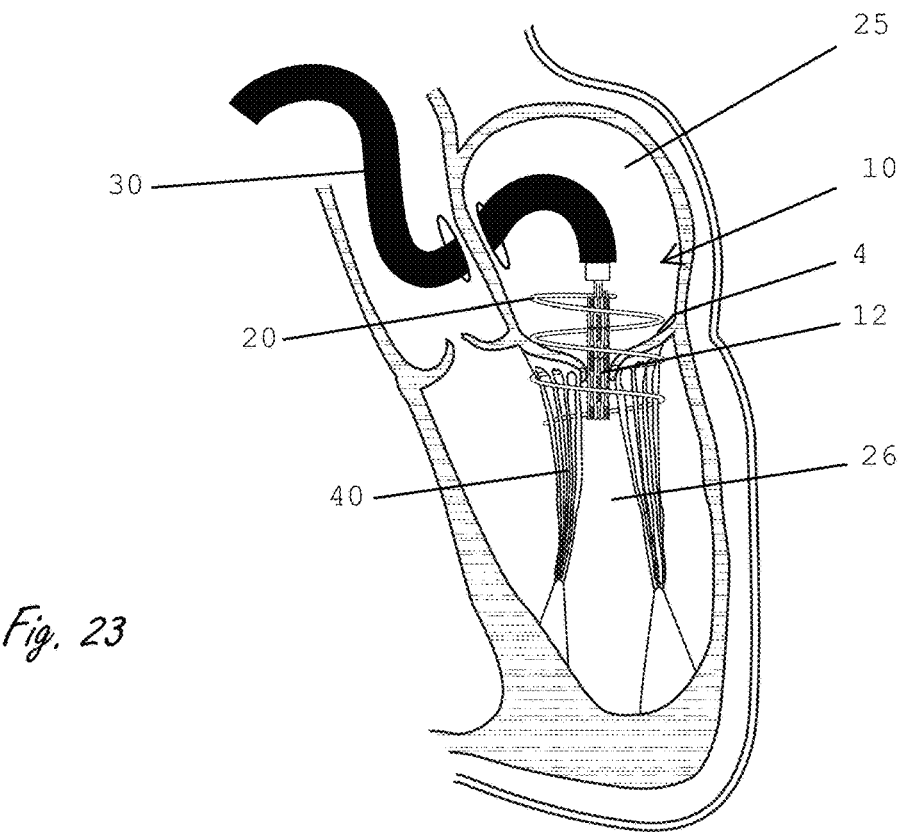
Figure 24:
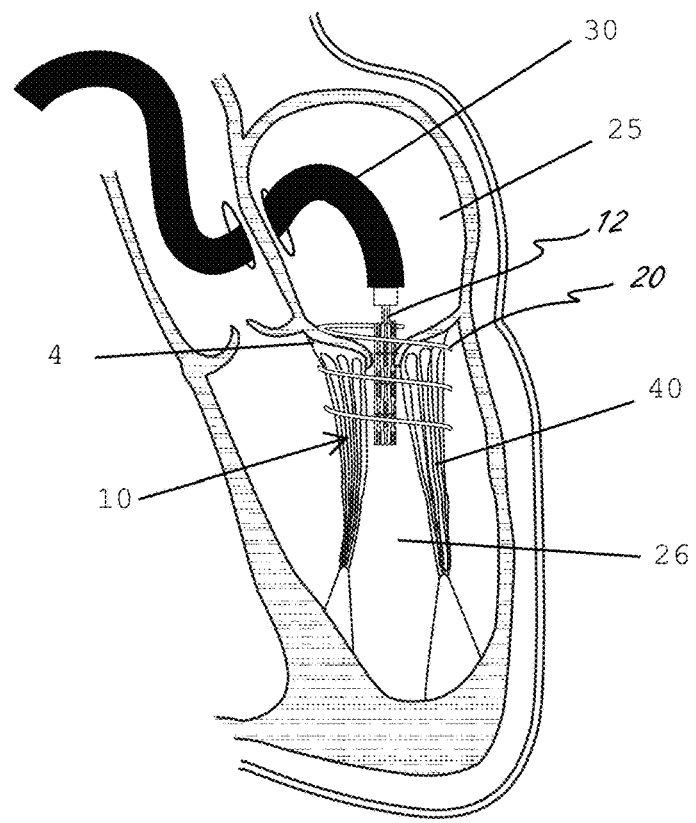

Turning to FIGS. 23-24, valve 10 is anchored to the native valve 4 using exemplary helical wire 20. The valve prosthesis 10—frame 12, wire 20, and valve segment 14—are slowly rotated into the native mitral valve 4. In the illustrated embodiment, a torquer is provided in the delivery catheter 30 for rotating valve 10. Free end 22 of wire 20 is rotated through a commissure and extends below the native valve 4 annulus. The valve prosthesis 4 is further rotated so the free end 22 captures the chordae tendineae (also referred to as "papillary muscles") 40 and/or native valve leaflets 42. As the wire 20 is continually rotated, the chordae tendineae 40 are gathered and pulled radially inward. Free end 22 has a larger radius than the main body of the helical coil (e.g., is disposed radially outward of the main body of the helical coil) in order to facilitate capture of the chordae tendineae 40 during rotation of the valve prosthesis 10. Frame structure 12 also moves into the native valve 4 as the wire 20 is rotated. Valve prosthesis 10 is in the correct position when the chordae tendineae 40 have been captured to a sufficient degree and/or frame structure 12 is in the desired location in the native valve 40. Insertion of the device through the native valve may be facilitated by the natural opening and closing of the native valve during the cardiac cycle. In the illustrated embodiment, the chordae tendineae 40 are pulled inwardly into a bunches (best seen in FIG. 25). The native valve leaflets 42 are also in communication with the helical coil 20. At this stage valve device 10 is rigidly anchored adjacent the native valve 40 annulus.

If the clinician desires to remove or reposition the valve, the helical wire 20 can be counter-rotated to back out the device 10 from the native valve 4. The implant rotation procedure can then be repeated.

Figure 25:
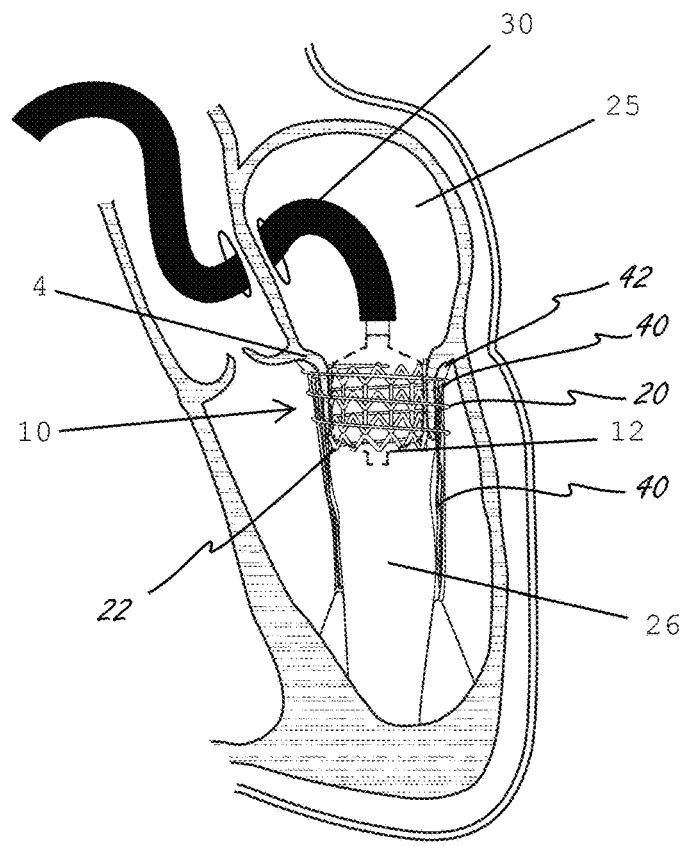
Figures 27, 28:
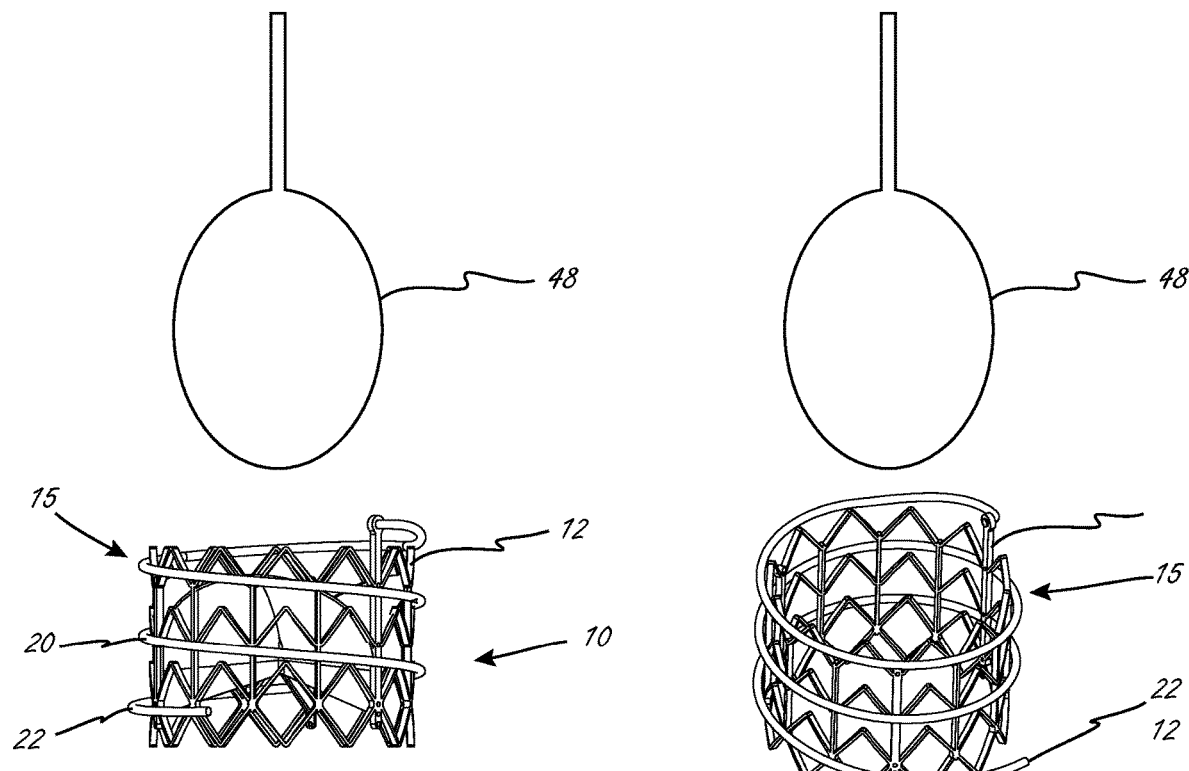
FIGS. 27 and 28 illustrate expanding of the frame structure using a balloon, in accordance with embodiments.

Frame structure 12 is expanded once valve 10 is in the desired location as shown in FIG. 25. The frame structure 12 may comprise a first and second opposite ends, the first end extending above a native valve and the second end extending below the native valve when the frame structure 12 is anchored to the native valve 4. In the illustrated embodiment, the frame structure 12 is expanded with a balloon 48 as shown in FIGS. 27-28. In various embodiments, the frame structure 12 is self-expanding. The self-expanding exemplary frame structure 12 is formed of a shape memory material or any material having superelastic properties. The self-expanding frame structure 12 is configured and expands in a similar manner to a self-expanding stent or scaffold. Expanding the frame structure 12 comprises removing a sheath (for example, outer sheath 50) of the delivery device 30 from the frame structure 12.

Figure 26:
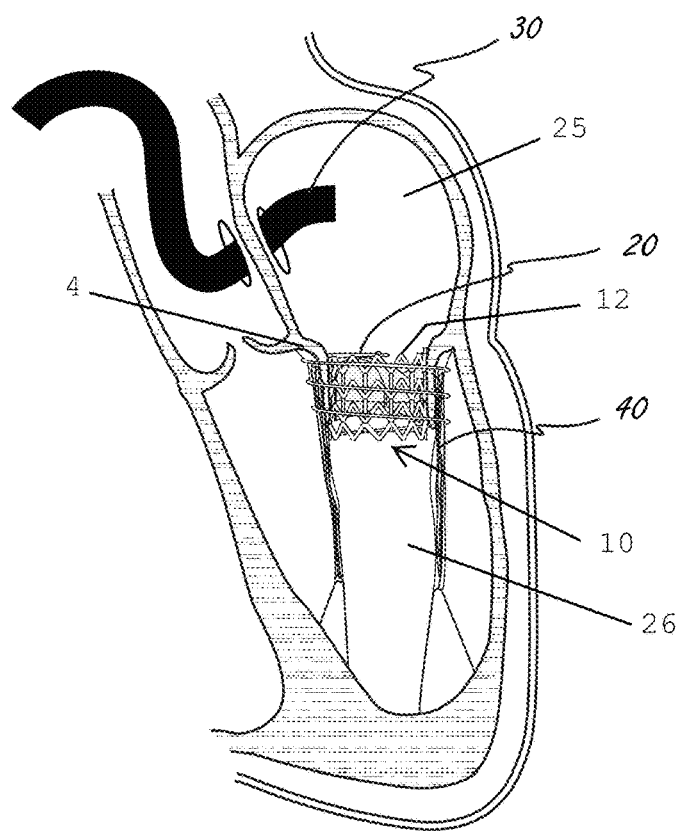

Once the frame structure 12 is expanded the entire valve assembly 10 is released from the delivery catheter 30 and the delivery catheter 30 is removed as shown in FIG. 26. In some embodiments, expansion of the frame structure 12 may occur simultaneously with release of the frame structure 12 from the delivery catheter 30.

In the illustrated embodiment, the valve structure 14 and frame structure 12 are deployed together. One of ordinary skill in the art will appreciate, however, that the frame structure 12 can be deployed first and then receive the prosthetic valve segment 14.

In various embodiments, valve prosthesis 10 does not include a valve segment 14. Instead, the frame structure 12 and anchor 15 are positioned within the native valve 4. The frame structure 12 is configured to receive a valve segment 14 delivered separately. In certain embodiments, the frame structure 12 can be configured to receive one of several valve sizes and types. In this manner, a clinician can choose the proper valve for the individual patient.

In the illustrated embodiment, the helical wire 20 of anchor 15 guides the valve system 10 along a desired axis into position adjacent the native valve 4. The wire 20 also provides an initial anchoring. The valve prosthesis 10 is finally anchored when the frame structure 12 is expanded within the native valve 4. The frame structure 12 dilates the valve leaflets 14 and the compressive force fixes the valve prosthesis 10 into position. Thereafter tissue ingrowth ensures the valve prosthesis 10 remains seated and does not migrate.

The valve devices described herein in accordance with the present disclosure provides several advantages over conventional valve systems. Embodiments described herein provide an easy-to-use, repositionable device. Unlike conventional valve systems, the valve prosthesis described herein reduces the risk of injuring or tearing chordae. Typical mitral valve replacement systems involve implanting a prosthetic annulus or ring around the valve. The ring increases the circumference of the valve and risks occluding the entry to the aortic valve. The valve device described herein overcomes these and other problems.

Figure 29:
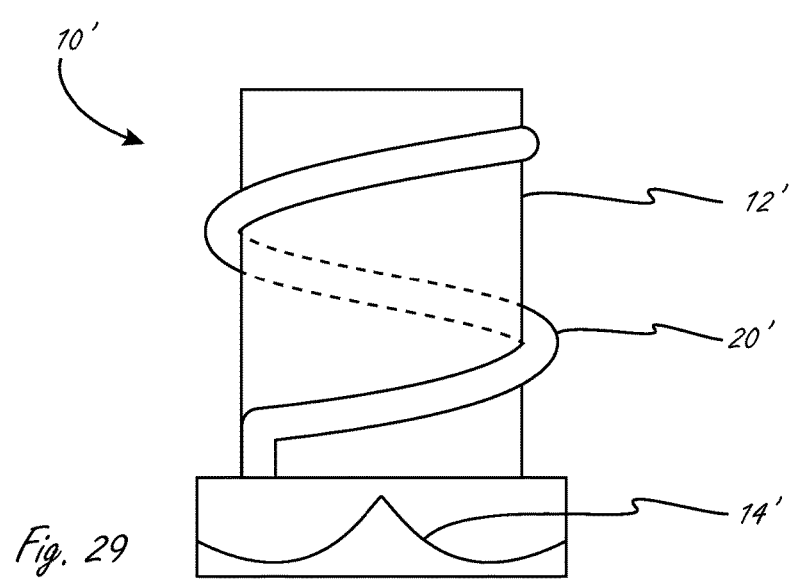
FIG. 29 is a front view of another percutaneous valve similar to the one of FIG. 6, in accordance with embodiments.

FIG. 29 illustrates another embodiment in accordance with the present disclosure. A valve prosthesis 10' includes a helical wire 20' and frame structure 12'. Valve structure 10' is similar to valve 10 except that valve segment 14' is fixed within a separate end of frame structure 12'. Wire 20' is wrapped around a lower portion of the frame structure 12 having a smaller diameter than the upper portion of the frame structure 12 to which the valve segment 14' is fixed.

FIGS. 30A to 30F illustrate several other embodiments in accordance with the present disclosure. Each of valves 10a to 10f includes a helical wire and frame. Each can optionally include a valve segment within the frame.

Figure 30A:
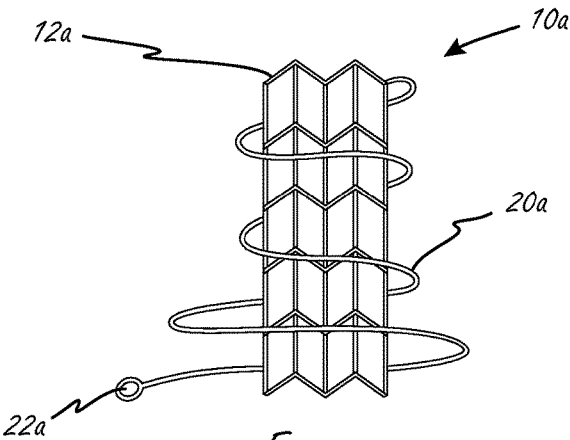
FIGS. 30A-30F are front views of other percutaneous valves similar to the one of FIG. 6, in accordance with embodiments.

FIG. 30A shows a valve prosthesis 10a which is similar to valve prosthesis 10 except that free end 22a includes an atraumatic ball tip. Also, wire 20a has a tubular shape at one end and a frustoconical shape at another end. Frame structure 12a is substantially similar to frame structure 12.

Figure 30B:
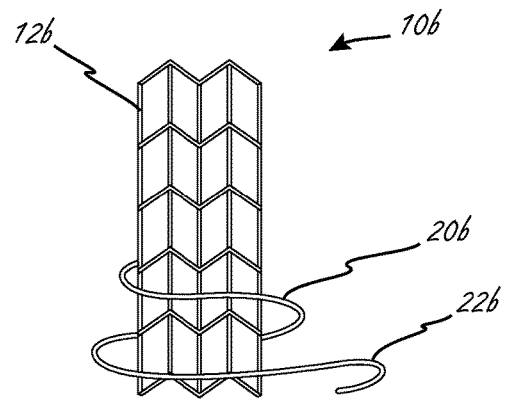

FIG. 30B shows a valve prosthesis 10b which is similar to valve prosthesis 10 except that free end 22 has a pigtail tip. Also, wire 20b is attached to an intermediate portion of frame structure 12b instead of an end of the frame structure 12b. Frame structure 12b is substantially similar to frame structure 12.

Figure 30C:
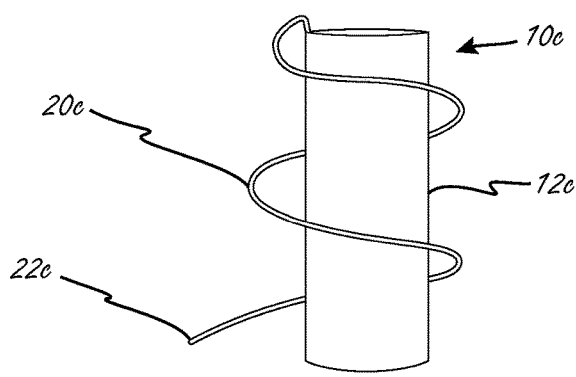

FIG. 30C shows a valve prosthesis 10c which is similar to valve prosthesis 10 except that frame structure 12c is a tubular structure instead of a scaffold or stent-like structure. The frame structure 12c can be formed of expandable materials such as polyurethane or polycarbonate urethane. The wire 20c is substantially similar to wire 20. The free end 22c is substantially similar to free end 22.

Figure 30D:
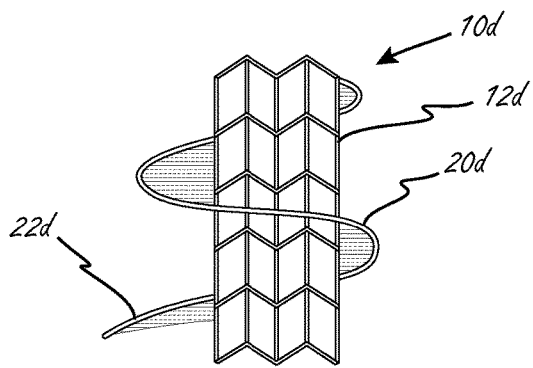

FIG. 30D shows a valve prosthesis 10d which is similar to valve prosthesis 10 except that the anchor 15 is formed of a three-dimensional surface 20d instead of a wire 20. Three-dimensional surface 20d comprises a free end 22d, which may be substantially similar to any of the free ends described herein. Frame structure 12*d* is substantially similar to frame structure 12.

Figure 30E:
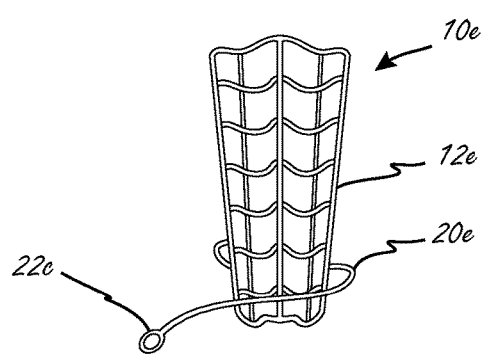

FIG. 30E shows a valve prosthesis 10*e* which is similar to valve prosthesis 10 except that frame structure 12*e* has a conical shape instead of a tubular shape. One will appreciate from the description herein that the frame structure 12 may take a variety of shapes in accordance with the present disclosure. The wire 20*e* is substantially similar to wire 20. The free end 22*e* is substantially similar to free end 22.

Figure 30F:
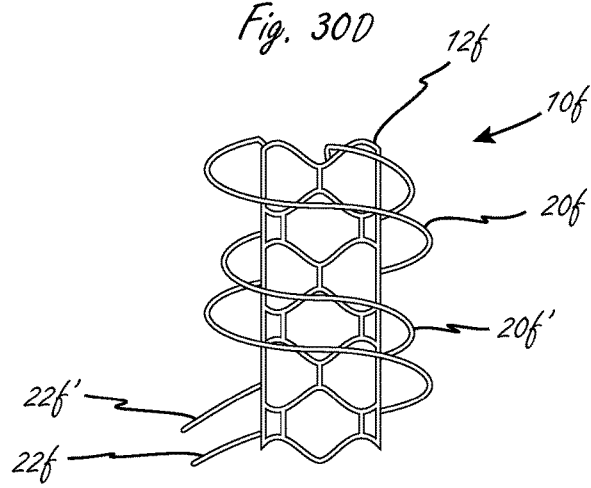

FIG. 30F shows a valve prosthesis 10*f* which is similar to valve prosthesis 10 except that the valve device 10*f* includes a plurality of wires 20*f* and 20*f*. The use of a plurality of wires 20*f* and 20*f'* provides increased anchoring security. Because it may be difficult to insert both free ends 22*f* and 22*f'*, one or both free ends 22*f* and 22*f'* may include a sharp point for piercing tissue. In this manner, the sharp end can pierce the valve annulus or leaflets. Barbs or other mechanisms may be employed to increase anchoring of the wire. For example, one or both of the wires 20*f* and 20*f'* may include a braided surface or barbs to prevent axial dislocation once it is screwed into place.

FIGS. 31-35 illustrate another valve prosthesis 10*g* embodiment which is similar to valve prosthesis 10 except that the valve prosthesis 10*g* is configured for anchoring from the bottom (i.e., ventricular side) of the native mitral valve annulus. By comparison to valve prosthesis 10, valve prosthesis 10*g* includes a helical anchor 15*g* in a frustoconical (or conical) shape with a narrow section at the bottom of the frame structure 12*g* and a wider section along a central portion of the device 10*g*. In the illustrated embodiment, the widest section of the anchor 15*g* is near a top of the coil 15*g*. In the illustrated embodiment, the coiled anchor 15*g* extends from a bottom of the frame structure 12*g* to a top section of the frame structure 12*g* in the collapsed (e.g., unexpanded) configuration. The frame structure 12*g*, anchor 15*g*, and valve segment (not shown) are otherwise generally similar to those of valve 10 or any of the frame structures, anchors, or valve segments described herein.

Figure 6:
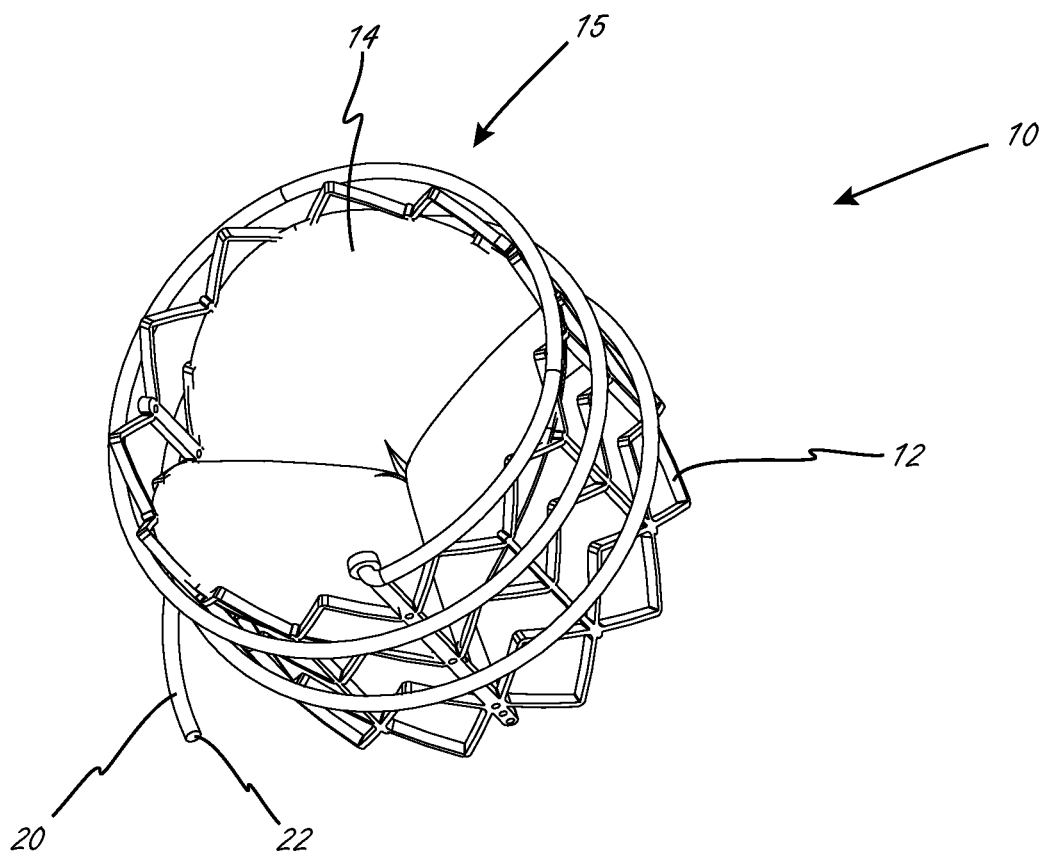
FIGS. 6-10 are several views of a percutaneous valve for replacement of a diseased native valve, in accordance with embodiments.
Figure 7:
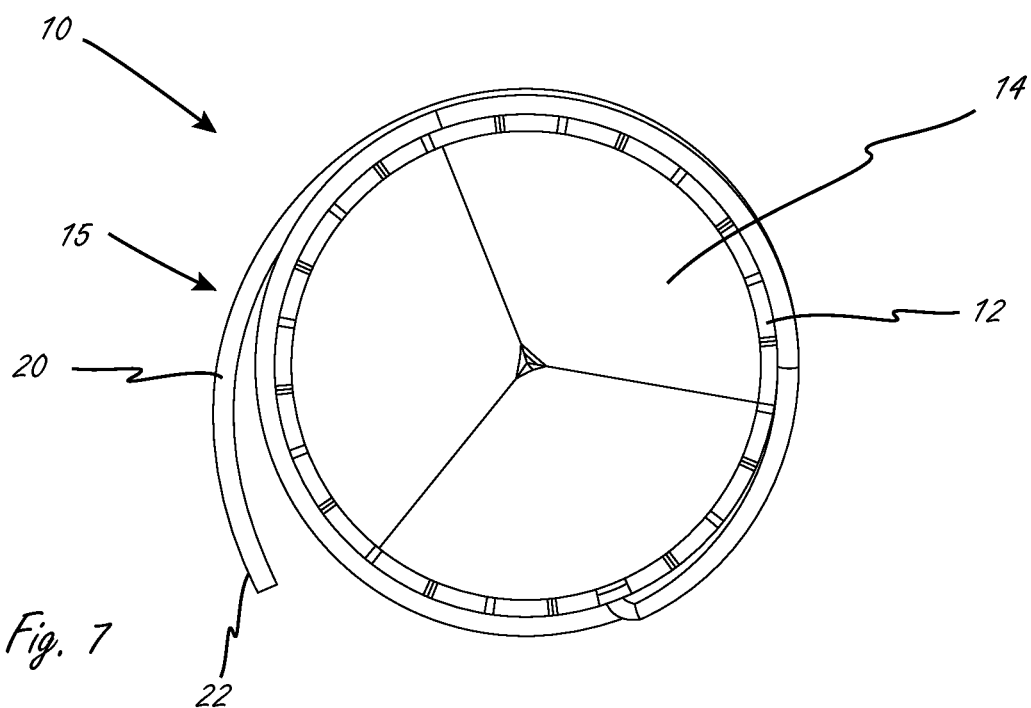
Figure 8:
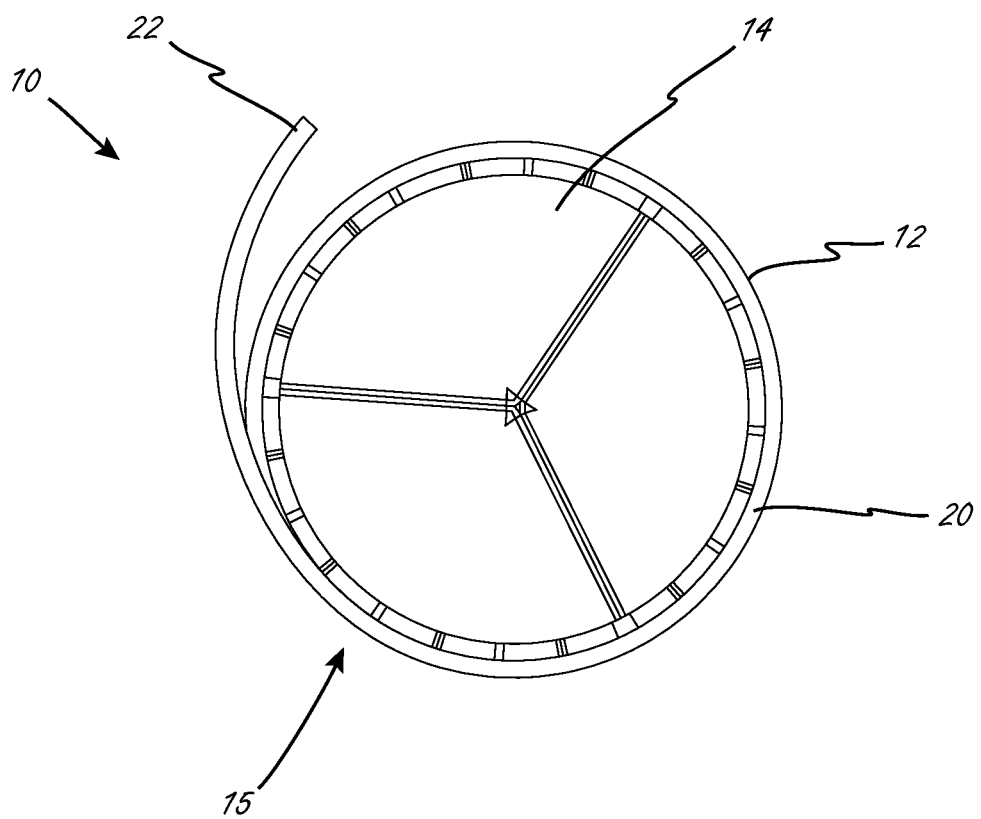
Figure 9:
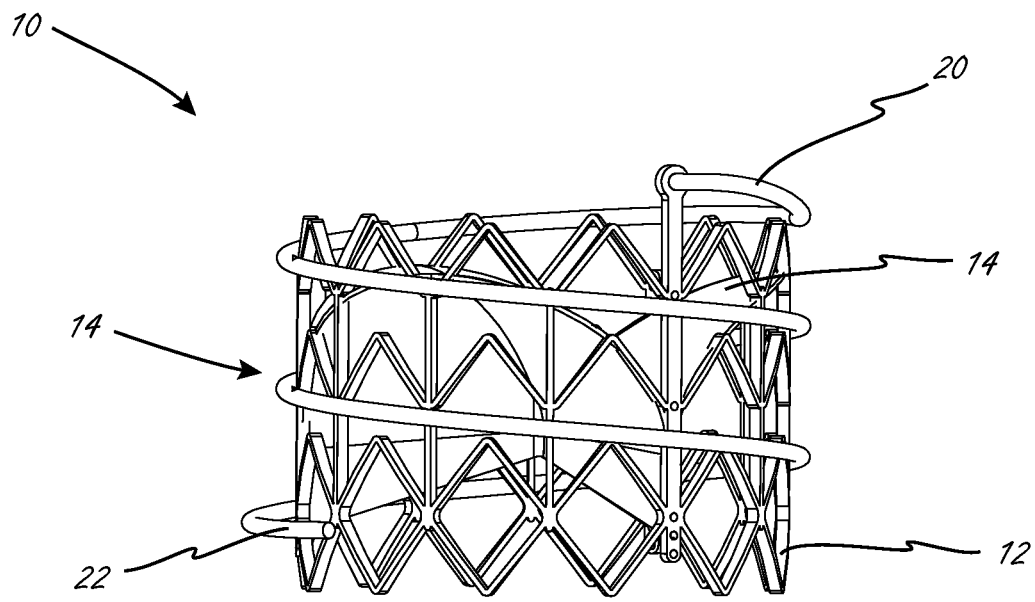
Figure 10:
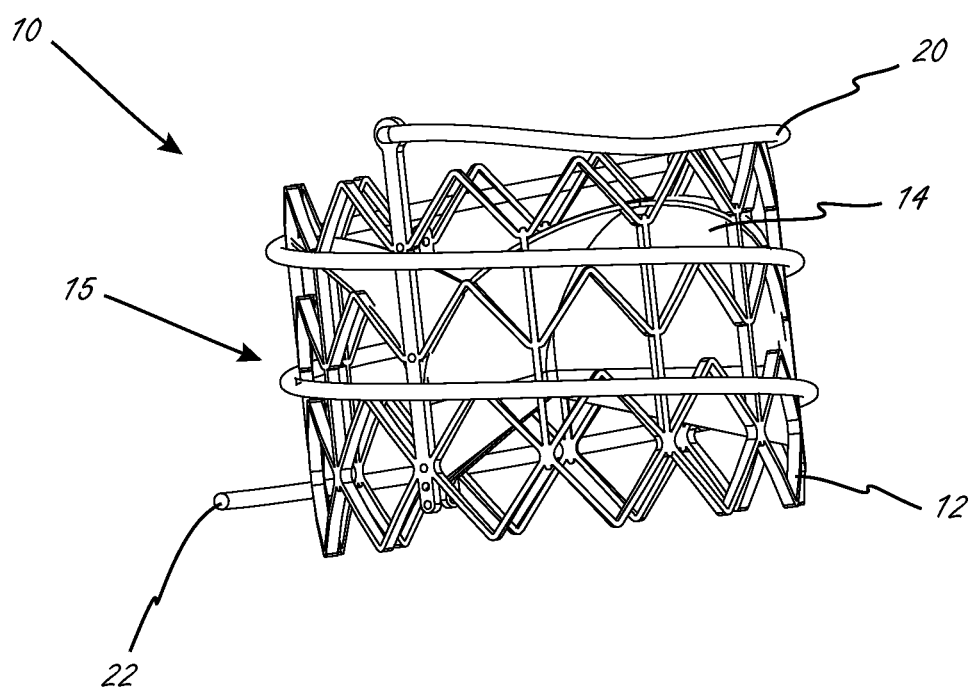

The anchor 15*g* is inverted compared to anchor 15 in FIG. 6. A free end 22*g* is positioned along a central section of the valve prosthesis 10*g*. As will be described below in more detail with reference to FIGS. 43A-43AF, the valve prosthesis device 10*g* may be configured to be inserted through the native valve (e.g. mitral valve) and anchored from below. In particular, the anchor 15*g* may be configured to capture the chordae and/or native valve leaflets from below the valve annulus. This inverted design provides a simple transcatheter approach to the diseased native valve while providing a long-term and clinically useful anchoring mechanism.

Figure 35:
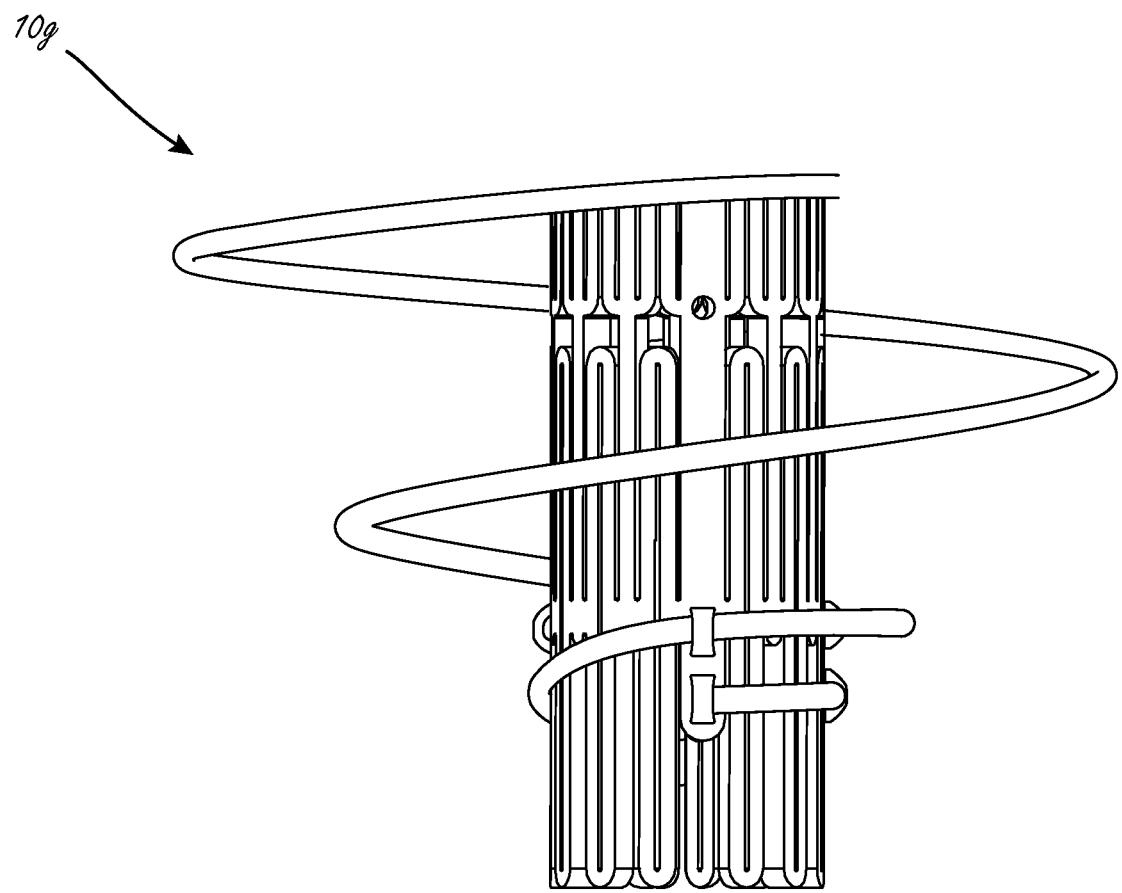
Figure 37:
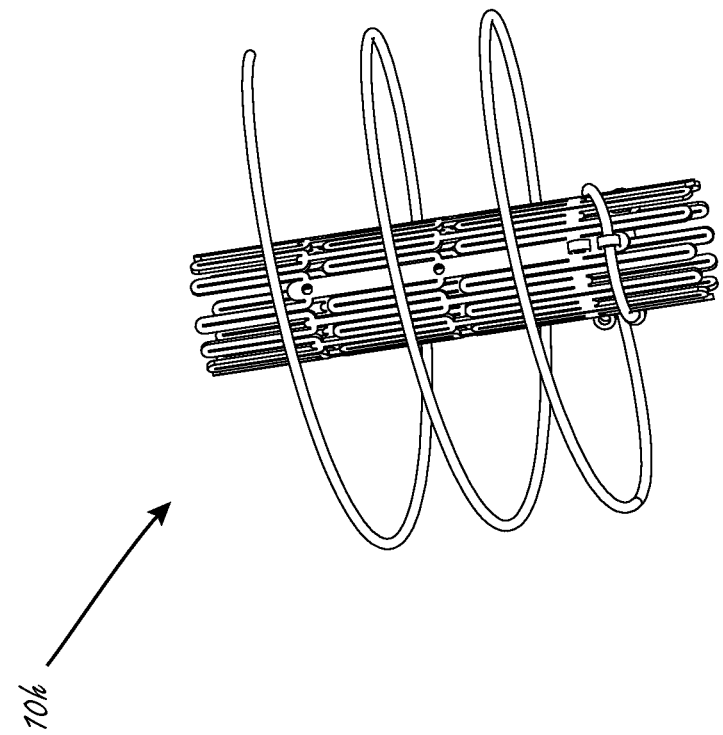
FIGS. 36-39 illustrate another valve device similar to the one of FIG. 6, in accordance with embodiments.
Figure 36:
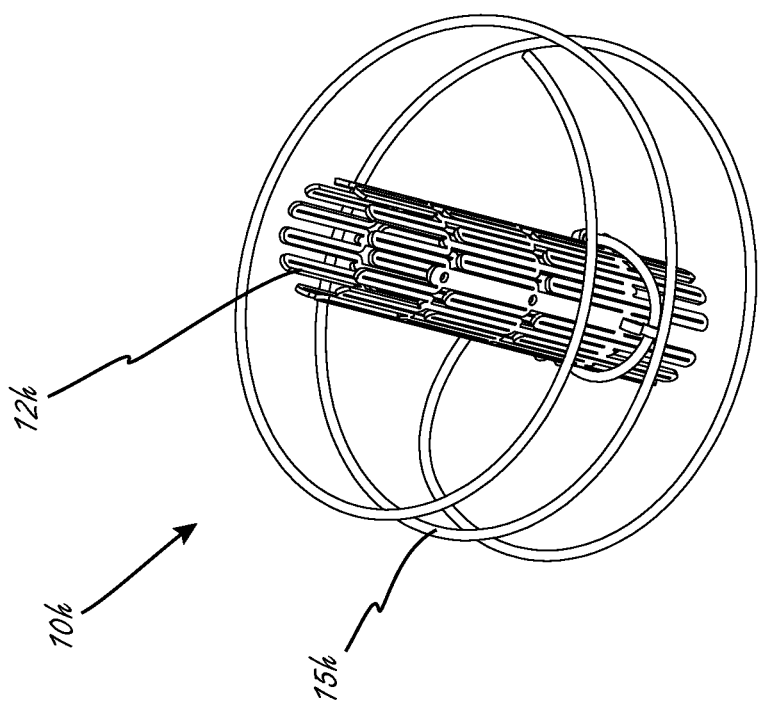
Figure 39:
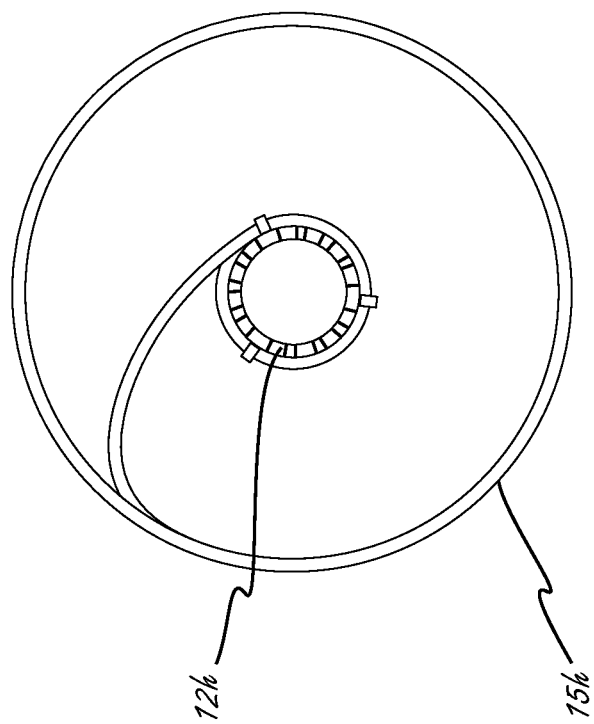
Figure 38:
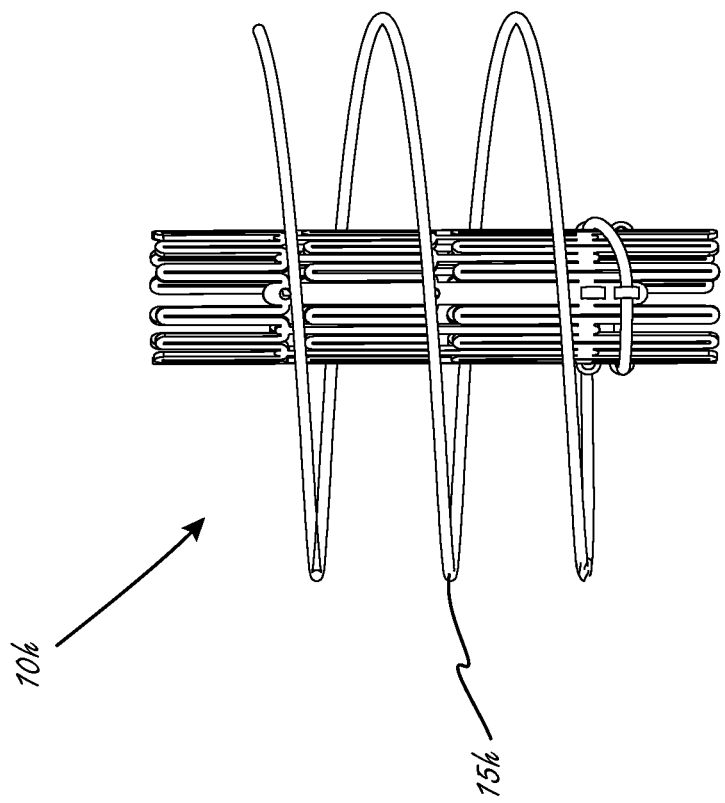

The exemplary anchor 15*g* is attached to the frame structure 12*g* at one end 57. In the illustrated embodiment, as best shown in FIG. 35, the end is fixed to a strut of the frame structure 12*g*. This attached end can be attached by suitable means as would be understood by one of skill in the art from the description herein including, but not limited to, a weld, an adhesive, and a mechanical fastener. In the illustrated embodiment, the valve prosthesis 10*g* includes optional eyelets 55 for supplemental securement of the coil anchor 15*g*. The exemplary anchor 15*g* is formed in the shape of a coil wire similar to the other anchor wires described herein and with a section extending through the eyelets 55. The coil 15*g* is slidably held within the eyelets 55. The coil 15*g* may be configured to retain its shape after deployment. As the frame structure 12*g* is subsequently expanded, the coil wire anchor 15*g* slides through the eyelets 55 to allow the frame structure 12*g* to expand within the larger diameter of the anchor 15*g*. The eyelets 55 hold the coil wire anchor 15*g* in a radial position relative to the frame structure 12*g*. This may mitigate against the risk of the coil 15*g* bending away from the frame structure 12*g* and/or fracture failure.

Figure 32:
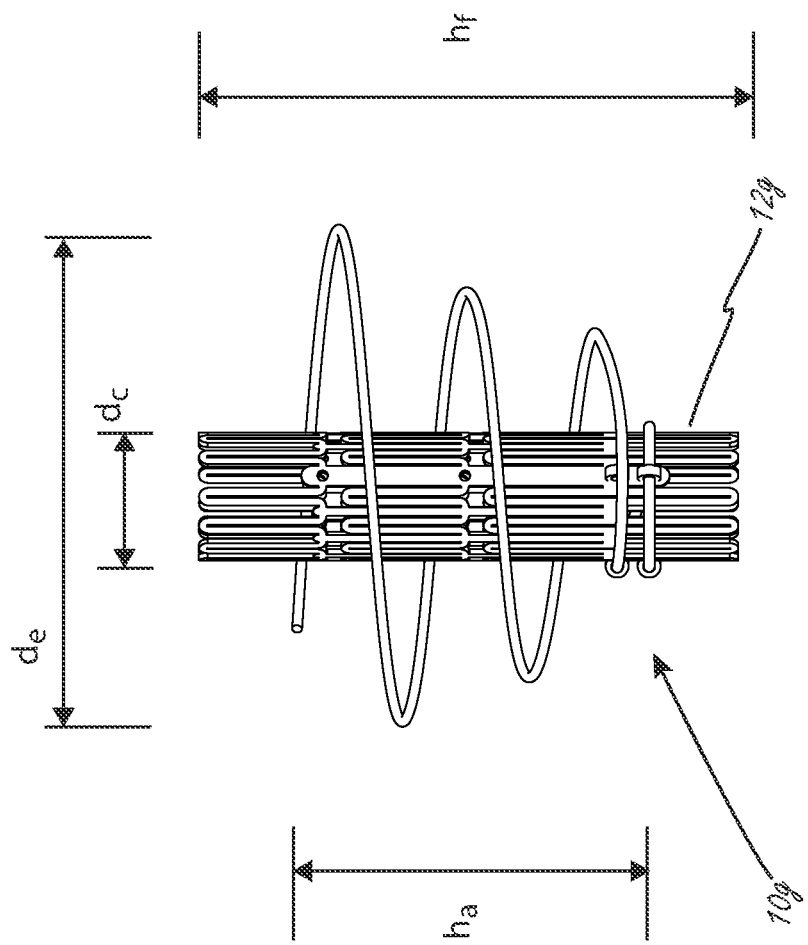
FIGS. 31-35 illustrate another valve device similar to the one of FIG. 6, in accordance with embodiments.
Figure 31:
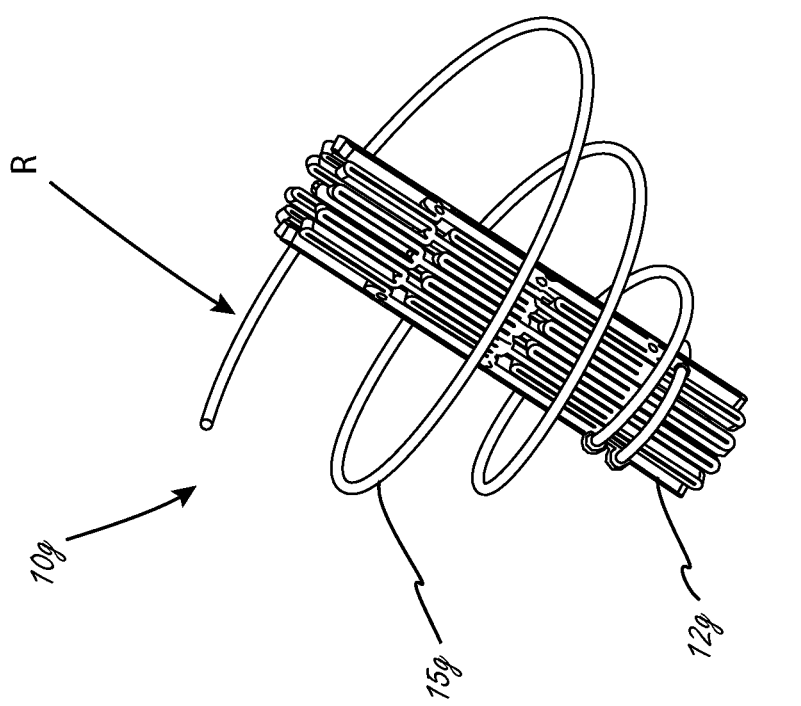
Figures 33, 34:
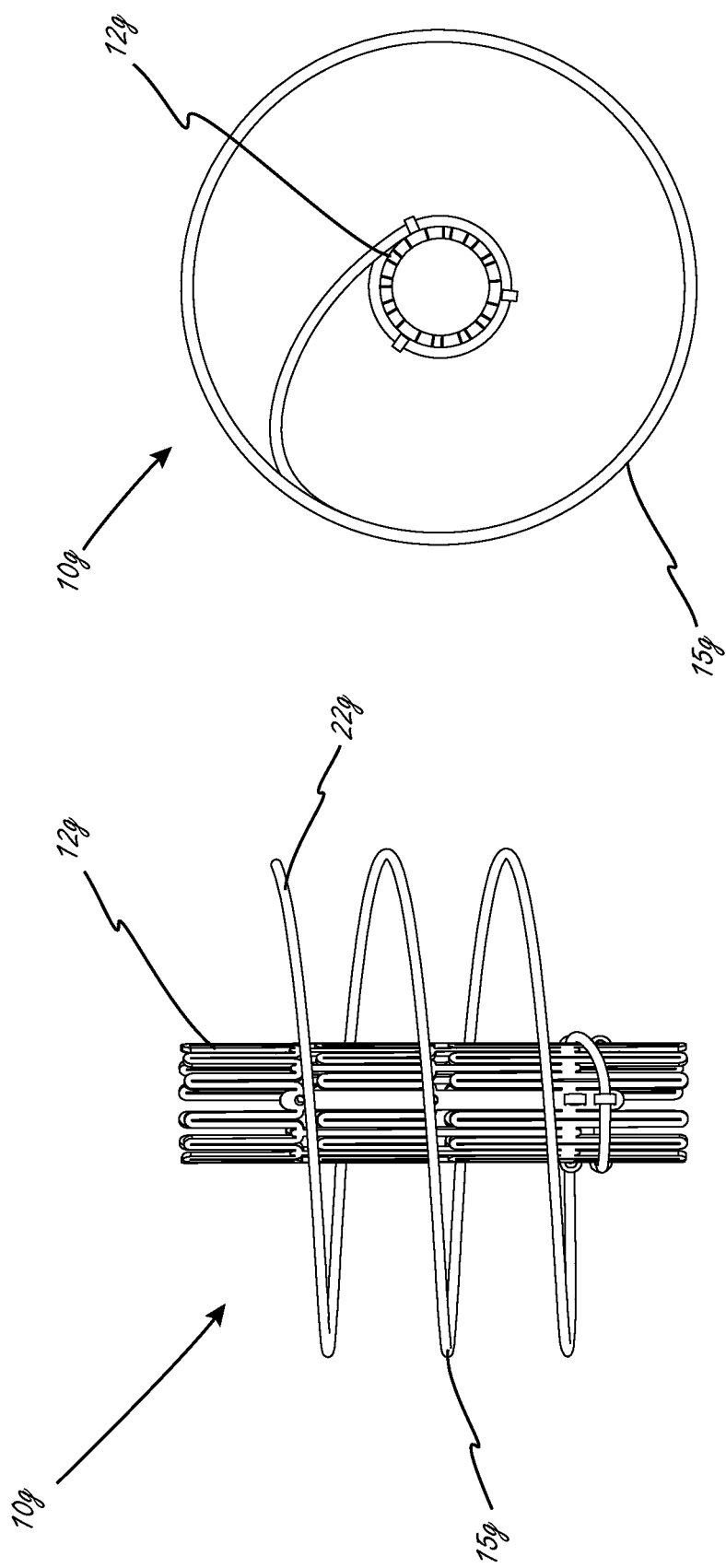

With continued references to FIGS. 31-32, in an exemplary embodiment, the anchor 15*g* has a radius of curvature (R) is between about 15 mm and about 50 m. In various embodiments, R is about 35 mm. In various embodiments, the height of the anchor ($H_a$) is between about 10 mm and about 60 mm. In various embodiments, the height of the anchor ($H_a$) is between about 3 mm and about 60 mm. In various embodiments, the height of the anchor ($H_a$) is between about 3 mm and about 6 mm. In various embodiments, the height of the anchor ($H_a$) is between about 3 mm and about 50 mm. In various embodiments, Ha is about 30 mm. In various embodiments, the height of the frame structure ($H_f$) is between about 20 mm and about 55 mm. In various embodiments, $H_f$ is about 30 mm. In various embodiments, the width of the frame structure in a collapsed configuration ($W_c$) is between about 4 mm and about 8 mm. In various embodiments, $W_c$ is about 6 mm. In various embodiments, the width of the frame structure 12*g* in an expanded configuration ($W_e$) is between about 25 mm and about 35 mm. In various embodiments, $W_c$ is about 30 mm. In various embodiments, the anchor 15*g* is formed as a coil with varying widths and the minimum width (or radius) is about 10 mm and the maximum radius is about 30 mm.

It will be understood by one of ordinary skill in the art that any of the anchor embodiments described herein may be formed with similar dimensions as those described herein with reference to anchor 15*g*, or any of the other anchors described herein.

It will be understood by one of ordinary skill in the art that any of the frame structure embodiments described herein may be formed with similar dimensions as those described herein with reference to frame structure 12*g*, or any of the other frame structures described herein.

FIGS. 36-39 illustrate another valve prosthesis 10*h* embodiment which is similar to valve prosthesis 10*g* except that the anchor 15*h* has a generally symmetrical tubular profile. A proximal end 57*h* of anchor 15*h* extends inwardly from the coil body to an attachment point on the frame structure 12*h*. The end 57*h* wraps around the frame structure 12*h* and is fixed to the frame structure 12*h* as described herein. The coil 20*h* can have a portion of a turn around the collapsed frame structure 12*h*. The coil 20*h* can have one or more turns around the collapsed frame structure 12*h*. A portion of the coil 20*h* may extend through eyelets 55*h* as described herein. Similar to valve 10*g*, the frame structure 12*g* may be allowed to expand by the coil anchor 15*g* sliding through the eyelets 55*h*. At the same time, the eyelets 55*h* may maintain a relative radial position of the respective portion of the coil anchor 15*g*. Although the embodiment shows eyelets 55*g*, one of ordinary skill in the art will appreciate from the description herein that other mechanisms may be suitable for guiding the anchor 15*g* including, but not limited to, hooks and guiderails or the like, or any combination thereof.

FIGS. 40-42 illustrate exemplary valve prosthesis embodiments 10*i*, 10*j*, and 10*k* which are similar to valve prosthesis 10*g* and having anchors 15*i*, 15*j*, and 15*k* of varying configurations. In the illustrated embodiments, the exemplary anchors include an atraumatic tip 60 as described herein. The atraumatic tip may be formed as a ball, rounded edge, J-tip, or any other suitable means as would be understood by one of skill in the art from the description herein.

FIG. 40 illustrates a valve prosthesis 10*i* which is similar to valve prosthesis 10*g* except that the anchor 15*i* does not have a linear or symmetrical shape. At least a portion of anchor 15*i* has a tapered shape. In the illustrated embodiment, the anchor 15*i* is formed as a coil and at least one turn of the windings has a curvilinear shape. Whereas at least some of the turns in the windings of anchor 10*g* are generally flat in a plane, the respective turns in the valve prosthesis 10*i* are configured to extend out of the plane in a three-dimensional, degenerate surface. In the illustrated embodiment, the curvilinear shape is more pronounced, and the radius of curvature is greater, on the turn at the top than the turns at the bottom. The overall shape of anchor 15*i* is generally conical. This shape may promote insertion of the anchor through the native valve leaflets as will be described in more detail below.

FIG. 41 illustrates a valve prosthesis 10*j* which is similar to valve prostheses 10*g*, 10*h*, 10*i*, and 10*j*. Anchor 15*j* is formed as a coil with a complex, tapered shape. FIG. 41 illustrates a valve prosthesis 10*k* which is similar to valve prostheses 10*g*, 10*h*, 10*i*, and 10*j* except that the anchor 15*k* is configured for facilitating easier insertion through the native valve. In the illustrated embodiment, the anchor 15*k* is formed as a coil with a relatively smaller form factor than the other anchors. The smaller radial width of the coil may promote insertion through the native valve while still having sufficient width to capture a necessary number of chordae and/or the native valve leaflets.

Any of the anchor embodiments described herein may have windings with varying shapes and curvatures. In various embodiments, a lower portion of the anchor has windings which curve in a first direction and an upper portion has windings which curve in a second direction (in planes generally perpendicular to a major axis of the frame structure and/or anchor). In various embodiments, the second direction is opposite the first direction. In various embodiments, the anchor includes a first portion having a first radius of curvature (in a plane generally perpendicular the major axis of the frame structure and/or anchor), and a second portion having a second radius of curvature. In various embodiments, the anchor includes a third portion having a third radius of curvature. In various embodiments, the anchor includes a fourth portion having a fourth radius of curvature. In various embodiments, the anchor includes a plurality of portions each having a unique radius of curvature. In various embodiments, the respective radii of curvature are all different. In various embodiments, the second radius of curvature is greater than the first, and the third radius of curvature is greater than the second. In various embodiments, the radius of curvature of the upper windings is greater than 30 mm. In various embodiments, the radius of curvature of the lower windings is greater than 10 mm.

FIG. 42 illustrates an exemplary modality for attachment of the anchor 15*j* to a frame structure 12*j*. In various embodiments, the anchor 15*j* is welded to the frame structure 12*j*, for example, to one of the struts of the frame structure 12*j*. In various embodiments, one end of the anchor 15*j* is configured to extend inside the frame structure 12*j* where it is mechanically fastened. In the embodiment illustrated in FIG. 42, the anchor 15*j* is fixed to a bottom-most (inferior) end of the frame structure 12*j*.

A method of using a valve device similar to valve devices 10*g*, 10*h*, 10*i*, 10*j*, 10*k*, 10*l*, 10*m*, etc. will now be described with reference to FIGS. 43A to 43AF.

Figure 43B:
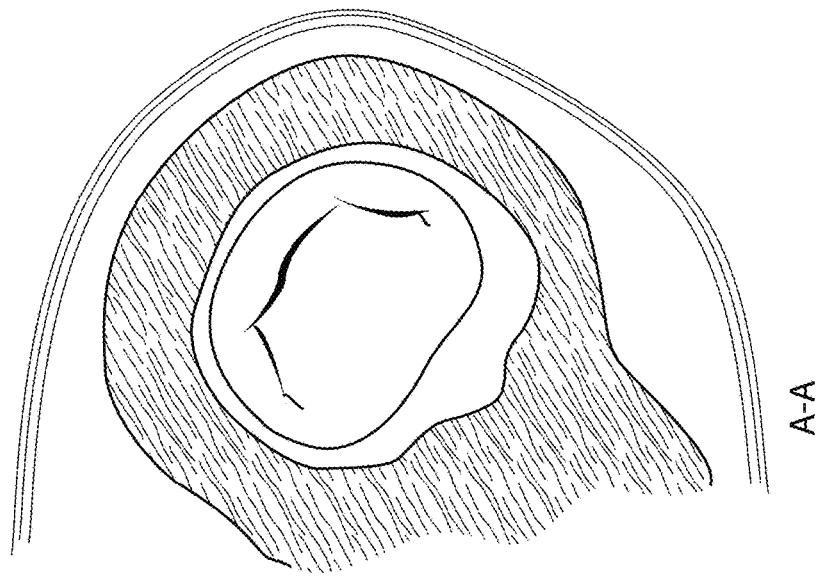
FIGS. 43A-43AF are sequential views of a method of implanting a device similar to the one of FIGS. 6 and 31, in accordance with embodiments.
Figure 43A:
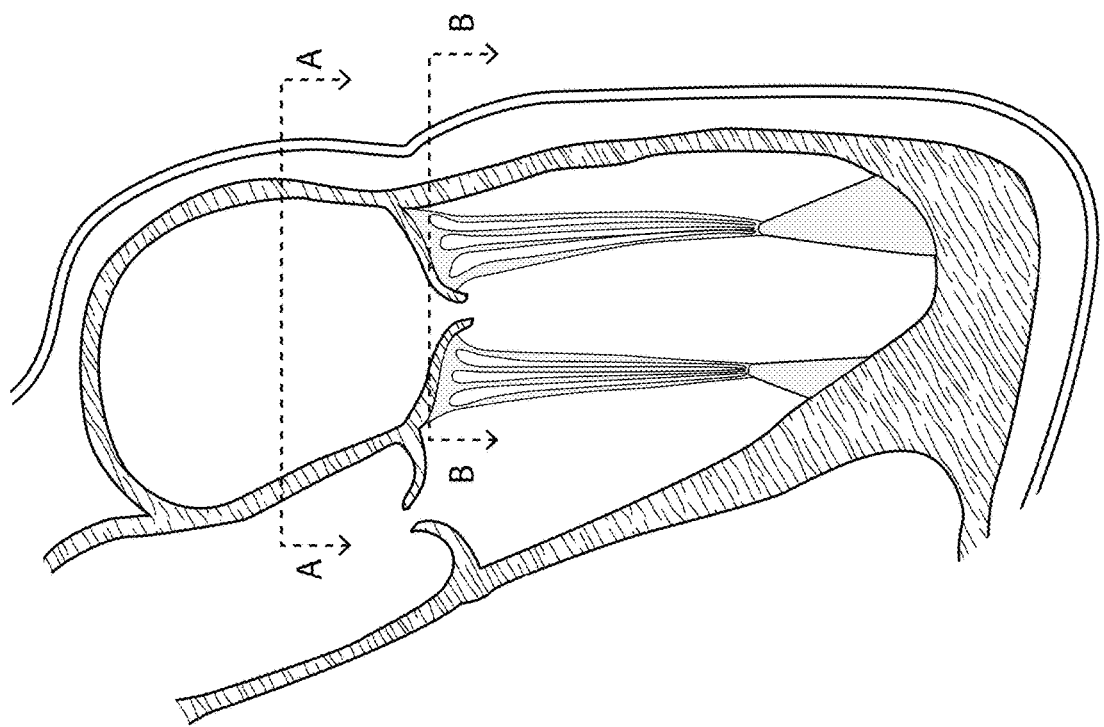

FIGS. 43A-43AF show sequential views of a method of implanting a valve prosthesis 10 using a delivery device 30'. The valve prosthesis 10 may be similar to any of the valve prostheses described herein or understood by one of ordinary skill in the art from the description herein. For example, valve prosthesis 10 may be substantially similar to the valve prosthesis 10*g* shown in FIGS. 31-35 and may comprise a frame structure 12*g* and anchor 15*g* as described herein. The delivery device 30' may be substantially similar to any of the delivery devices described herein or understood by one of ordinary skill in the art from the description herein. The delivery device 30' may comprise an inner shaft or delivery tube 52 as described herein. The delivery device 30' may optionally comprise an outer shaft or outer catheter 50, a guidewire 54, and/or an inflatable balloon 48, in any combination thereof as desired by one of ordinary skill in the art. Not all elements are labeled in each of FIGS. 43A-43AF in order to make the illustrations less cluttered and easier to see.

While the method shown in FIGS. 43A-43AF is described in relation to a mitral valve replacement procedure, it will be understood by one of ordinary skill in the art that the methods described herein may be applied to a variety of procedures or anatomical areas, for example other atrioventricular valves of the heart or the like. For example, the methods described herein may be applied to replacement of a diseased aortic valve or tricuspid valve.

Figure 43D:
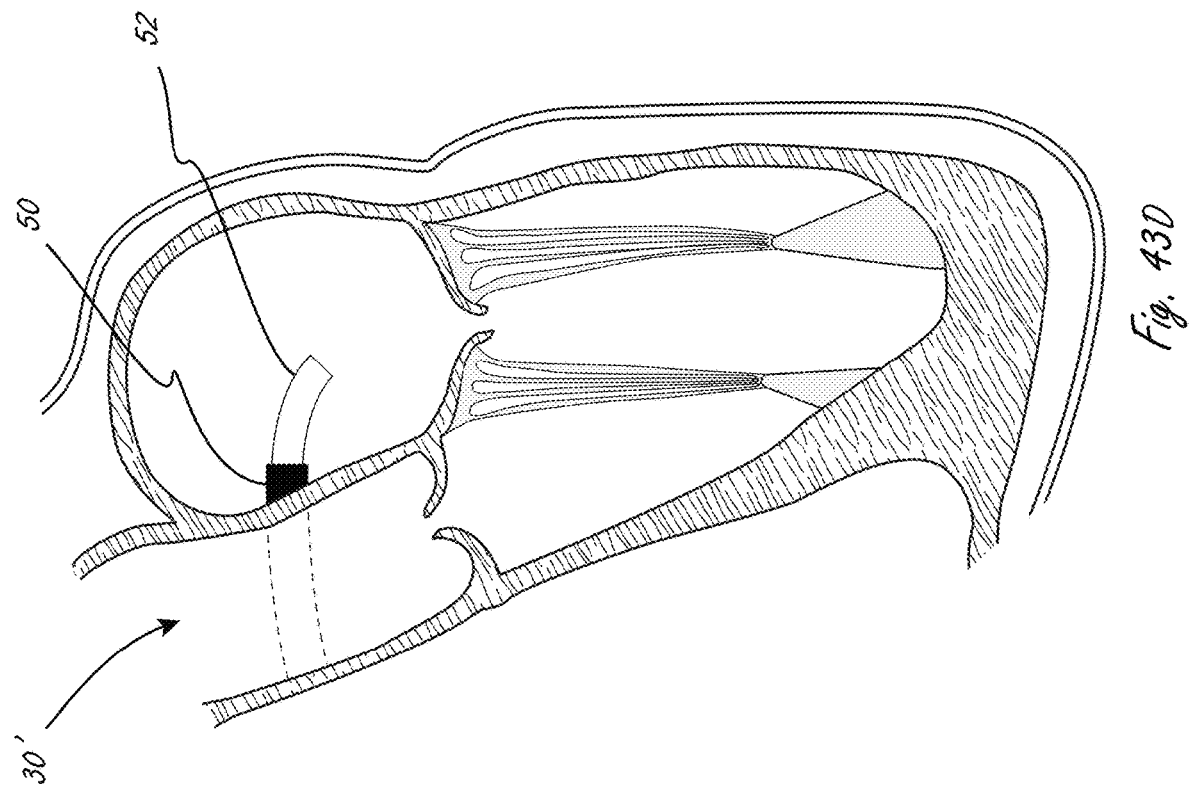
Figure 43C:
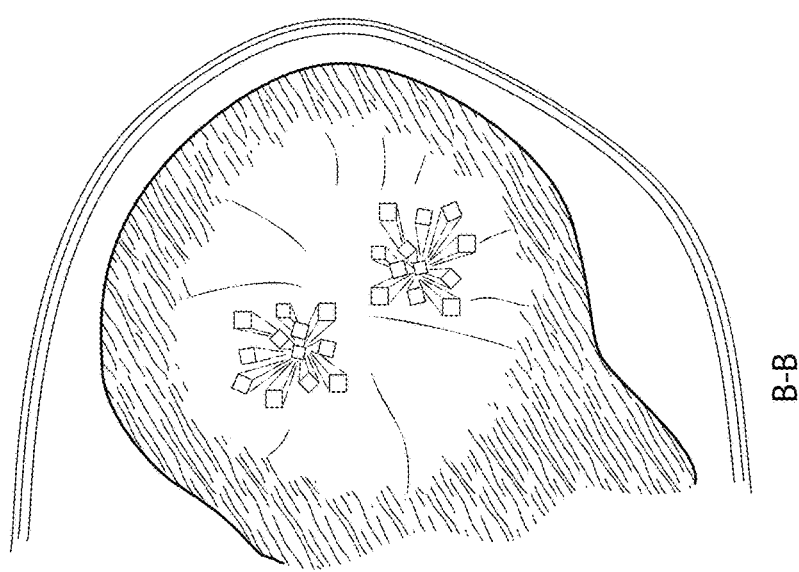
Figure 43F:
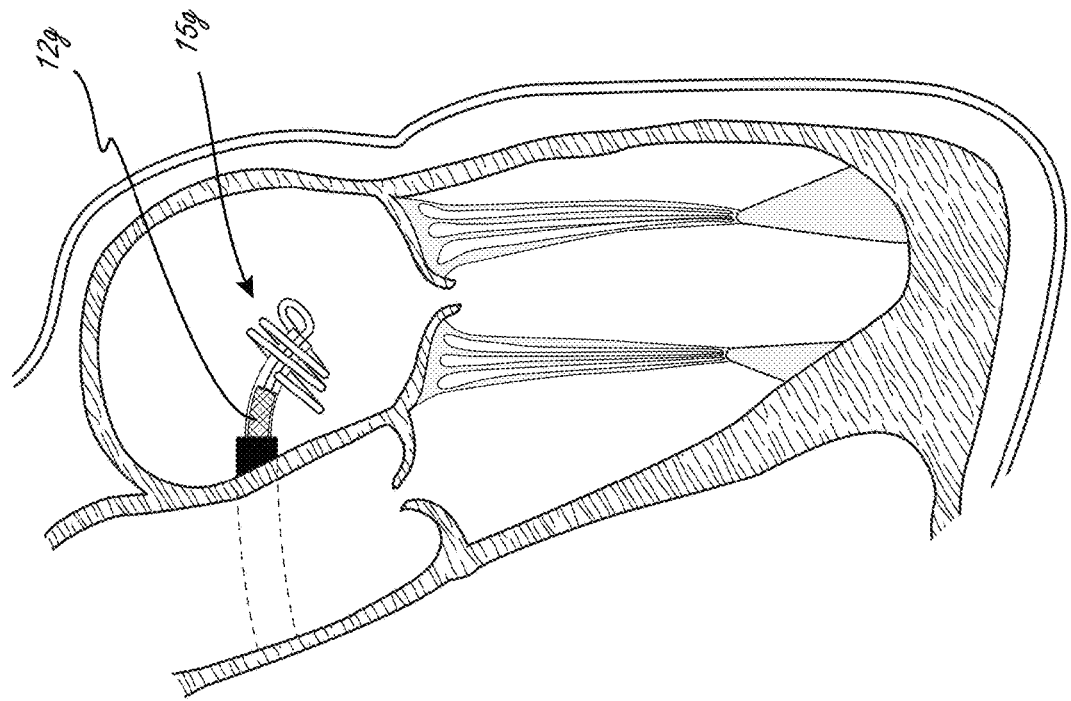
Figure 43E:
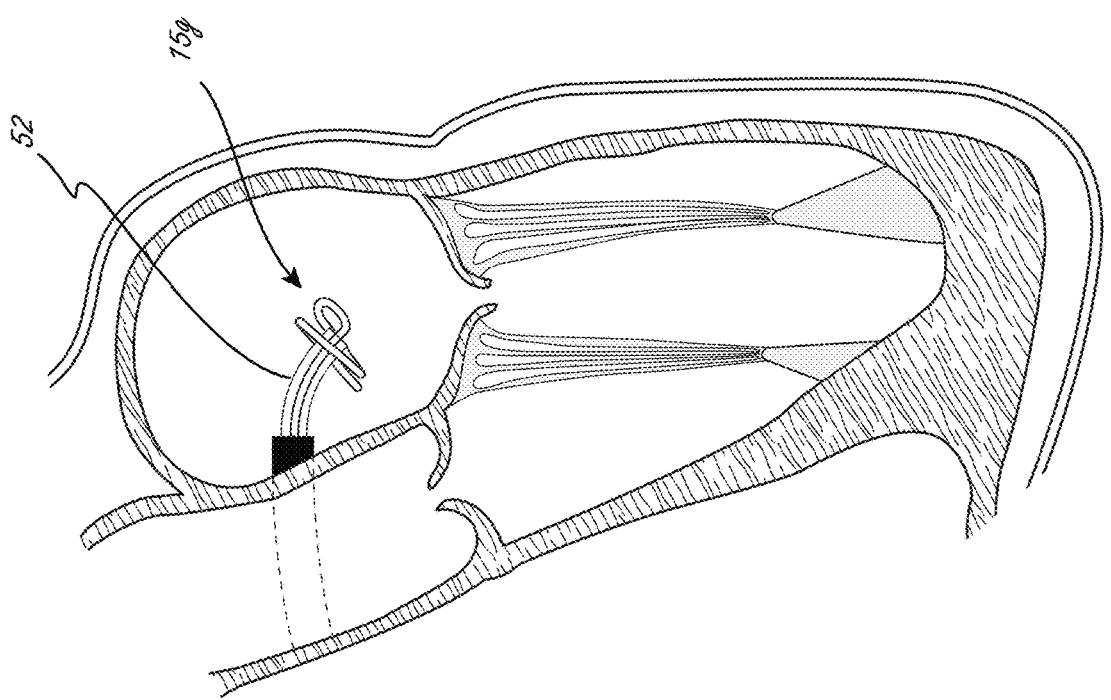

FIGS. 43A-43C shows various cross-section views of a heart 2 having a diseased mitral valve 4 which may be treated using the devices, systems, and methods described herein. The mitral valve 4 sits between the left atrium 25 and the left ventricle 26 and, when functioning properly, allows blood to flow from the left atrium 25 to the left ventricle 26 while preventing backflow or regurgitation in the reverse direction. As shown in FIG. 43A, the native valve leaflets 42 of the diseased mitral valve 4 do not fully prolapse and the patient experiences regurgitation. FIG. 43B shows a cross-sectional view of the heart 2 taken along line A-A, shown in FIG. 43A, which shows the native valve leaflets 42 of the mitral valve 4 from the viewpoint of the left atrium 25. FIG. 43C shows a cross-sectional view of the heart 2 taken along line B-B, shown in FIG. 43A, which shows the chordae tendineae 40 of the left ventricle 26.

As shown in FIG. 43D, a distal end of the delivery device 30' may be inserted into the left atrium 25 of the heart 2 via a transseptal puncture as described herein. For example, the distal ends of inner shaft 52 and/or outer sheath 50 may be advanced into the left atrium 25 of the heart 2. The inner shaft 52 may optionally be advanced distally into the left atrium 25 away from the distal end of the outer sheath 50. In some embodiments, advancing the inner shaft 52 relative to the outer sheath 50 may aid in deployment and/or placement of the valve prosthesis 10*g* as described herein. Alternatively, both the inner shaft 52 and the outer sheath 50 may be advanced distally into the left atrium 25 through the transseptal puncture.

Figure 43H:
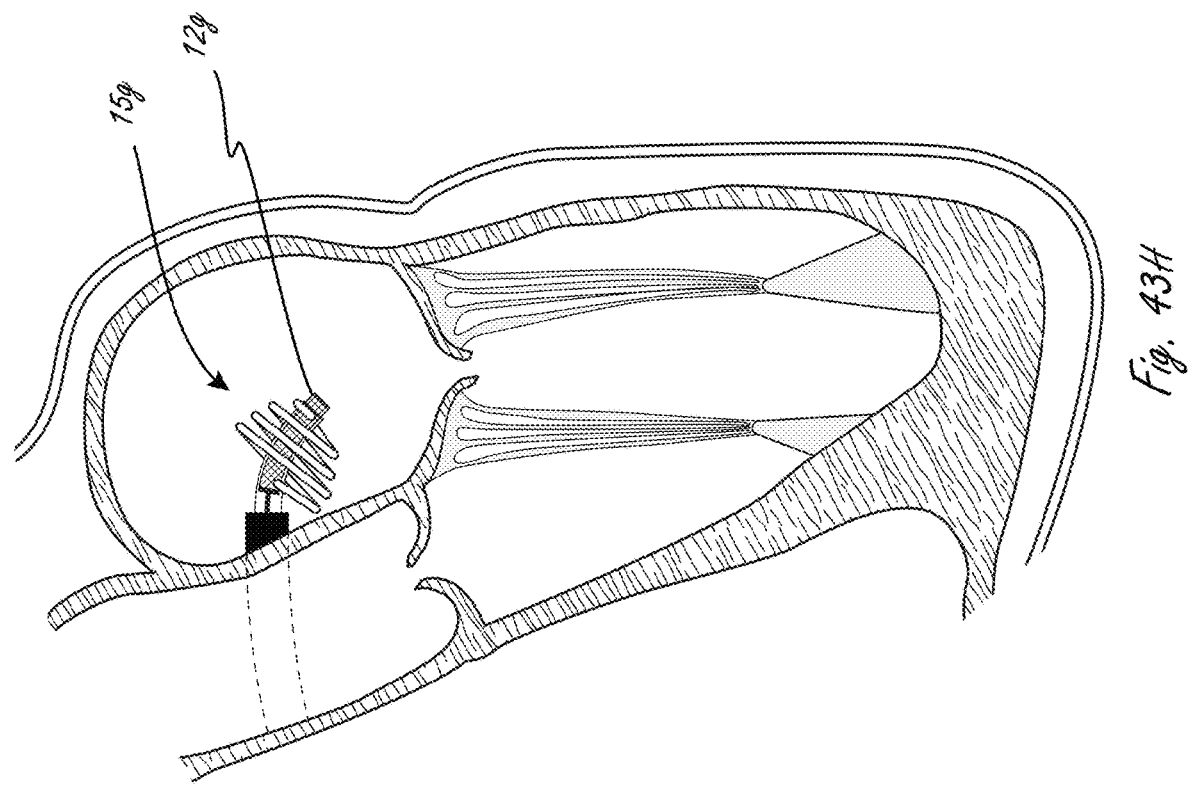
Figure 43G:
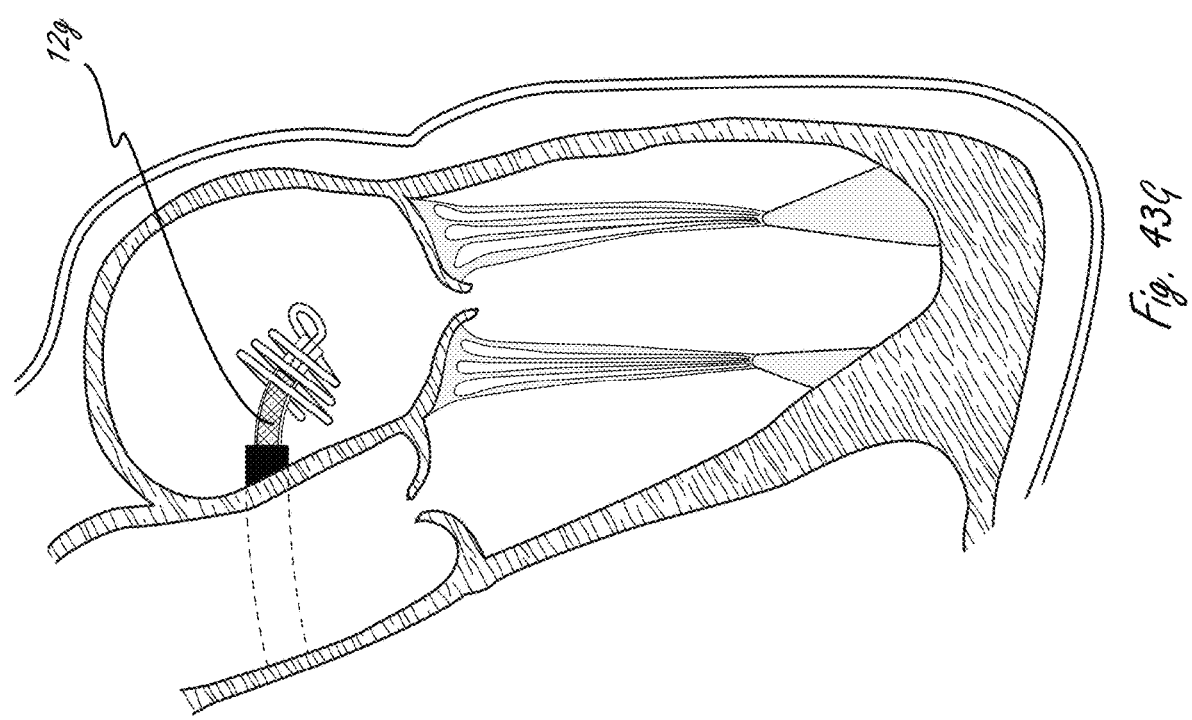

FIGS. 43E-43H show deployment of the anchor 15*g* from the distal end of the delivery device 30'. As described herein, at least a portion of the valve prosthesis 10*g* may be deployed from an undeployed (for example, compressed) configuration to an expanded configuration within the left atrium 25. At least a portion of the anchor 15*g* may be deployed from a delivery and/or elongated configuration to a deployed configuration within the heart. For example, anchor 15*g* may be actuated from an elongated configuration (e.g., from a straightened shape) to a deployed configuration (e.g., a pre-formed shape for implantation, such as a helical or conical shape as illustrated) within the left atrium 25 as described herein. In some embodiments, the anchor 15*g* may be deployed from the inner shaft 52 by pushing the anchor 15g out of the inner shaft 52, releasing the anchor 15g from radial constraint by retracting the outer sheath 50, or the like as described herein. In some embodiments, the anchor 15g may be pushed out the inner shaft 52 using a pusher on a proximal handle (not shown) located outside the body. After the anchor 15g has been deployed from the delivery device 30', the frame structure 12g may be at least partially deployed from the delivery device 30' as shown in FIG. 43H so as to place the frame structure 12g within the anchor 15g. The frame structure 12g may be deployed from the delivery device 30' in either the unexpanded configuration or the expanded configuration, depending on the location of deployment, as will be understood by one of ordinary skill in the art.

Figure 43J:
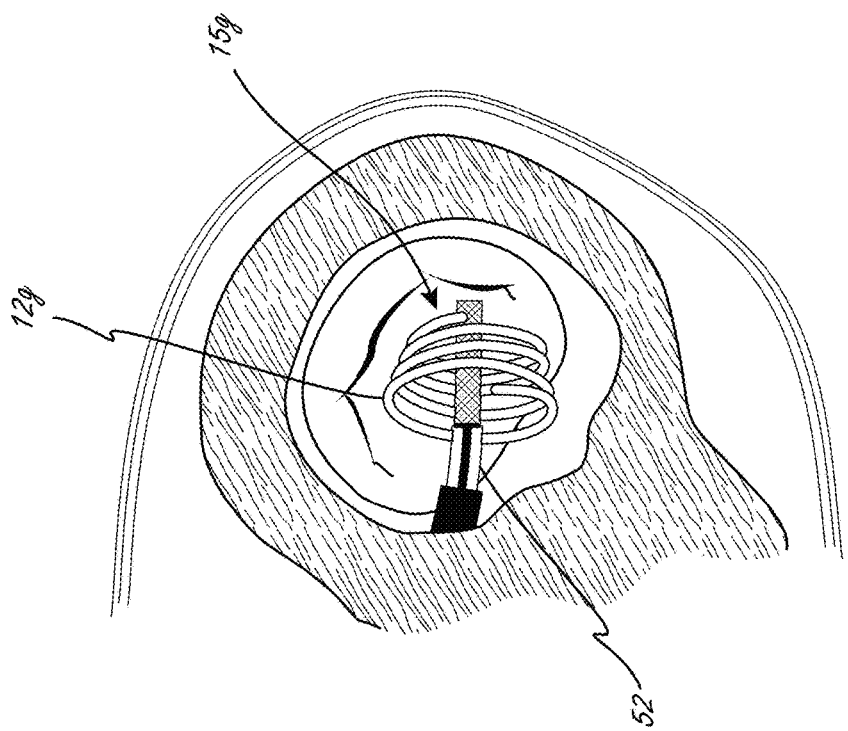
Figure 43I:
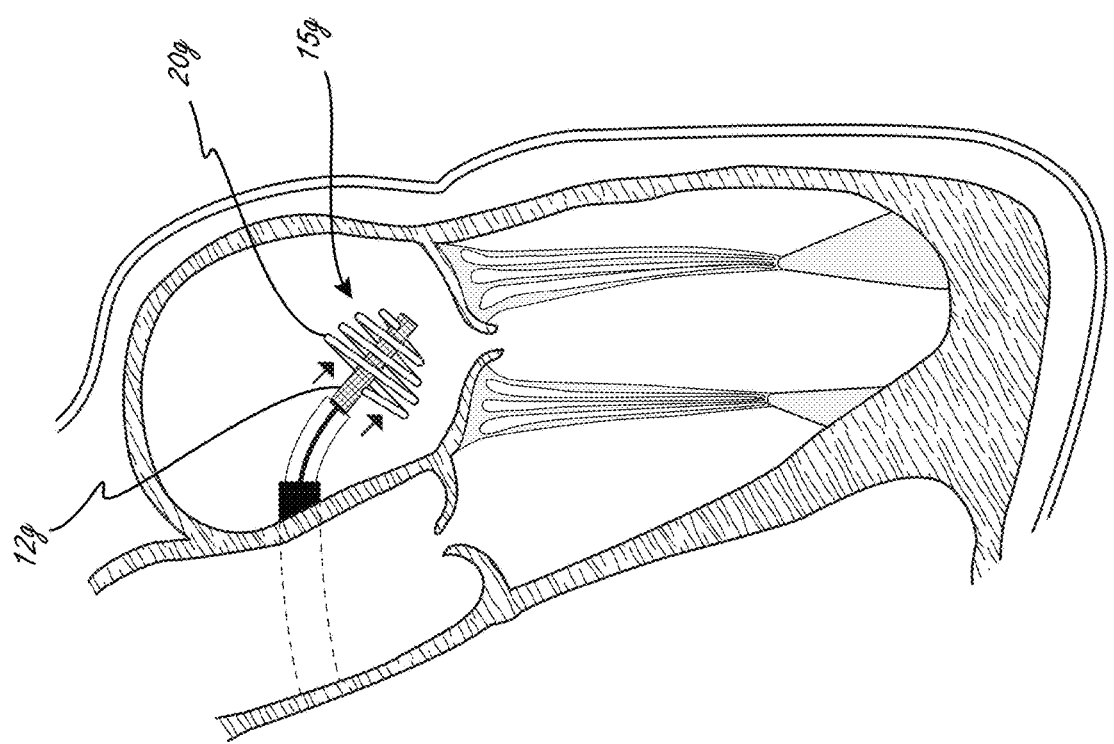
Figure 43L:
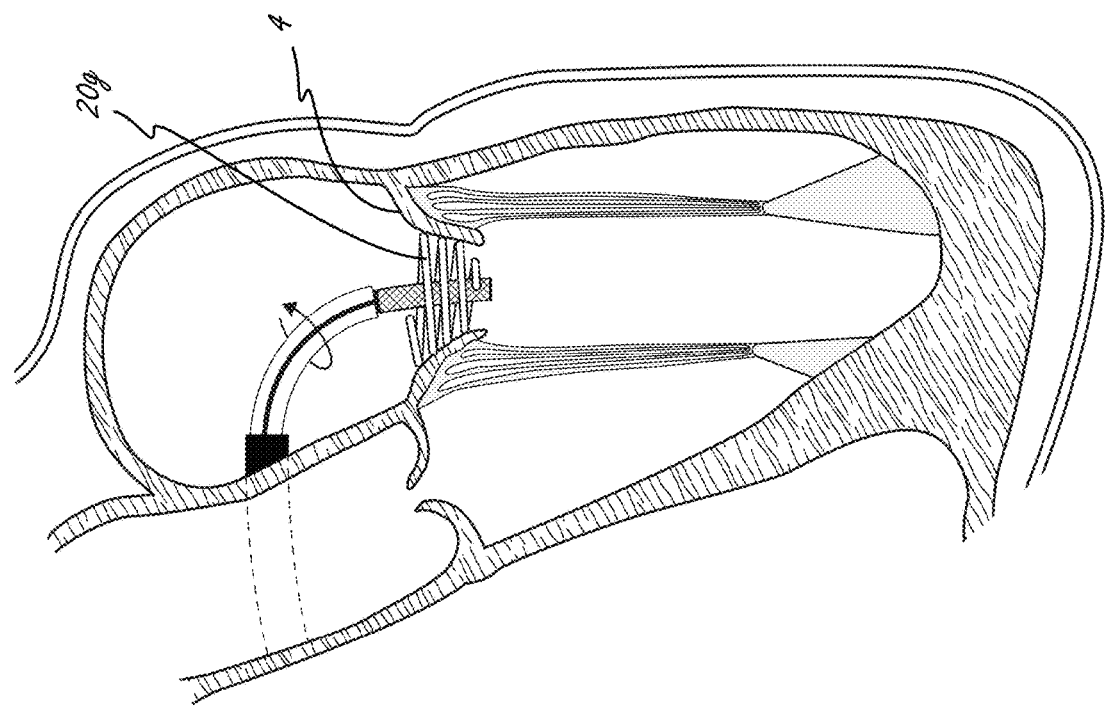
Figure 43K:
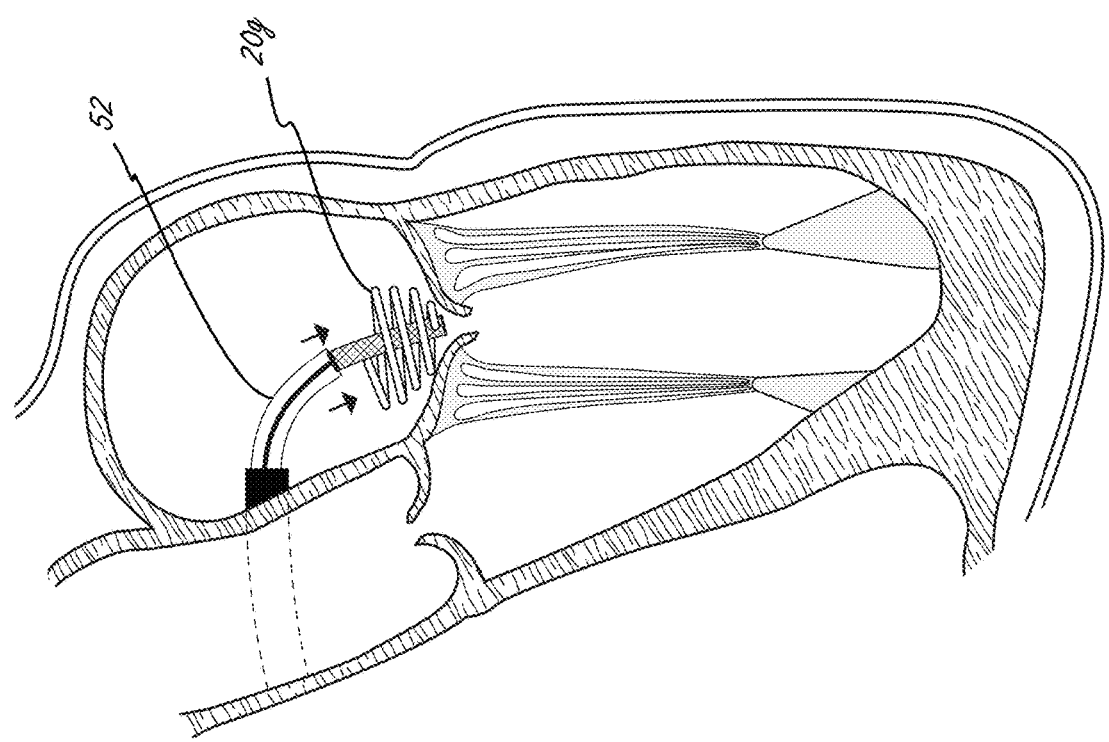

FIGS. 43I-43K show advancement of the valve prosthesis 10g, with anchor 15g deployed around the unexpanded frame structure 12g, towards the native valve 4 requiring treatment. The distal end of the delivery device 30' (for example, the distal end of the inner shaft 52 and/or the outer sheath 50) may be steered such that the distal end of the delivery device 30' points toward the atrial side of the native valve 4. Such steering may occur prior to, during, or after deployment of at least a portion (for example deployment of an anchor 15g) of the valve prosthesis 10g. In some embodiments, the distal end of the outer sheath 50 may be steerable. Alternatively, or in combination, the inner shaft 52 may comprise a joint configured to change an angle of the distal portion of the inner shaft 52 relative to a proximal portion of the inner shaft 52. The inner shaft 52 may be steered by changing the angle of the distal portion of the inner shaft 52 relative to the proximal portion of the inner shaft 52. The angle of the joint may be changed passively or actively. In various embodiments, the angle may be selectively controlled by a proximal handle. For example, pull wires or other mechanisms may connect to the joint to controls on the handle.

FIGS. 43L-43P show the valve prosthesis 10g being advanced through the native valve 4 by the delivery device 30' from the left atrium 25 to the left ventricle 26. Advancement of the valve prosthesis 10g and optionally delivery device 30' through the mitral valve 4 may be facilitated by the natural opening and closing of the valve 4 during the cardiac cycle. The distal end of the delivery device 30' and/or valve prosthesis 10g may be configured to be advanced from a first side of a native valve to a second side of the native valve. For example, the distal end of the delivery device 30' and/or valve prosthesis 10g may be advanced from a left atrial side of a mitral valve 4 to a left ventricular side of a mitral valve 4. Advancing the anchor 15g may comprise pushing the anchor 15g through the native valve 4. Alternatively, or in combination, advancing the anchor 15g may comprise rotating the anchor 15g through the native valve 4. In some instance, the combination of rotational motion and pushing may facilitate advancement of the device from the first side of the native valve 4 to the second side of the native valve 4.

Figure 43N:
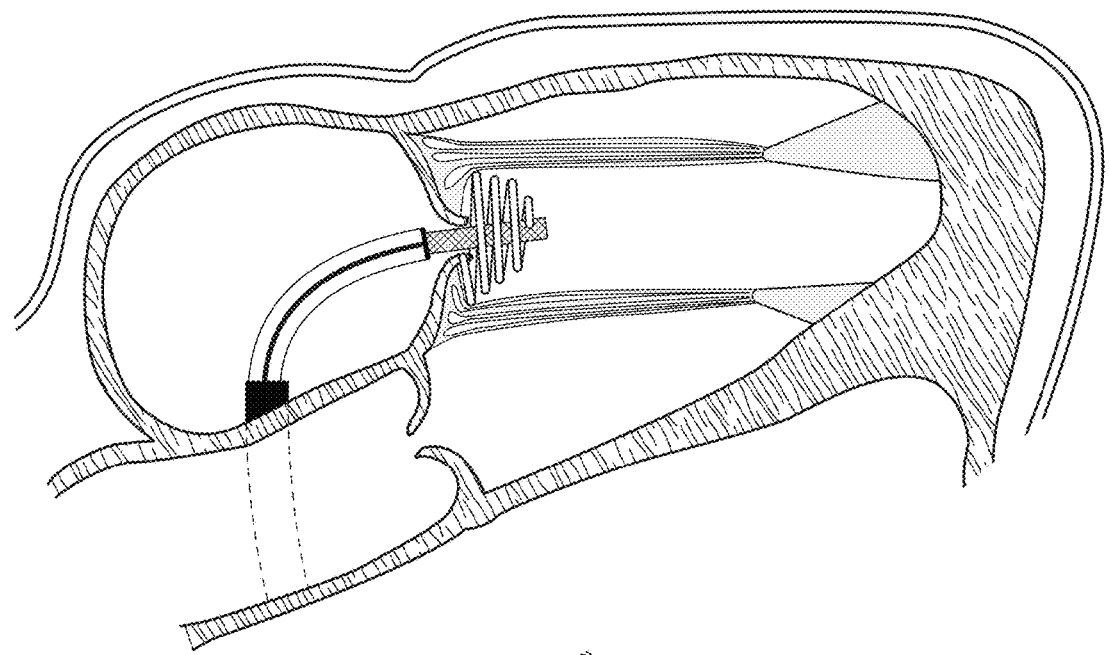
Figure 43M:
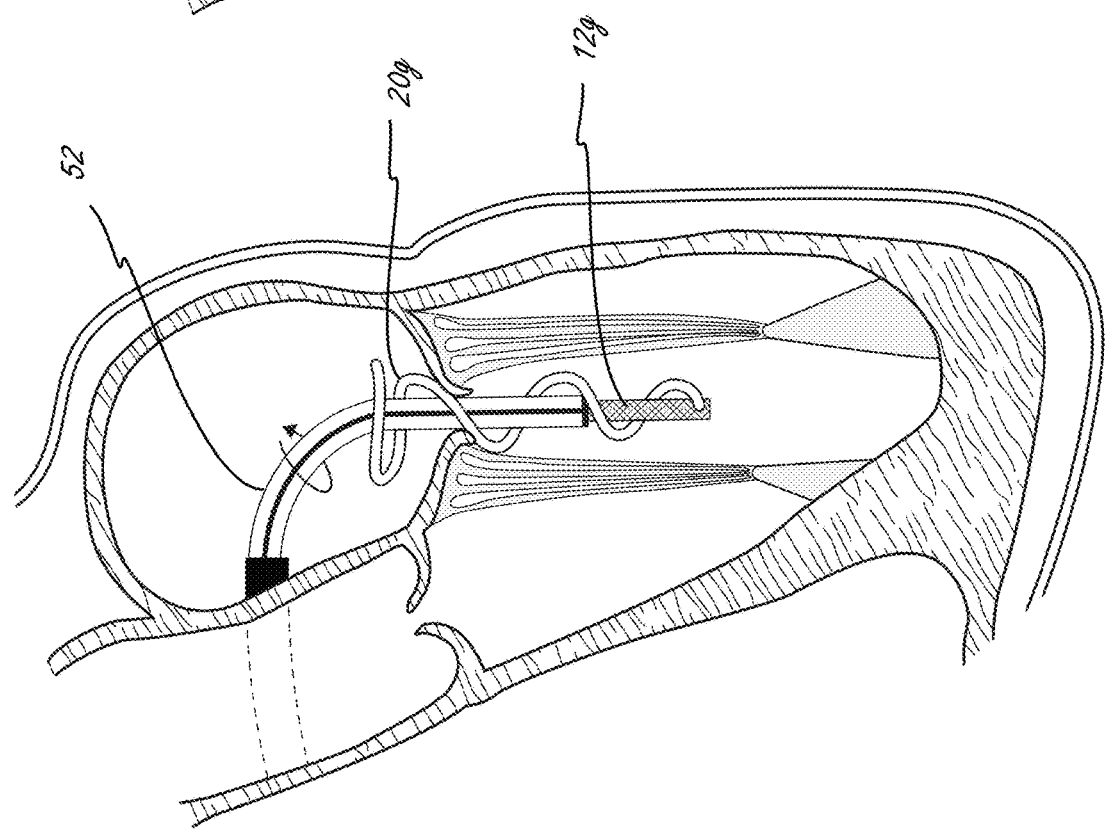
Figure 43P:
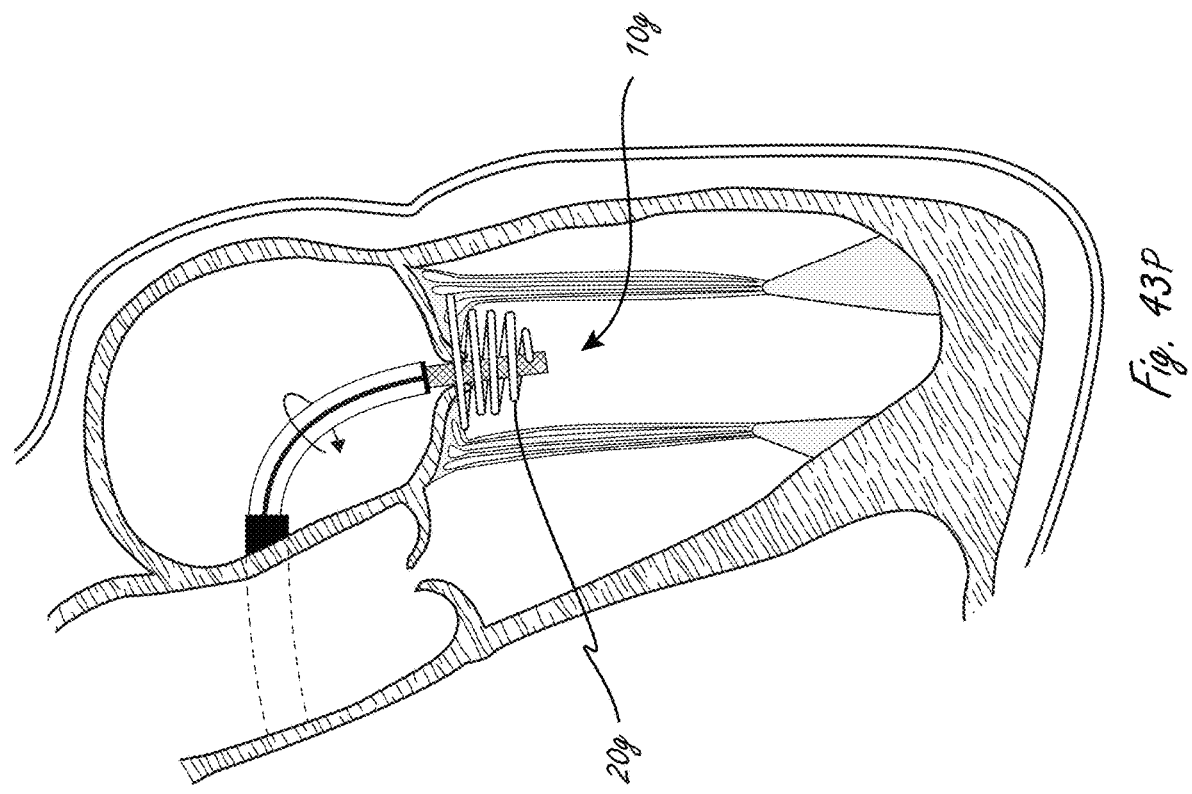
Figure 43O:
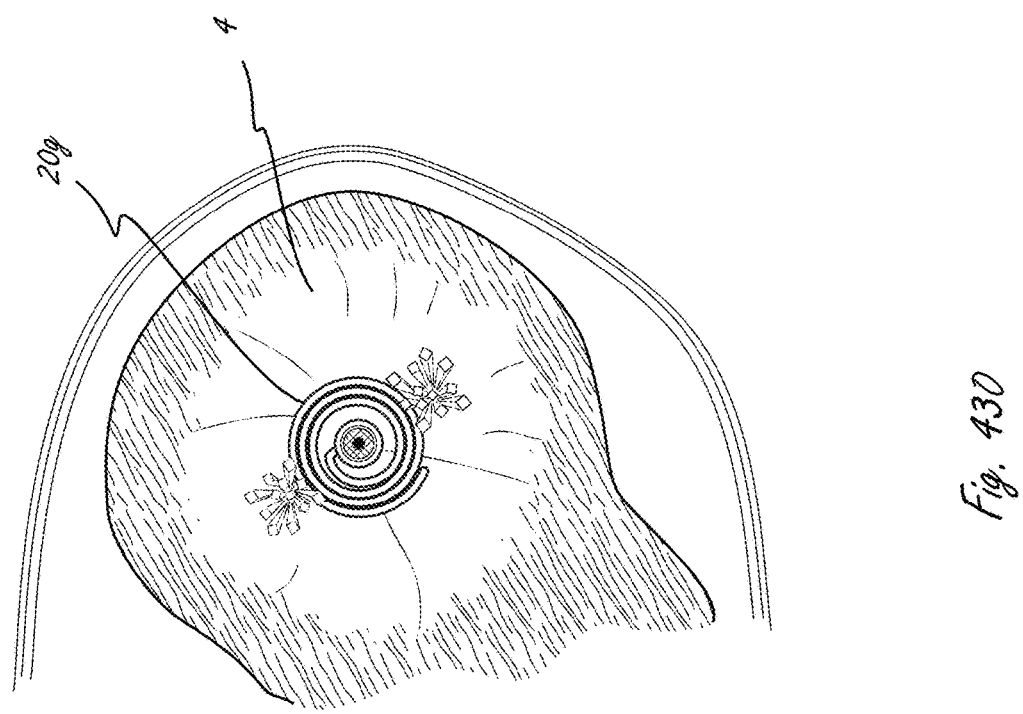

In some instances, advancing the anchor 15g through the native valve 4 may cause the anchor 15g to be stretched or elongated as shown in FIG. 43M. Rotation of the anchor 15g during advancement may assist with the stretching process by aiding in unwinding the anchor 15g. Additionally, the rotational motion may reduce the risk of the free end 22g of the anchor 15g undesirably engaging other anatomy during insertion through the native leaflets 43. The anchor 15g may be sufficiently elastic so as to enable relatively easy insertion through the native valve 4 and/or reduce the risk of injury to the native leaflets 43. After the anchor 15g has stretched through the native valve 4 it may return to the deployed configuration as shown in FIG. 43N. FIGS. 43O-43P show the position of the valve prosthesis 10g within the ventricle 26 and, in particular, the position of the anchor 15g relative to the native chordae tendineae 40 and native valve annulus.

In some embodiments, the anchor 15g may be advanced into the ventricle after being fully deployed from the delivery (e.g., elongated) configuration to the deployed configuration.

In some embodiments, the anchor 15g may be advanced into the ventricle before being deployed from the delivery (e.g., elongated) configuration to the deployed configuration.

Figure 43R:
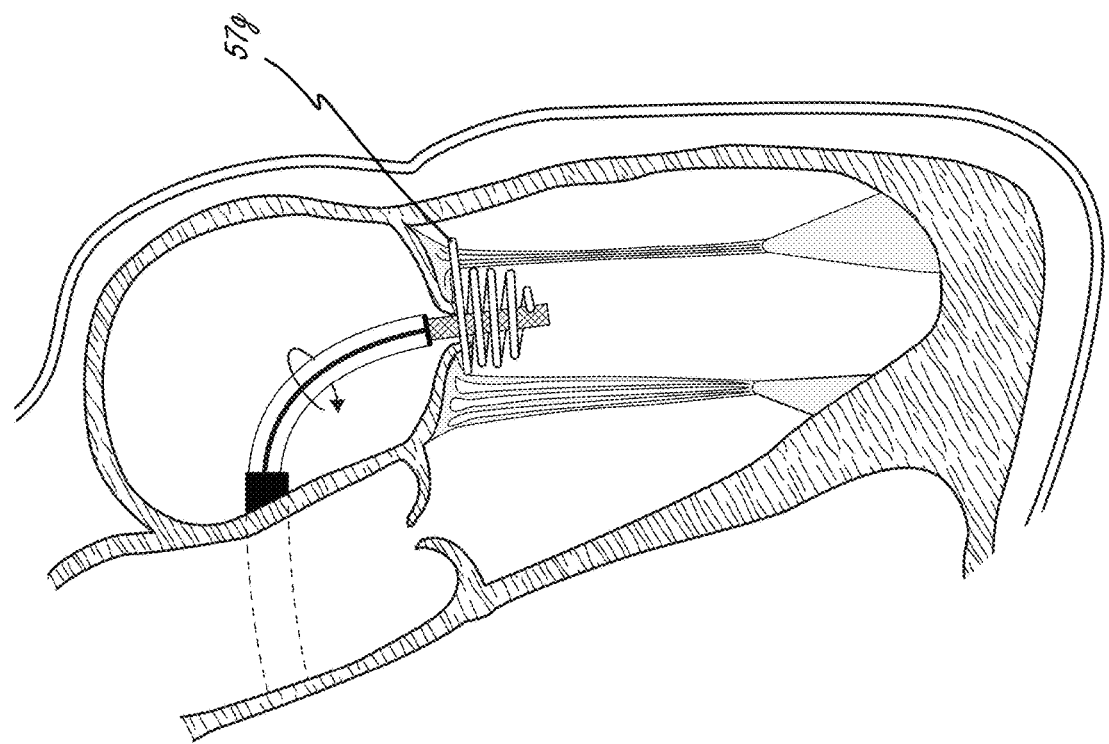
Figure 43Q:
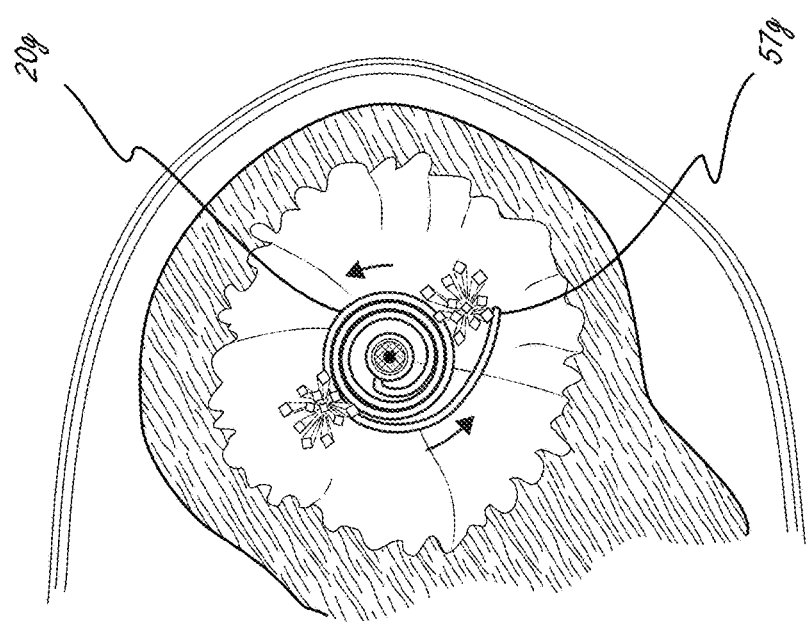
Figure 43T:
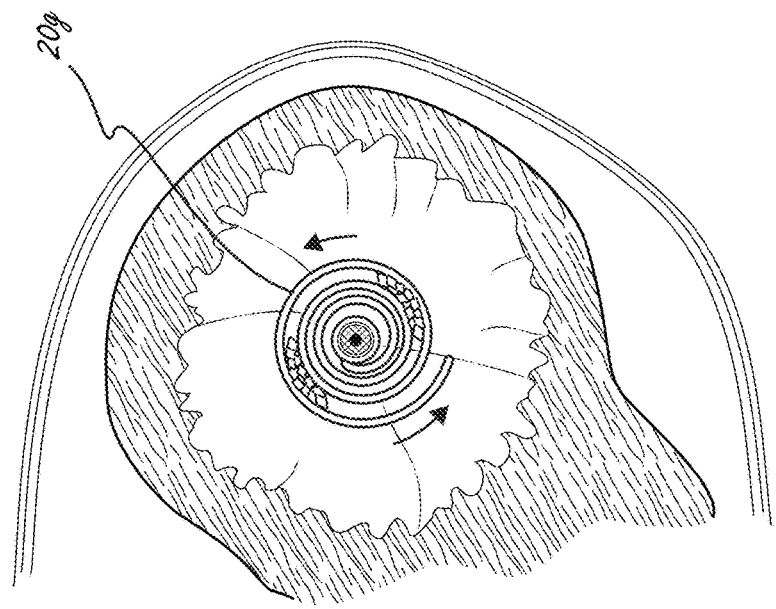
Figure 43S:
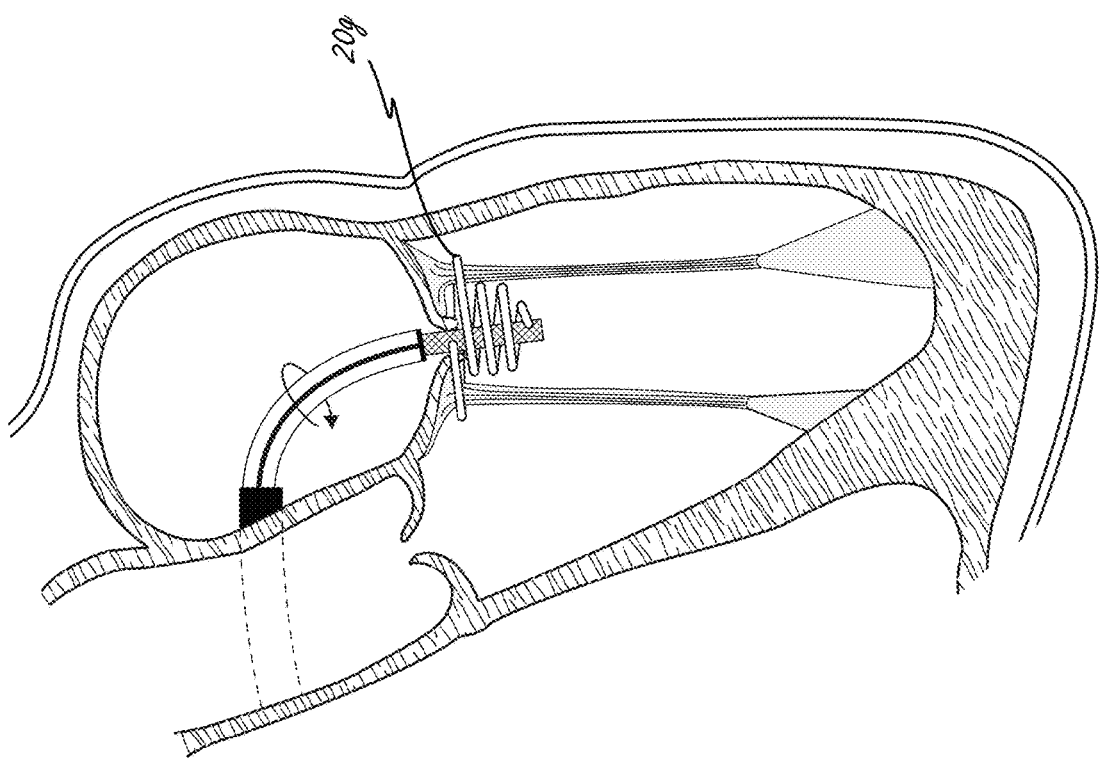

FIGS. 43Q-43T show rotation of the valve prosthesis 10g around one or more structures on the ventricular side of the mitral valve 4. The one or more structures may comprise one or more valve leaflets 43 and/or one or more chordae tendineae 40. After the anchor 15g has been at least partially deployed within the left ventricle 26 adjacent one or more chordae tendineae 40, the valve prosthesis 10g may be rotated to capture and anchor the native chordae 40 and/or native leaflets 43. The free end 22g of the anchor 15g may extend radially outward from the rest of the anchor 15g to facilitate capture of the native structures. The free end 22g of the coil 15g may be rotated around one or more of the chordae tendineae 40 as shown in FIGS. 43Q-43R. Additional rotation of the valve coil 15g may gradually capture additional chordae tendineae 40 as shown in FIGS. 43S-43T.

Rotation of the valve prosthesis 10g, for example, rotation of the anchor 15g and/or frame structure 12, may be facilitated by the delivery device 30' described herein. For example, the inner shaft 52 may be rotated and rotational motion may be transmitted from the inner shaft 52 to the valve prosthesis 10g in order to rotate the valve prosthesis 10g around one or more of the structures on the ventricle side of the mitral valve 4 as described herein.

Figure 43V:
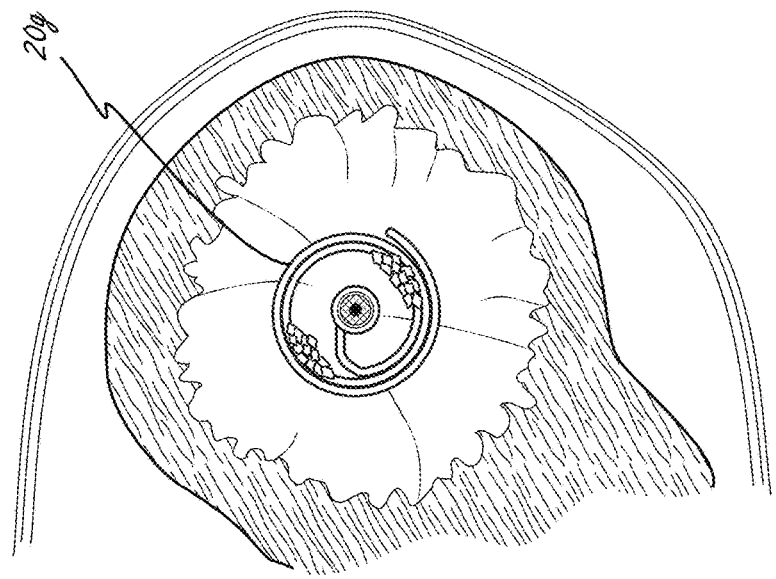
Figure 43U:
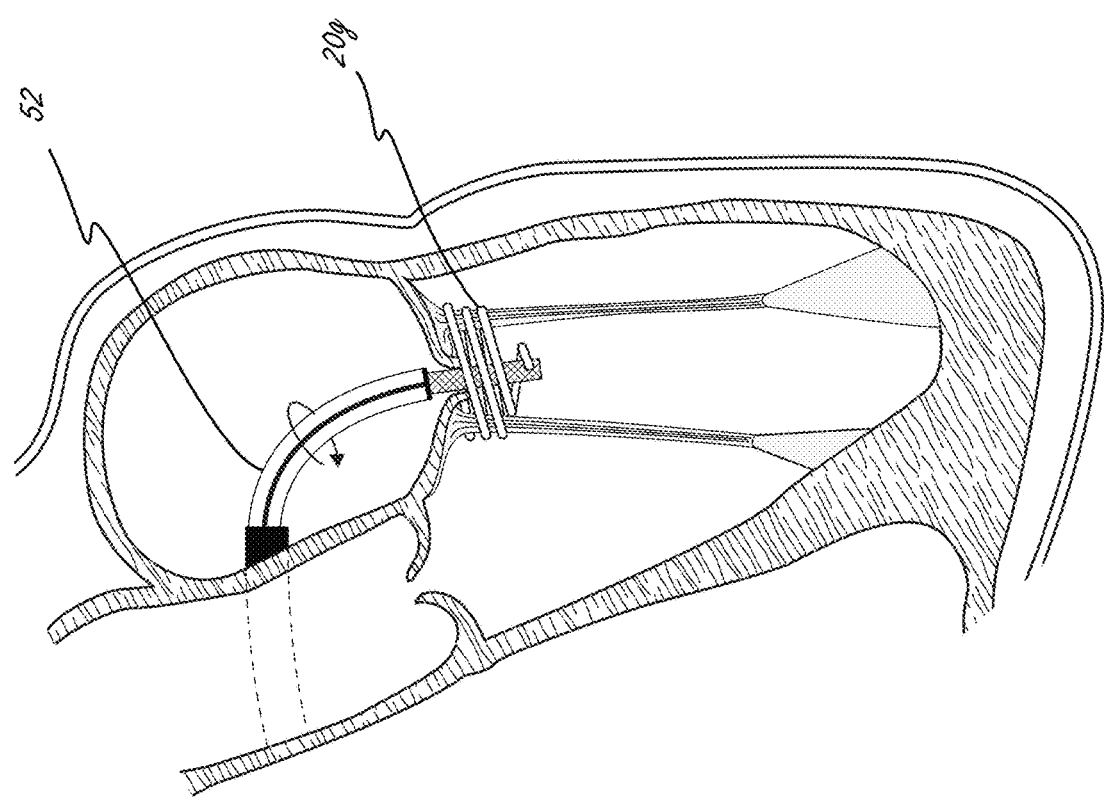

FIGS. 43U-43V show the valve prosthesis 10g wrapped around the captured chordae tendineae 40. The valve prosthesis 10g may be rotated around the chordae tendineae 40 such that the chordae tendineae 40 are pulled inwardly into bunches. As shown in FIG. 43U, the native valve leaflets 43 may also be in communication with the valve prosthesis 10g. The valve prosthesis 10g may be rotated to capture enough chordae tendineae 40 and/or valve leaflets 43 to rigidly anchor the anchor 15g adjacent the native valve annulus. The valve prosthesis 10g may be anchored by wrapping around only a portion of the chordae 40. Although it may be possible to capture all or substantially all the chordae 40, this may not be necessary to provide sufficient anchoring of the prosthesis 10g. As described further herein, the prosthesis may be further anchored by expansion of the frame structure 12g within the native valve and against the anchor 15g.

Once the anchor 15g has been anchored adjacent to the native valve 4, the frame structure 12g and prosthetic valve segment 14 may be expanded at least partially within the anchor 15g as described herein. The frame structure 12g and the valve segment 14g may be deployed (e.g., expanded) simultaneously. Alternatively, or in combination, the frame structure 12g and the valve segment 14g may be deployed sequentially, for example by first expanding the frame structure 12g and then receiving the prosthetic valve segment 14g therein.

Figure 43X:
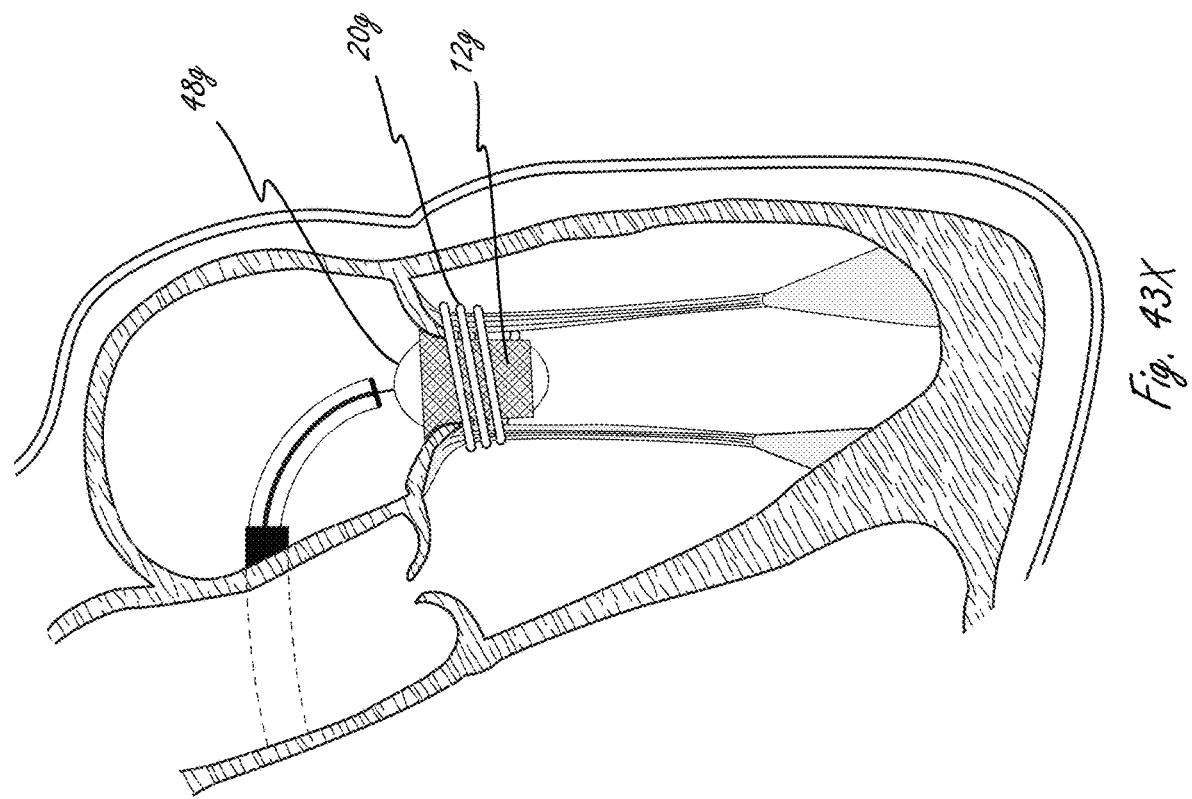
Figure 43W:
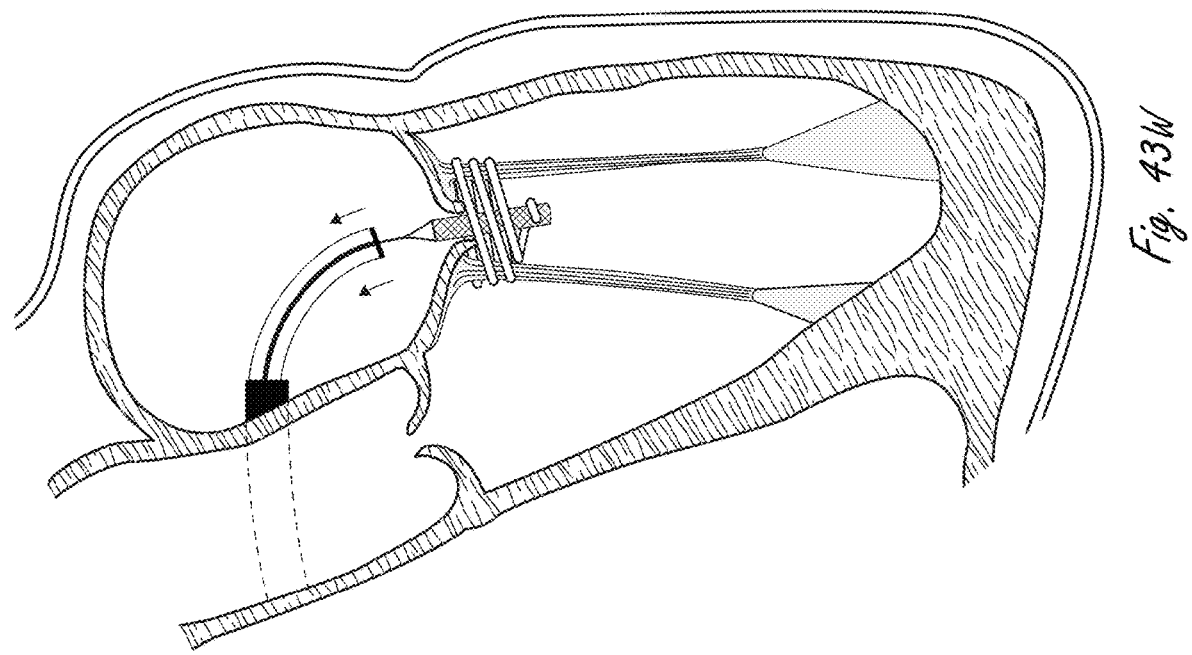
Figure 43Z:
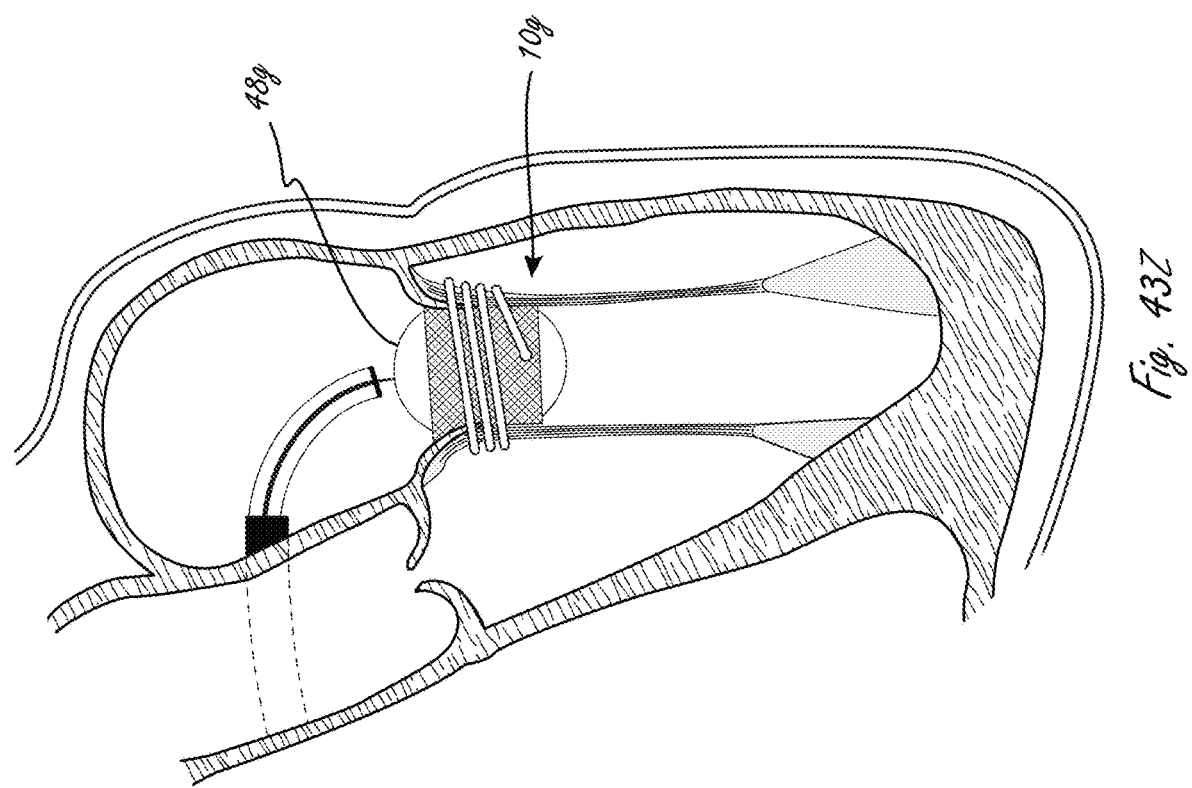
Figure 43Y:
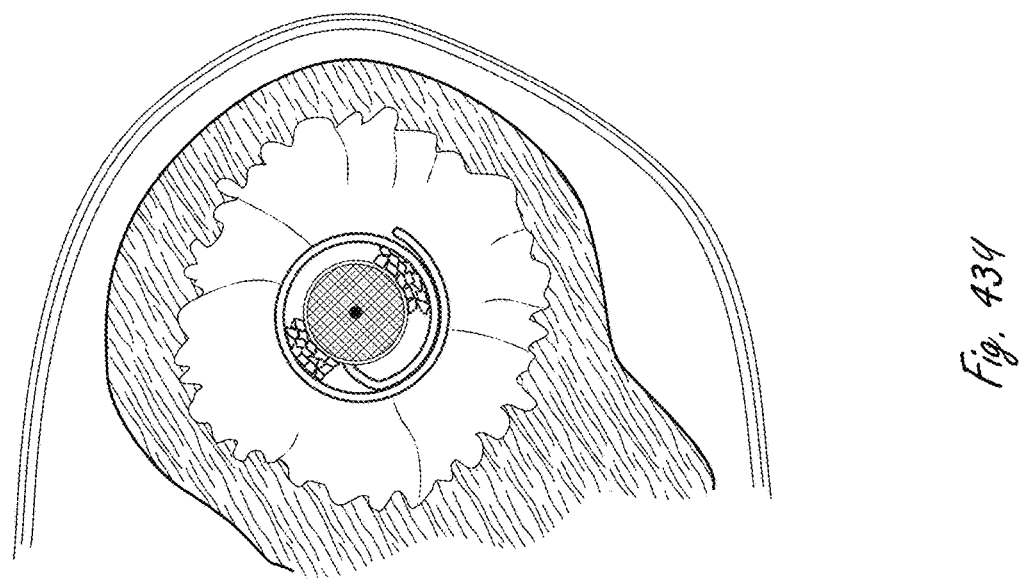
Figure 43A:
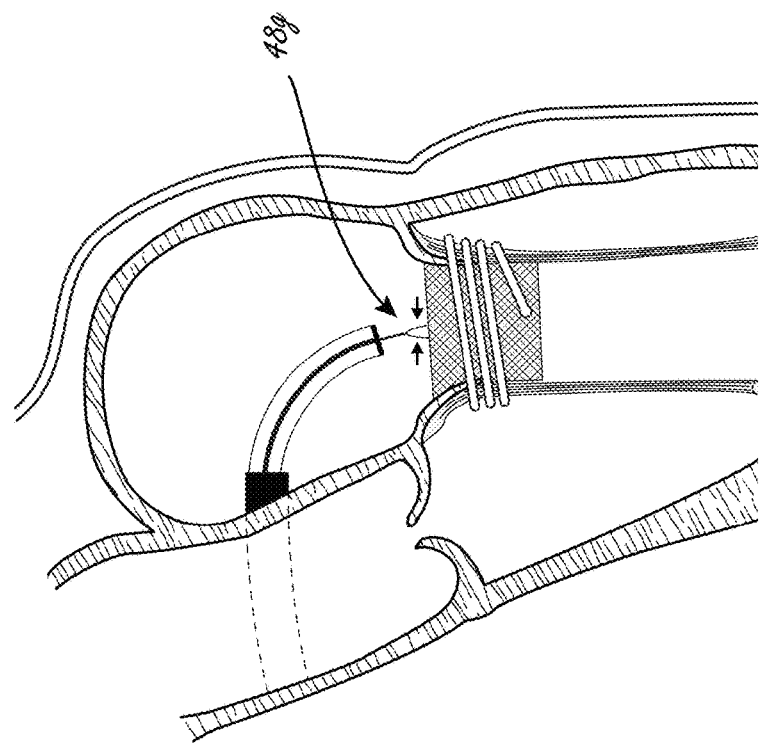
Figure 43A:
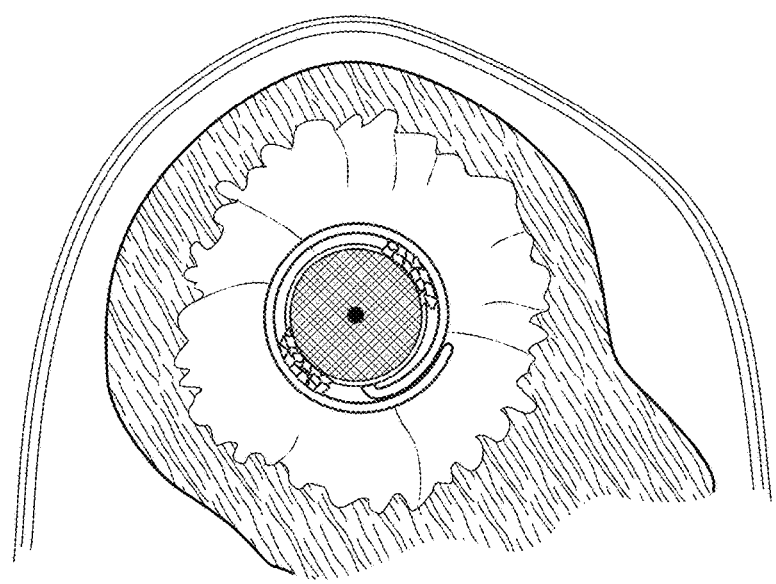
Figure 43A:
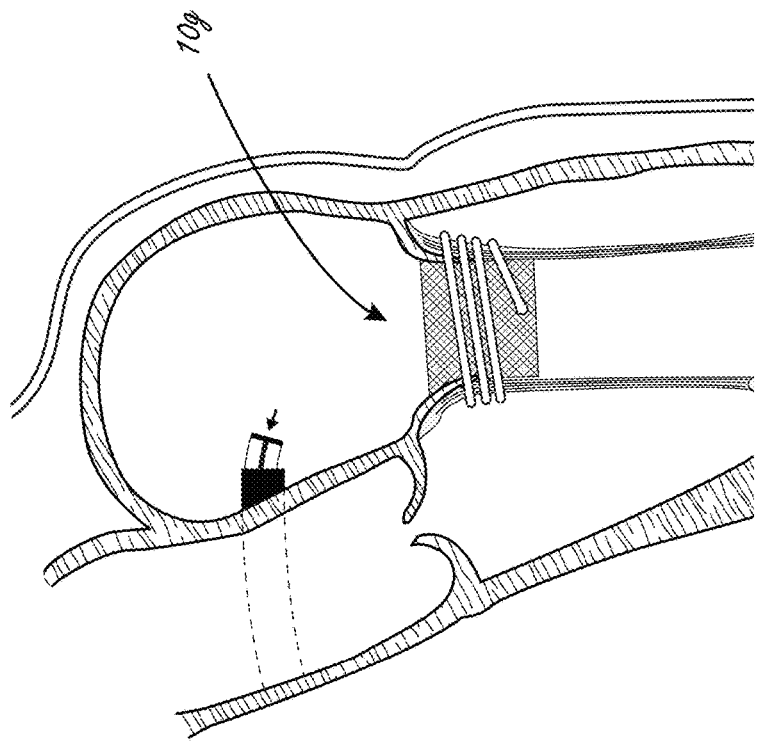
Figure 43A:
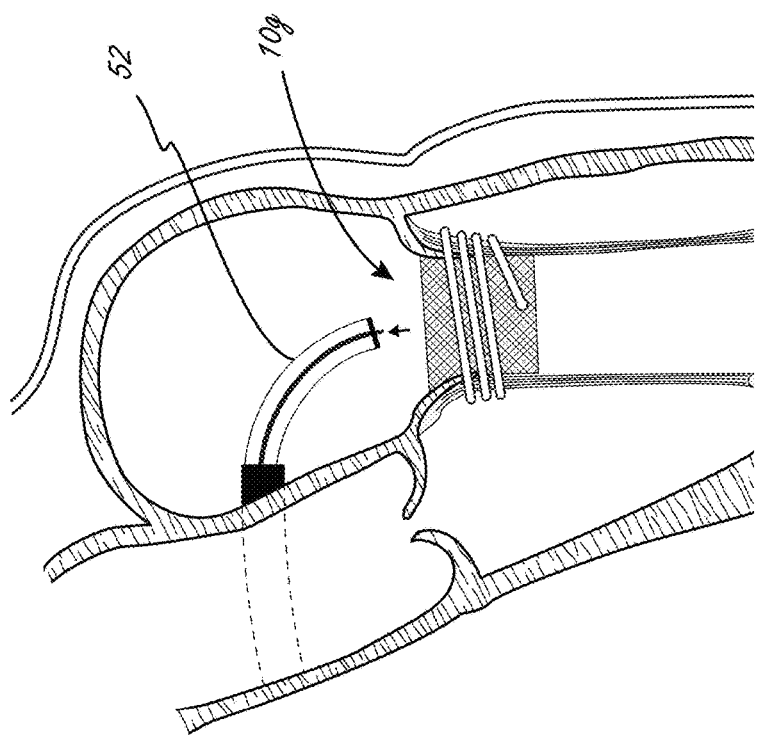
Figure 43A:
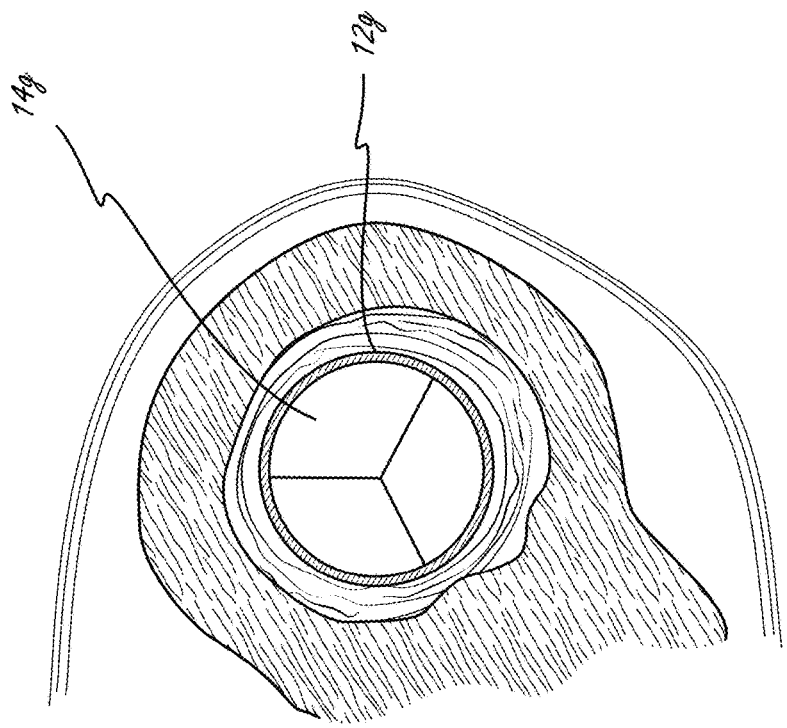
Figure 43A:
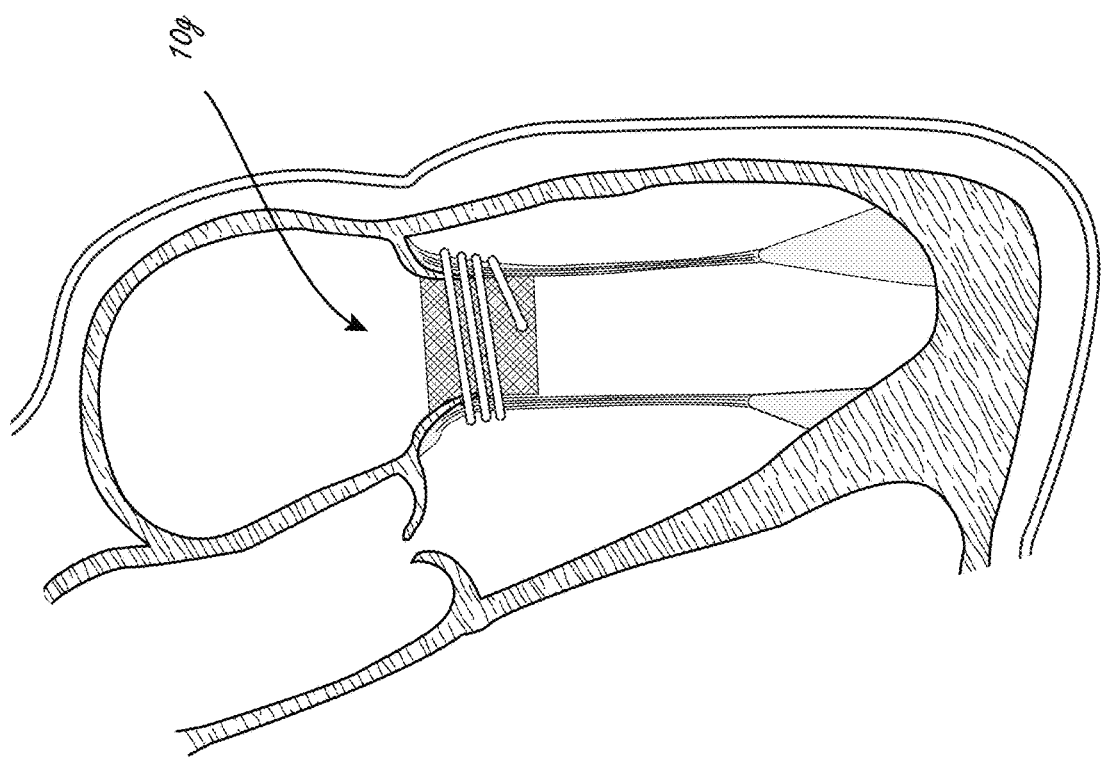
Figure 45:
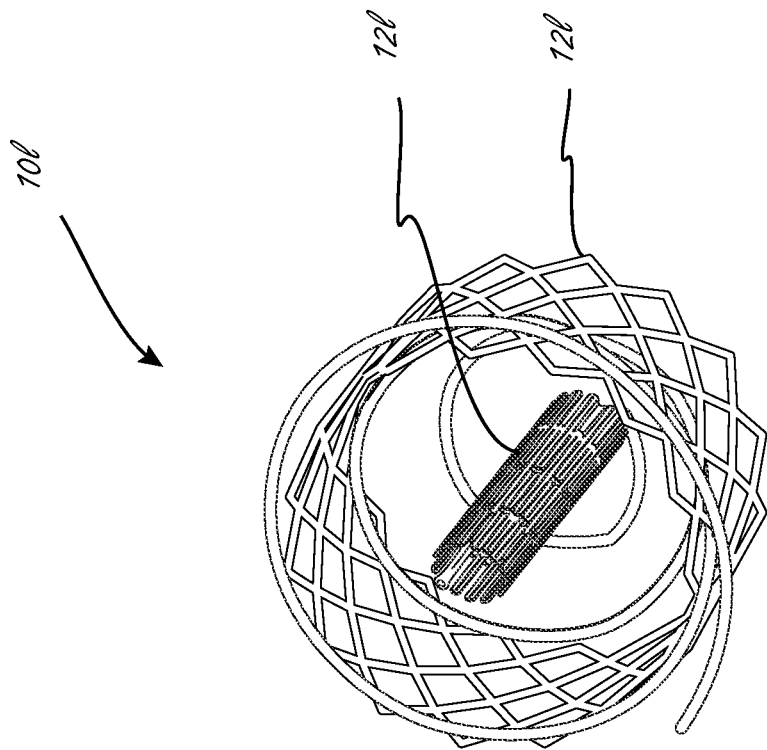
FIGS. 44-49 show a valve device similar to the one of FIG. 6, except that the frame structure is self-expanding, in accordance with embodiments.
Figure 44:
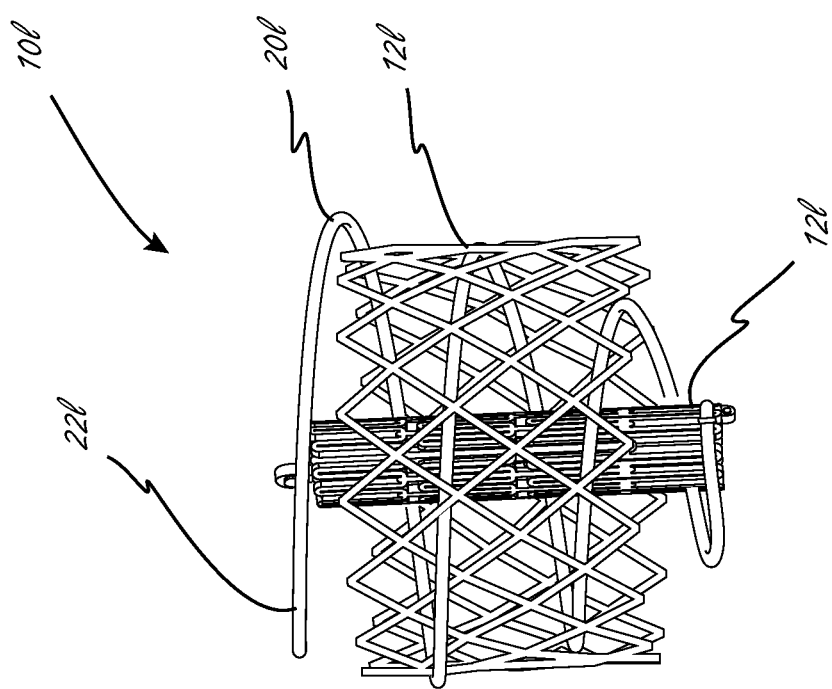
Figure 47:
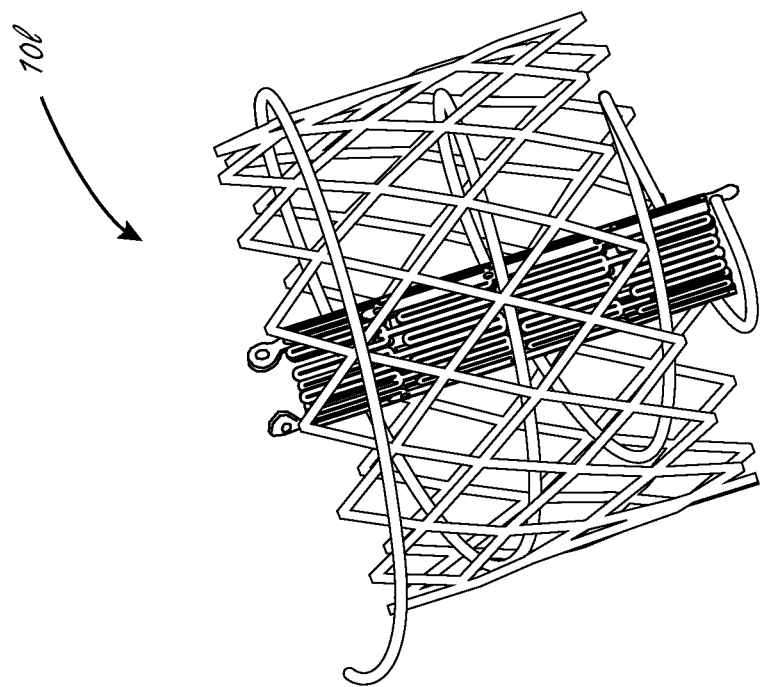
Figure 46:
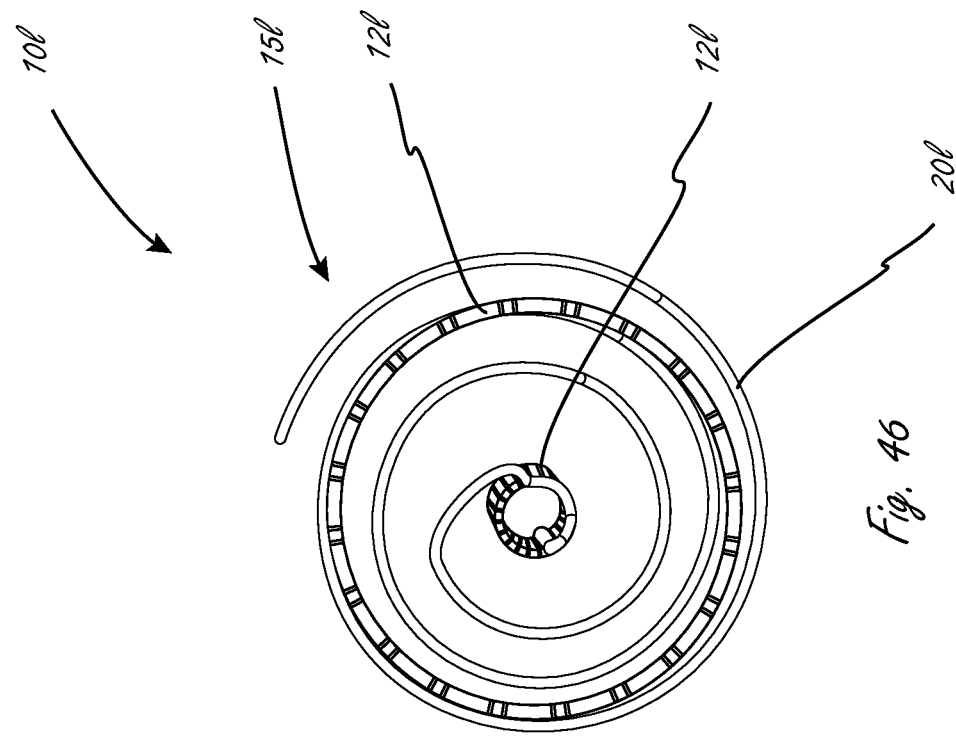

FIGS. 43W-43AA show expansion of the frame structure 12g within the native valve 4. The frame structure 12g may be expanded within the native valve 4 from an unexpanded configuration to an expanded configuration. In some embodiments, at least a portion the frame structure 12g may be expanded within at least a portion of the deployed anchor 15g to anchor the frame structure 12g to the native valve 4. In some embodiments, the frame structure 12g may comprise an expandable stent. In some embodiments, the frame structure 12 of valve prosthesis 10g may be self-expandable. In some embodiments, the frame structure 12 of valve prosthesis 10g may be balloon-expandable. The delivery device 30' may comprise a balloon 48g which may be disposed within the valve prosthesis 10g in order to expand the valve prosthesis 10g. The balloon 48g may be positioned within at least a portion of the valve prosthesis 10g, for example within at least a portion of frame structure 12 in an uninflated configuration, as shown in FIG. 43W, prior to being inflated. The inflatable balloon 48g may, for example, be disposed within the inner shaft 52 or outer sheath 50 while the anchor 15g is being positioned adjacent the native valve 4 and then advanced therefrom (or the inner shaft 52 or outer sheath 50 is retracted therefrom) to be positioned within the frame structure 12g. Alternatively, the inflatable balloon 48g may be disposed within the frame structure 12g during placement of the valve prosthesis 10g. FIGS. 43X-43Y show the frame structure 12g partially expanded by partially-inflated balloon 48g. As shown in FIG. 43Y, the frame structure 12g may be partially expanded towards the anchor 15g in order to capture the chordae tendineae 40 therebetween. As the frame structure 12g continues to be expanded to a fully expanded state, as shown in FIGS. 43Z-43AA, the chordae tendineae 40 may be sandwiched between the anchor 15g and the frame structure 12g. The frame structure 12g and anchor 15g may thus be anchored to the chordae tendineae 40.

The valve prosthesis 10g may then be released from the delivery device 30'. In some embodiments, releasing the valve prosthesis 10g may comprise releasing the anchor 15g and/or the frame structure 12g. Releasing the valve prosthesis 10g from the delivery device 30' may comprise expanding the valve prosthesis 10g from the unexpanded configuration to the expanded configuration. For example, expanding the frame structure 12g and releasing the frame structure 12g may occur simultaneously as described herein. Alternatively, the frame structure 12g may be released prior to or after being expanded.

FIGS. 43AB-43AD show deflation of the balloon 48g (FIG. 43AB), retraction of the balloon 48g into inner shaft 52 (FIG. 43AC), and removal of the delivery device 30' from the heart 2 (FIG. 43AD). After the frame structure 12g has been expanded and anchored to the native valve 4 as described herein, the inflatable balloon 48g may be deflated. The balloon 48g may be retracted back into the delivery device 30', for example into inner shaft 52. The delivery device 30' may then be removed from the heart 2.

FIGS. 43AE-43AF show the valve prosthesis 10g fully expanded with the native valve leaflets 42 and chordae tendineae 40 captured between the frame structure 12g and the anchor 15g. As described herein, the valve prosthesis 10g may comprise one or more valve segments 14g disposed therein to replace the native valve leaflets 42.

Although the steps above show a method of deploying a valve prosthesis 10 within a native valve 4 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

For example, in some embodiments deploying the valve prosthesis 10 may occur in multiple steps such that a portion of the valve prosthesis 10 (e.g., anchor 15) may be deployed before another portion the valve prosthesis 10 (e.g., frame structure 12). Alternatively, or in combination, in some embodiments, deploying the anchor 15 may occur in multiple steps such that a portion of the anchor 15 may be deployed before being advanced through the native valve 4 and another portion of the anchor 15 may be deployed after being advanced through the native valve 4. Alternatively, or in combination, the delivery device 30 may be advanced from the left atrium 25 to the left ventricle 26 with the valve prosthesis 10 undeployed. In many embodiments, the frame structure may 12 be self-expanding and the balloon 48 may not be necessary for expansion of the frame structure 12. Alternatively, or in combination, the anchor 15 may be released after the frame structure 12 has been expanded within it.

In some embodiments, any of the valve prostheses described herein may be deployed to replace a diseased mitral valve. The first side of the native valve may comprise a left atrium and the second side of the native valve may comprise a left ventricle.

In some embodiments, any of the valve prostheses described herein may be deployed to replace a diseased tricuspid valve. The first side of the native valve may comprise a right atrium and the second side of the native valve may comprise a right ventricle.

In some embodiments, any of the valve prostheses described herein may be deployed to replace a diseased aortic valve. The first side of the native valve may comprise a left ventricle and the second side of the native valve may comprise an aorta.

It will be understood by one of ordinary skill in the art that, while FIGS. 43A-43AF refer to delivery of valve prosthesis 10g, similar steps may be used for delivery of any of the valve prosthesis described herein.

FIGS. 44-49 show another exemplary valve prosthesis device 10l which is similar to valve prosthesis devices 10 and 10g-10j except that the frame structure 12l is self-expanding. As shown in FIGS. 44-47, the valve prosthesis 10l includes a helical coil 20l similar to helical coils 20 and 20g. Frame structure 12l is similar frame structures 12 and 12g-12j except that it is configured to expand to the deployed shape upon removal of the sheath of the delivery device. The frame structure 12l is shown in the drawings in both the collapsed and deployed shapes for ease of understanding. The exemplary frame structure 12l may be formed of a shape memory material or any material having superelastic properties. The exemplary frame structure 12l is formed with a diamond pattern, but one of ordinary skill in the art will appreciate from the description herein that many other patterns and configurations will be suitable. The exemplary frame structure 12l is configured to expand in a similar manner to a self-expanding stent or scaffold.

Figure 49:
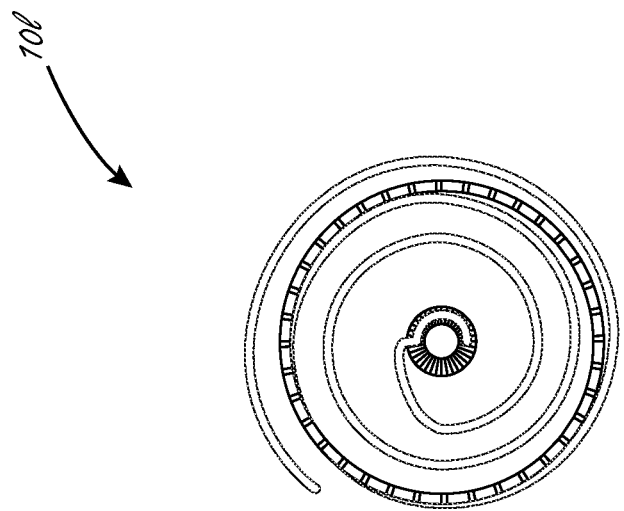
Figure 48:
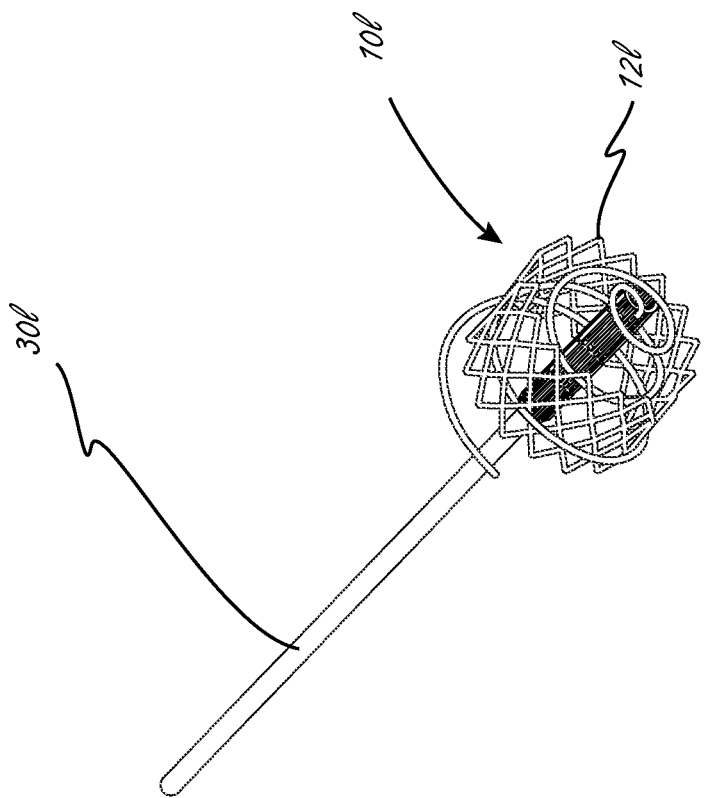

FIGS. 48 and 49 show the exemplary valve prosthesis device 10l loaded on an exemplary delivery tool or catheter 30l. The manner of implanting the valve prosthesis device 10l is similar to the method described herein with respect to valve device 10g except that the frame structure 12l is configured to expand on its own rather than under the force of a balloon. In this case, the frame structure 12l and prosthetic valve segment can be easily deployed in one shot after the coil 15l has been anchored to one or more structures adjacent the native valve. This may reduce the time of the implantation procedure and may eliminate complications like a system for deploying, inflating, and deflating the balloon used in a balloon-expandable embodiment.

The valve prosthesis device and implant method described herein in accordance with the present disclosure may provide many advantages as will be understood by one of ordinary skill in the art. The overall device and method may provide a simpler way to approach the native valve compared to existing devices. The system may enable a transcatheter approach through the septal wall compared to more invasive transapical approaches. The device may provide a consistent and relatively easy mechanism for anchoring to the native valve. Clinicians need only use the common technique of inserting the device through the valve and then rotating the anchor. The coil may provide preliminary anchoring in the native valve. If desired, the clinician can readjust the anchor and/or retrieve the anchor (e.g. by counterrotation). The device is then easily set by expanding within the native valve leaflets. The device and methods in accordance with the present disclosure may also address unmet clinical needs with atrioventricular repair and replacement. Existing devices face challenges with the complex anatomy of the mitral and tricuspid valves, for example. The present disclosures address these complications by reshaping the native valve annulus to a conventional round shape and providing a robust, yet simple, anchoring mechanism.

Figure 50:
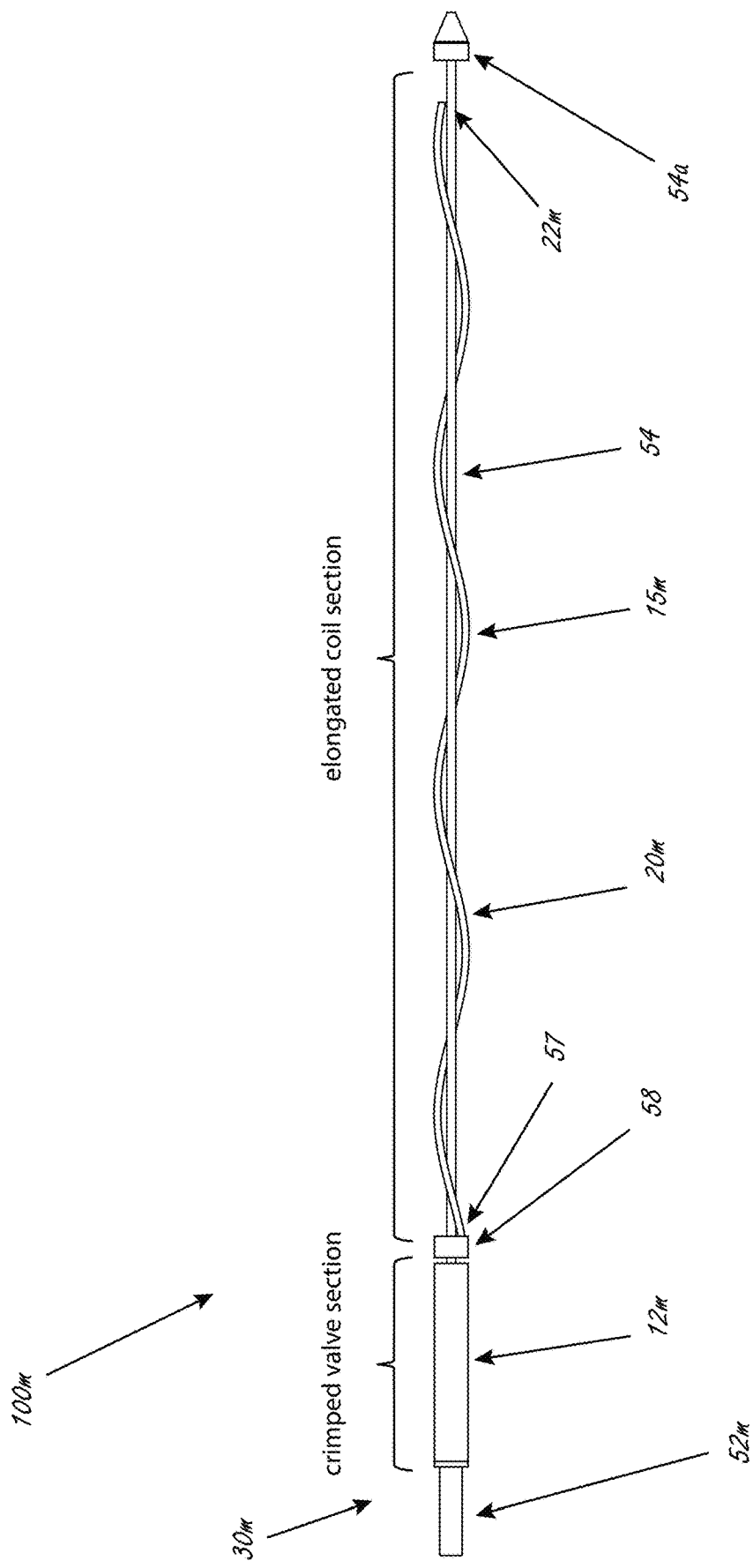
FIG. 50 shows a side view of a valve prosthesis system comprising a frame structure and an anchor loaded on a delivery device with the anchor in an elongated configuration, in accordance with embodiments.
Figure 51:
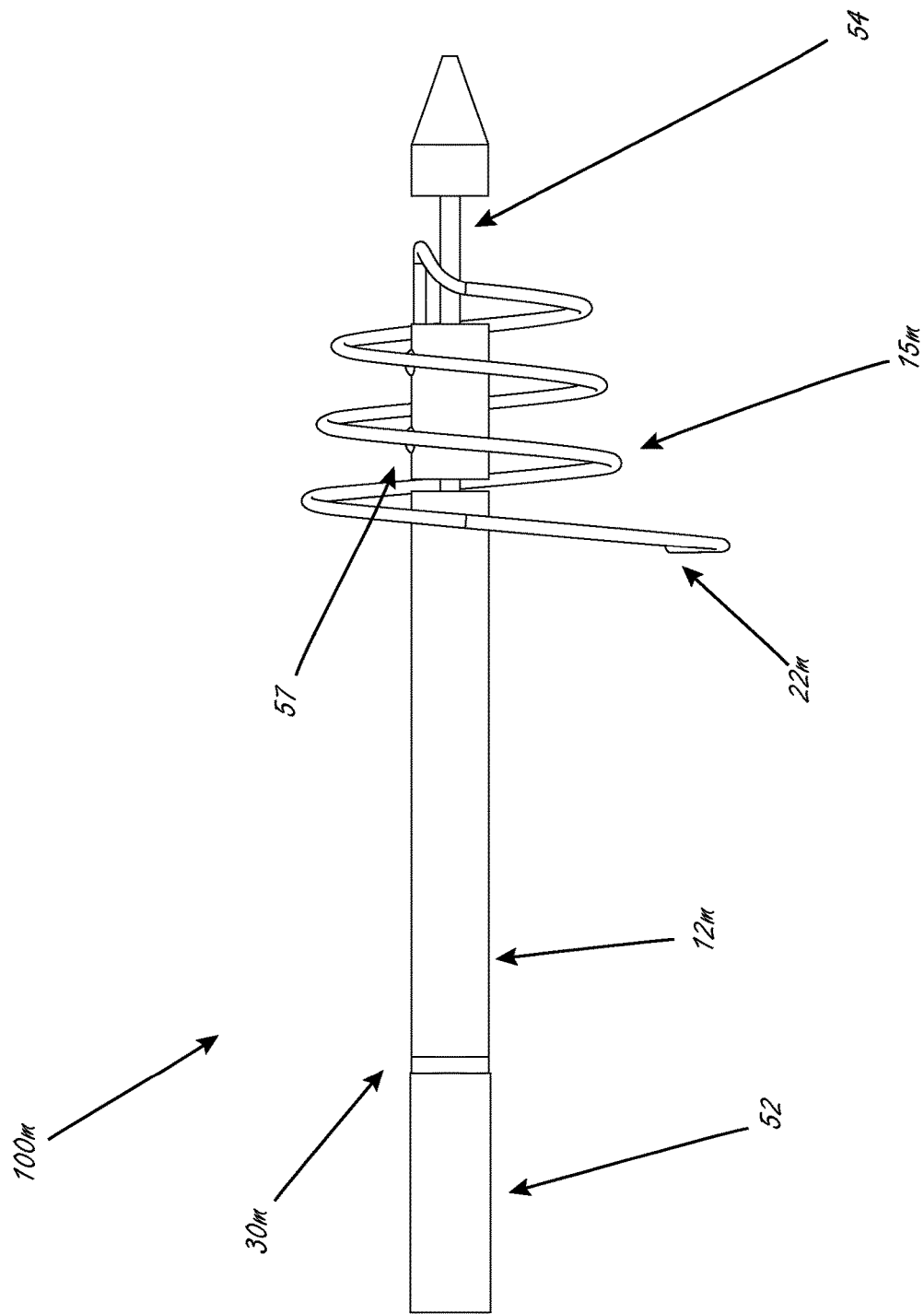
FIG. 51 shows a side view of the valve prosthesis system of FIG. 50 with the anchor in a deployed configuration, in accordance with embodiments.

FIG. 50 shows a side view of a valve prosthesis system 100m comprising a frame structure 12m and an anchor 15m loaded on a distal end of a delivery device 30m with the anchor 15m in an elongated delivery configuration. FIG. 51 shows a side view of the valve prosthesis system 100m of FIG. 50 with the anchor 15m in a deployed configuration. The valve prosthesis may be substantially similar to any of the valve prostheses described herein except that the anchor may be detachably coupled to the delivery device during delivery as described herein instead of the frame structure. By coupling the anchor to the delivery device instead of the frame structure, the frame structure may be expanded inside the anchor without altering the shape or position of the deployed anchor during expansion, which may lead to a better connection between the anchor and the frame structure adjacent the native valve than may have been possible if expansion of the frame structure caused deflection or movement of the deployed anchor.

The frame structure 12m may have an unexpanded (for example, a compressed configuration) and an expanded configuration (not shown). The frame structure 12m is shown in the unexpanded configuration. The anchor 15m may comprise a wire 20m having a free end 22m. The anchor 15m may be configured to be fully advanced from a first side of a native valve in a patient (e.g. an atrial side) to a second side of the native valve (e.g., into a ventricle of the heart) and anchor the frame structure 12m to the native valve when the frame structure 12m is in the expanded configuration adjacent the native valve. The delivery device 30m may comprise an outer sheath (e.g. an outer catheter, not shown), an inner shaft 52 (e.g., a delivery tube) disposed within a lumen of the outer sheath, and a guidewire 54 disposed within a lumen of the inner shaft 52. A proximal end 57 of the anchor 15m may be detachably coupled to the inner shaft 52 during delivery to the native valve. The outer sheath may be steerable.

The anchor 15m may comprise an elongated delivery configuration (shown in FIG. 50) and a deployed configuration (shown in FIG. 51). The anchor 15m may be configured to be actuated from the delivery configuration to the deployed configuration adjacent the native valve. In various embodiments, the anchor 15m may be self-expanding and may move to the deployed configuration as it is removed from the delivery sheath. In various embodiments, the anchor may be configured to self-assemble when it is deployed in the heart cavity (e.g. in a left atrium). Retraction of the guidewire 54 into the lumen of the inner shaft 52 may actuate the anchor 15m into the deployed configuration. Alternatively, or in combination, the anchor 15m may be maintained in the elongated configuration by radial constriction from the outer sheath. Advancement of the inner shaft 52 out of the lumen of the outer sheath may actuate the anchor 15m into the deployed configuration.

A proximal end 57 of the anchor 15m may be detachably coupled to the inner shaft 52 of the delivery device 30m. The proximal end 57 may be configured to remain engaged with the inner shaft 52 after being actuated from the elongated configuration to the deployed configuration adjacent the native valve. The frame structure 12m may be configured to remain in its unexpanded configuration while the anchor 15m is in the deployed configuration.

The proximal end 57 of the anchor 15m may be detachably coupled to the inner shaft 52 of the delivery device 30m by radial constriction from the outer sheath. Retraction of the outer sheath away from the proximal end 57 of the anchor 15m may detach the anchor 15m from the delivery device 30. Alternatively, or in combination, the proximal end 57 of the anchor may be detachably coupled to the inner shaft 52 of the delivery device 30m by an attachment element 58. Alternatively, or in combination, the proximal end 57 of the anchor 15m may be detachably coupled to the inner shaft 52 of the delivery device 30m by a weak adhesive.

The anchor 15m may be configured to rotate when the inner shaft 52 is rotated. Rotation of the anchor may aid in advancement of the anchor to the second side of the native valve. Alternatively, or in combination, rotation of the anchor, for example a wire 20m comprising a free end 22m, may aid in capture of one or more structures on the second side of the native valve by the free end 22m as described herein. By capturing one or more structures on the second side of the native valve, the anchor 15m may maintain its position relative to the native valve and provide an anchor point for the frame structure 12m when in the expanded configuration.

The frame structure 12m may comprise an unexpanded configuration and an expanded configuration as described herein. The expanded configuration may have a generally tubular expanded shape. The frame structure 12m may be configured for expanding within the native valve of the patient. In some embodiments, the unexpanded configuration may be sized and dimensioned for percutaneous insertion and the expanded configuration may be sized and dimensioned for implantation in the native valve of the patient.

Similar to the other frame structures described herein, the frame structure 12m may comprise a first and second opposite ends, the first end extending above a native valve and the second end extending below the native valve when the frame structure 12m is anchored to the native valve. Alternatively, the frame structure 12m may be configured to sit entirely below the native valve when the frame structure 12m is anchored to the native valve.

In some embodiments, similar to other frame structures described herein, the frame structure may comprise an expanded outer periphery in the expanded configuration and a compressed outer periphery when subject to an external radial force in the unexpanded configuration. The compressed outer periphery may be smaller in diameter than the expanded outer periphery.

The frame structure 12*m* may be balloon-expandable, self-expanding, or otherwise expansible as will be understood by one of ordinary skill in the art from the description herein.

For example, the delivery system 30*m* may comprise an inflatable balloon (not shown) disposed within the frame structure 12*m*. Inflation of the balloon may cause expansion of the frame structure 12*m* as described herein.

Alternatively, or in combination, the frame structure 12*m* may be maintained in the unexpanded configuration by radial constriction from the outer sheath of the delivery device 30*m*. Advancement of the inner shaft out of the lumen of the outer sheath may actuate the frame structure into the expanded configuration.

The frame structure 12*m* may be detachably coupled to the delivery device 30*m* in the unexpanded configuration during delivery to the native valve. Expansion of the frame structure 12*m* to the expanded configuration may detach the frame structure from the delivery device.

Similar to other frame structure and anchor embodiments described herein, at least a portion the frame structure 12*m* may be expanded within at least a portion of the deployed anchor 15*m* to anchor the frame structure 12*m* to the native valve. For example, the anchor 15*m* may be deployed such that it captures one or more structures therein, for example one or more chordae tendineae and/or one or more valve leaflets. Expansion of the frame structure 12*m*, or a portion thereof, within the anchor 15*m* may compress the capture structures between the frame structure 12*m* and the anchor 15*m* to anchor the frame structure 12*m* in place.

The guidewire 54 may comprise a nosecone 54*a* configured to facilitate guidance of the guidewire to the native valve.

Similar to other wires described herein, the wire 20*m* may comprise a helical wire in the deployed configuration. The free end 22*m* of the helical wire 20*m* may extend radially outward from the frame structure 12*m*, and in particular from the remainder of the wire 20*m*. In some embodiments, the helical wire 20*m* may have a generally tubular shape. The free end 22*m* of the helical wire 20*m* may extend radially outward from the tubular shape. In some embodiments, the helical wire 20*m* may have a generally frustoconical shape. The free end 22*m* of the helical wire 20*m* may extend radially outward from the frustoconical shape. In some embodiments, the helical wire 20*m* may have a generally cylindrical shape. The free end 22*m* of the helical wire 20*m* may extend radially outward from the cylindrical shape. The free end 22*m* may be configured to encircle a larger radius than the main coils of the helical wire 20*m*. The larger diameter may facilitate capturing of one or more structures, for example the valve leaflets of the chordal tendineae within the sweep of the free end 22*m* when rotated as described herein.

Optionally, the anchor 15*m*, or any of the anchors described herein, may comprise a first portion comprising the helical wire 20*m* and another portion. Alternatively, or in combination, the anchor 15*m* may comprise a plurality of helical wires 20*m*. For example, the anchor 15*m* may comprise at least two helical wires 20*m* having the same or different diameters. Alternatively, or in combination, the anchor 15*m* may comprise at least two helical wires 20*m* having the same or different winding pitches.

As with other anchors described herein, the free end 22*m* of the wire 20*m* may be sized and dimensioned for insertion through the native valve, for example through tissue at or near a commissure of the native valve or through the valve opening itself. In some embodiments, the free end 22*m* of the wire 20*m* may comprise an atraumatic tip to avoid reduce risk of injury to the native valve tissue and leaflets. For example, the free end may comprise a blunt end, a ball tip, a curved tip (e.g. J-tip or pigtail), or other atraumatic shapes. Alternatively, the free end 22*m* of the wire 20*m* may be configured for piercing tissue.

Wire 20*m*, or any of the wires described herein, may be formed of a material having sufficient rigidity to hold a predetermined shape. The wire may, for example, be formed of a shape memory material (e.g. NiTi). It may be desirable for at least an end portion (e.g. free end 22*m*) to be relatively rigid such that it can exert a force to move chordal tendineae, while still retaining flexibility to be collapsed within a delivery device. In various embodiments, the end portion only needs sufficient rigidity to hold its shape and will deform under a load. For example, the end portion may be configured with a similar rigidity to a guidewire, or slightly stiffer.

The frame structure 12*m*, or any of the frame structures described herein, may be configured like a stent. The frame structure 12*m* may, for example, comprise a scaffold in a diamond pattern formed from a shape memory material (e.g. NiTi). One of ordinary skill in the art will appreciate that many other structures, materials, and configurations may be employed for the frame structure 12*m*, or any of the other frame structures described herein. For example, the frame structure 12*m* may be formed of a polymer of sufficient elasticity. The frame structure 12*m* may be formed of a combination of metal and polymer, such as metal (e.g. shape memory material) covered in polymer. The frame structure 12*m* may include a variety of patterns besides diamond shapes.

The frame structure 12*m*, or any of the frame structures described herein, may comprise a valve segment (not shown) disposed therein. As described above, valve segment is used somewhat interchangeably with prosthetic valve leaflet and generally refers to the prosthetic leaflets and frame. As used herein, "prosthetic valve" may refer to all manner of prosthetic and artificial replacement valves including tissue (biological valves), tissue-engineered valves, polymer valves (e.g. biodegradable polymer valves), and even certain mechanical valves. The valve segment can be similar to existing transcatheter valves. The valve segment can be similar to existing surgical tissue valves, and mechanical valves. At least a portion of the valve segment may be positioned within at least a portion of the frame structure. The valve segment may include leaflets formed of multi-layered materials for preferential function. The valve segment may comprise at least one leaflet having an inner layer and an outer layer. The valve segment may be attached to a valve structure which is in turn connected to the frame structure 12*m*. The valve structure may be connected to the frame structure 12*m* before or after the frame structure 12*m* has been deployed adjacent a native valve. The valve segment may be attached directly to the frame structure 12*m*. The frame structure 12*m* may be attached to a leaflet, for example an outer layer of a leaflet, at one or more ends of the frame structure 12*m*. The frame structure 12*m* may be attached to a leaflet, for example an outer layer of a leaflet, at one or more intermediate portions of the frame structure 12*m*. The valve segment may comprise a plurality of leaflets. The valve segment may comprise a biocompatible one-way valve. Flow in one direction may cause the leaflet(s) to deflect open and flow in the opposite direction may cause the leaflet(s) to close.

One of ordinary skill in the art will recognize based on the description herein that any of the valve prostheses described herein may comprise any of the frame structure shapes, frame structure designs, frame structure materials, anchor shapes, anchor windings, anchor materials, free end tips, leaflet(s) configurations, or any other of the variable features described herein in any combination thereof as desired.

Method of Use

The distal end of the delivery device 30m may be configured to be advanced from a first side of a native valve to a second side of the native valve. For example, the distal end of the delivery device 30m may be advanced from a left atrial side of a mitral valve to a left ventricular side of a mitral valve. In some instances, the distal end of the delivery device 30m may be transseptally inserted into the left atrium of the heart prior to advancement into the left ventricle. Alternatively, or in combination, the distal end of the delivery device 30m may be steerable such that it is positionable to point towards the first side of the native valve before being advanced to the second side of the native valve.

After advancing to the second side of the native valve, the anchor 15m may be fully deployed on the second side of the native valve. Fully deploying the anchor 15m may comprise actuating the anchor 15m from an elongated configuration to a deployed configuration as shown in FIG. 51.

In some embodiments, fully deploying the anchor 15m may comprise actuating the anchor 15m from an elongated configuration to a deployed configuration on the first side of the native valve (e.g., in the left atrium) and advancing the anchor 15m, in the deployed configuration, through the native valve to the second side of the native valve (e.g., into the left ventricle). Advancing the anchor 15m may comprise pushing the anchor 15m through the native valve as described herein. Advancing the anchor 15m may further comprise rotating the anchor 15m through the native valve.

In some embodiments, fully deploying the anchor 15m may comprise positioning the anchor 15m such that it is located only on the second side of the native valve.

In some embodiments, the anchor 15m may be actuated from the delivery configuration to the deployed configuration on a first side of the native valve prior to being advanced to a second side of the native valve. For example, the anchor 15m may be fully deployed in a left atrium of a heart prior to being advanced to a left ventricle of the heart as described herein.

The free end 22m of the deployed anchor 15m may optionally be rotated around one or more structures on the second side of the native valve. The one or more structures may comprise one or more valve leaflets of the native valve. Alternatively, or in combination, the one or more structures may comprise one or more chordae of the left ventricle.

The anchor 15m may then be released from the distal end of the delivery device 30m. The anchor 15m may be released from the distal end of the delivery device 30m on the second side of the native valve.

The frame structure 12m may be expanded within the native valve from an unexpanded configuration to an expanded configuration.

The frame structure 12m may be released from the distal end of the delivery device 30m. In some embodiments, at least a portion the frame structure 12m may be expanded within at least a portion of the deployed anchor to anchor 15m the frame structure 12m to the native valve.

In some embodiments, expanding the frame structure and releasing the frame structure may occur simultaneously.

Finally, the delivery device 30m may be retracted from the native valve.

Additional information about the frame structure may be found in U.S. Provisional Applications No. 62/720,853, 16/546,901, 62/748,162, 62/784,280, 62/813,963, 62/815,791, 62/820,570, 62/828,835, 62/833,425, 62/833,430, 62/851,245, 62/872,016, 62/873,454, 62/879,979, 62/894,565, previously incorporated herein by reference in their entireties for all purposes.

Additional information about the anchor may be found in U.S. Provisional Applications No. 62/720,853, 16/546,901, 62/748,162, 62/784,280, 62/813,963, 62/815,791, 62/820,570, 62/828,835, 62/833,425, 62/833,430, 62/851,245, 62/872,016, 62/873,454, 62/879,979, 62/894,565, previously incorporated herein by reference in their entireties for all purposes.

Additional information about the delivery device may be found in U.S. Provisional Applications No. 62/720,853, 16/546,901, 62/748,162, 62/784,280, 62/813,963, 62/815,791, 62/820,570, 62/828,835, 62/833,425, 62/833,430, 62/851,245, 62/872,016, 62/873,454, 62/879,979, 62/894,565, previously incorporated herein by reference in their entireties for all purposes.

The valve prosthesis may be substantially similar to any of the valve prostheses described in U.S. Provisional Applications No. 62/720,853, 16/546,901, 62/748,162, 62/784,280, 62/813,963, 62/815,791, 62/820,570, 62/828,835, 62/833,425, 62/833,430, 62/851,245, 62/872,016, 62/873,454, 62/879,979, 62/894,565, previously incorporated herein by reference in their entireties for all purposes.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The embodiments were chosen and described to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The embodiments were chosen and described to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating a diseased native valve in a patient, the method comprising:
   advancing a distal end of a delivery device to a first side of a native valve, wherein the distal end of the delivery device is detachably coupled to an anchor and a frame structure;
   deploying the anchor from a delivery configuration to a deployed configuration on the first side of the native valve;
   advancing the anchor in the deployed configuration from the first side of the native valve to a second side of the native valve such that the anchor is located only on the second side of the native valve;
   rotating a free end of the anchor in the deployed configuration around one or more structures on the second side of the native valve;
   releasing the anchor from the distal end of the delivery device;
   expanding the frame structure within the native valve from a compressed configuration to an expanded configuration;
   releasing the frame structure from the distal end of the delivery device; and
   retracting the delivery device from the native valve.

2. The method of claim 1, further comprising steering the distal end of the delivery device such that the distal end of the delivery device points towards the first side of the native valve.

3. The method of claim 1, wherein advancing the anchor comprises pushing the anchor through the native valve.

4. The method of claim 1, wherein advancing the anchor comprises rotating the anchor through the native valve.

5. The method of claim 1, wherein the frame structure comprises first and second opposite ends and wherein expanding the frame structure comprises expanding the frame structure such that the first end extends above the first side of the native valve and the second end extends below the second side of the native valve.

6. The method of claim 1, wherein expanding the frame structure comprises expanding at least a portion the frame structure within at least a portion of the deployed anchor to anchor the frame structure to the native valve.

7. The method of claim 1, wherein expanding the frame structure and releasing the frame structure occur simultaneously.

8. The method of claim 1, wherein the frame structure is balloon-expandable and wherein expanding the frame structure comprises inflating a balloon disposed within the frame structure, wherein inflation of the balloon causes expansion of the frame structure.

9. The method of claim 1, wherein the frame structure is self-expanding and wherein expanding the frame structure comprises releasing the frame structure from radial constriction by the delivery device.

10. The method of claim 1, wherein the one or more structures comprise one or more valve leaflets of the native valve.

11. The method of claim 1, wherein the one or more structures comprise one or more chordae of the left ventricle.

12. The method of claim 1, wherein the free end is disposed radially outward from a main body of the anchor in the deployed configuration in order to facilitate rotation of the free end around the one or more structures.

13. The method of claim 1, wherein the free end comprises an atraumatic tip.

14. The method of claim 1, wherein the free end comprises a ball tip.

15. The method of claim 1, wherein the free end is configured for piercing tissue.

16. The method of claim 1, wherein the frame structure comprises a valve segment therewithin comprising a biocompatible one-way valve.

17. The method of claim 1, wherein the native valve is in a heart of a patient.

18. The method of claim 17, further comprising transseptally inserting the distal end of the delivery device into a left atrium of the heart.

19. The method of claim 17, wherein the native valve comprises a mitral valve, the first side of the native valve comprises a left atrium, and the second side of the native valve comprises a left ventricle.

20. The method of claim 17, wherein the native valve comprises an aortic valve, the first side of the native valve comprises a left ventricle, and the second side of the native valve comprises an aorta.

21. The method of claim 17, wherein the native valve comprises a tricuspid valve, the first side of the native valve comprises a right atrium, and the second side of the native valve comprises a right ventricle.

22. The method of claim 1, wherein the anchor comprises a curved wire.

23. The method of claim 22, wherein the curved wire comprises a helical wire.

24. The method of claim 23, wherein the anchor comprises a first portion comprising the helical wire and another portion.

25. The method of claim 23, wherein the helical wire has a generally tubular shape.

26. The method of claim 25, wherein the free end of the helical wire extends radially outward from the tubular shape.

27. The method of claim 23, wherein the helical wire has a generally frustoconical shape.

28. The method of claim 27, wherein the free end of the helical wire extends radially outward from the frustoconical shape.

29. The method of claim 23, wherein the helical wire has a generally cylindrical shape.

30. The method of claim 29, wherein the free end of the helical wire extends radially outward from the cylindrical shape.

* * * * *